(12) United States Patent
Sparey et al.

(10) Patent No.: US 11,161,862 B2
(45) Date of Patent: *Nov. 2, 2021

(54) PHOSPHONIUM-ION TETHERED TETRACYCLINE DRUGS FOR TREATMENT OF CANCER

(71) Applicant: Oxford University Innovation Limited, Oxford (GB)

(72) Inventors: Tim Sparey, London (GB); Andrew Ratcliffe, London (GB); Edward Cochrane, Nottingham (GB); Brett Stevenson, Nottingham (GB); David Hallett, Buckinghamshire (GB); Franz Lagasse, Nottingham (GB); Gilbert Lassalle, Hamburg (DE); Alexandre Froidbise, Hamburg (DE)

(73) Assignee: Oxford University Innovation Limited, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/606,399

(22) PCT Filed: Apr. 20, 2018

(86) PCT No.: PCT/EP2018/060230
§ 371 (c)(1),
(2) Date: Oct. 18, 2019

(87) PCT Pub. No.: WO2018/193113
PCT Pub. Date: Oct. 25, 2018

(65) Prior Publication Data
US 2020/0123182 A1   Apr. 23, 2020

(30) Foreign Application Priority Data

Apr. 20, 2017 (GB) .................................... 1706323
Dec. 22, 2017 (GB) .................................... 1721749

(51) Int. Cl.
*C07F 9/54*     (2006.01)
*C07F 9/572*    (2006.01)
*C07F 9/58*     (2006.01)

(52) U.S. Cl.
CPC .......... *C07F 9/5442* (2013.01); *C07F 9/5407* (2013.01); *C07F 9/5456* (2013.01); *C07F 9/572* (2013.01); *C07F 9/58* (2013.01)

(58) Field of Classification Search
None
See application file for complete search history.

(56) References Cited

U.S. PATENT DOCUMENTS

| 3,517,067 | A | 6/1970 | Stern |
| 6,165,999 | A | 12/2000 | Vu |
| 2020/0131208 | A1* | 4/2020 | Sparey .................. A61K 31/66 |

FOREIGN PATENT DOCUMENTS

| WO | WO-99/26582 A2 | 6/1999 |
| WO | WO-2010/121177 A2 | 10/2010 |
| WO | WO-2013/019975 A1 | 2/2013 |

OTHER PUBLICATIONS

CAS Database XP002783032, Shouzhou et al., "Amphoteric tetracycline-sensitive electrodes and their selectivities," (1989).
International Search Report and Written Opinion for International Application No. PCT/EP2018/060230 dated Jul. 27, 2018.
Han et al., "Mitochondrial Delivery of Doxorubicin via Triphenylphosphine Modification for Overcoming Drug Resistance in MDA-MB-435/DOX Cells," Molecular Pharmaceutics, 11(8):2640-2649 (2014).
Lamb et al., "Antibiotics that target mitochondria effectively eradicate cancer stem cells, across multiple tumor types: Treating cancer like an infectious disease," Oncotarget 6(7):4569-4584 (2015).
Ross et al., "Lipophilic Triphenylphosphonium Cations as Tools in Mitochondrial Bioenergetics and Free Radical Biology," Biochemistry Moscow, 70(2):222-230 (2005).
Third Party Observation for International Application No. PCT/EP2018/060230 dated May 17, 2019.
United Kingdom Search Report for Application No. GB1706323.1 dated Mar. 6, 2018.

* cited by examiner

*Primary Examiner* — Joseph R Kosack
(74) *Attorney, Agent, or Firm* — Foley Hoag LLP; Dana M. Gordon

(57) ABSTRACT

This invention relates to compounds that are useful as cancer therapies. The compounds comprise derivatives of tetracycline antibiotics, e.g. doxycycline, having a phosphonium cation tethered to the tetracycline tetracycle. The invention also relates to methods of using said compounds and to pharmaceutical formulations comprising said compounds.

20 Claims, No Drawings

PHOSPHONIUM-ION TETHERED TETRACYCLINE DRUGS FOR TREATMENT OF CANCER

RELATED APPLICATIONS

This application is a U.S. National Stage of International Application No. PCT/EP2018/060230, filed Apr. 20, 2018; which claims priority to Great Britain Application No. 1721749.8, filed Dec. 22, 2017; and Great Britain Application No. 1706323.1, filed Apr. 20, 2017.

This invention relates to compounds that disrupt cell function, such as the disruption of cell metabolism in particular cancer cell metabolism, that are useful as cancer therapies. The compounds comprise derivatives of tetracycline antibiotics, e.g. doxycycline, having a phosphonium cation tethered to the tetracycline tetracycle. The invention also relates to methods of using said compounds and to pharmaceutical formulations comprising said compounds.

BACKGROUND

Cancer is the fourth greatest cause of mortality in the developed world. In 2016 it was predicted that more than 1.6 million new cases of cancer would be diagnosed in the U.S. alone, and that cancer would be responsible for nearly 600,000 U.S. deaths.

Cancer is characterized by the unregulated proliferation of cells, which disrupt the function of tissues. The proliferation of cells can be caused by an abnormal increase in cell production or a disruption in the cell death pathway. In any event, disruptors of cell function can impact the proliferation of cells and, in particular, cancer cells by reducing or inhibiting cell proliferation. For example, the modulation of cancer cell metabolism can lead to the reduction or inhibition of cell proliferation. Equally, the compounds of the invention may reduce, disrupt, or inhibit the growth or proliferation of a cancer cell or it may induce the death of a cancer cell. As such, cancer cell metabolism, and reducing cell proliferation, is a potential target for disrupting cancer growth and ultimately a therapeutic pathway for cancer treatment. Accordingly, the certain embodiments of the invention contemplate compounds that modulate cancer cell metabolism and/or reduce cell proliferation. Reduction in cell proliferation could be achieved either by increasing cell death or by reducing the rate of cell growth.

It has been observed that certain compounds having antibiotic activity have a beneficial effect when administered to patients with cancer. The inventors have found that compounds having a phosphonium ion linked to a tetracycline antibiotic are able to modulate cancer cell metabolism in cancer cell lines and, accordingly, prevent and/or treat cancer.

The "prevention" of cancer may be taken as including the prevention of the formation of tumours, including primary tumours, metastatic tumours, or tumours associated with cancer onset, resistance or relapse. The prevention of cancer may also be taken as encompassing the prevention of the progression of cancer. In this context, prevention of development of cancer may be demonstrated by preventing an increase in the "stage" of a tumour (using an appropriate cancer staging method) that has been treated using the compounds of the invention. The prevention of increase in cancer stage may be compared to progression of an untreated tumour, or compared to the extent of progression that would be expected by a clinician in the event that the tumour was not treated.

The "treatment" of cancer may be taken as including any improvement of pathology, symptoms or prognosis that is achieved in respect of cancer in a subject receiving compounds of the invention. Treatment may be indicated by a partial improvement of such indications, or by a total improvement (e.g. the absence of cancer following medical use of the compounds of the invention).

Accordingly, the prevention and/or treatment as defined above are intended aims of certain embodiments of the invention. The above definitions of treatment or prevention of cancer apply equally to the specific forms of cancer that are also contemplated.

Recent developments in cancer therapy have suggested that certain antibiotic compounds may be useful in cancer treatment. The mechanisms by which these agents, which include the antibiotics azithromycin and doxycycline, exert a therapeutic effect have been open to markedly different explanations. Some authors have suggested that these agents inhibit matrix metalloproteinases (MMPs) and thereby achieve an anti-inflammatory effect, while others suggest that they impair the cells' response to DNA damage, thereby increasing the effectiveness of chemotherapy or radiotherapy on bulk tumour cells. Still other articles have indicated that the antibiotics target mitochondrial function.

However, there have also been reports that antibiotic use can increase the risk of colorectal cancer. A recent study identified that increasing duration of antibiotic use was significantly associated with an increased risk of colorectal adenoma (Cao Y, Wu K, Mehta R, et al, "Long-term use of antibiotics and risk of colorectal adenoma", Gut, 2017, 0, page 1-7).

Surprisingly, the inventors have found that the compounds having a phosphonium ion linked to a tetracycline antibiotic have increased activity against certain cancer cell lines compared to the corresponding antibiotic, e.g. doxycycline. This is demonstrated by the reduced cancer cell proliferation observed in a cell confluence assay.

Also provided is a method of preventing and/or treating cancer in a subject needing such prevention and/or treatment, the method comprising administering a therapeutically effective amount of a compound of the invention to the subject. A therapeutically effective amount of a compound of the invention may be an amount of such a compound sufficient to treat a variety of cancers, including the modulation of cancer cells or other dysfunctional cells (such as tumour initiating cells, stem-like cancer cells, cancer stem cells, or a population of cells with stem cell-like features that exist in tumors and that give rise to the bulk of tumor cells with more differentiated phenotypes). References to cancer cells include hybrid cells and giant cells. It will be appreciated that the therapeutically effective amount of the compound of the invention may be provided in a single incidence of administration, or cumulatively through multiple incidences of administration.

The same considerations regarding the types of cancers to be treated, and benefits provided by treatment, described with respect to the medical uses of the compounds of the invention also apply to the methods of treatment of the invention.

BRIEF SUMMARY OF THE DISCLOSURE

In a first aspect of the invention there is provided a compound comprising an ion of formula (I) or a pharmaceutically acceptable salt thereof:

(I)

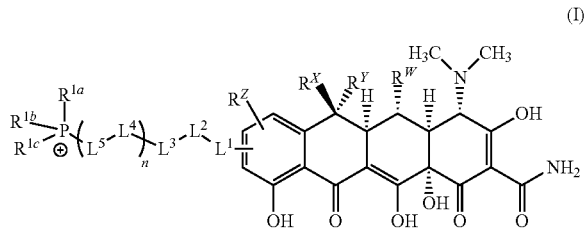

wherein
$R^W$ is H or OH;
$R^X$ is H or OH;
$R^Y$ is H, $C_1$-$C_6$-alkyl or $C_1$-$C_6$-haloalkyl;
$R^Z$ is H, $NR^{Z1}R^{Z2}$, $C_1$-$C_6$-haloalkyl, or halo, wherein $R^{Z1}$ and $R^{Z2}$ are both independently selected from H or $C_1$-$C_6$-alkyl;
-$L^1$- is absent or is —$CR^{2a}R^{2b}$—;
-$L^2$- is absent or is independently selected from —O—, —S—, —$NR^{3a}$—, —$C(O)NR^{3b}$—, —C(O)—, —OC(O)—, —$NR^{3b}C(O)$—, $NR^5S(O)_2$—, —$OC(O)NR^{3b}$—, —$NR^{3b}C(O)O$— and —$NR^{3b}C(O)NR^{3b}$;
-$L^3$- and -$L^5$- are each independently at each occurrence selected from —$C_1$-$C_4$-alkylene-, each alkylene group being unsubstituted or substituted with from 1 to 10 independently selected $R^4$ groups; provided that any -$L^3$- or -$L^5$- group that is attached at each end to an atom selected from oxygen, nitrogen, sulphur or phosphorous is —$C_2$-$C_4$-alkylene-;
-$L^4$- is independently at each occurrence either absent or is selected from: —O—, —S—, —$NR^{3a}$—, —C(O)—, —OC(O)—, —C(O)O—, —$SO_2$—, —S(O)—, —$NR^{3b}C(O)$—, —$C(O)NR^{3b}$, $NR^{3b}S(O)_2$—, —$S(O)_2NR^{3b}$—, —$OC(O)NR^{3b}$—, —$NR^{3b}C(O)O$—, $NR^{3b}C(O)NR^{3b}$, —$CR^5$=$CR^5$— and —C≡C—;
n is an integer selected from 0, 1, 2, 3, 4 and 5;
wherein $L^1$, $L^2$, $L^3$ $L^4$ and $L^5$ together form a linker and $L^1$, $L^2$, $L^3$ $L^4$ and $L^5$ are selected such that length of the linker is from 3 to 16 atoms;
$R^{1a}$, $R^{1b}$ and $R^{1c}$ are each independently selected from phenyl, biphenyl, naphthyl, 5-, 6-, 9- or 10-membered heteroaryl, $C_3$ to $C_8$-cycloalkyl, $C_1$-$C_8$-alkyl and 4- to 8-membered heterocycloalkyl; wherein said phenyl, biphenyl, naphthyl, 5-, 6-, 9- or 10-membered heteroaryl is optionally substituted with from 1 to 5 independently selected $R^{1d}$ groups; and
wherein said $C_3$ to $C_8$-cycloalkyl, $C_1$-$C_8$-alkyl and 4- to 8-membered heterocycloalkyl is optionally substituted with from 1 to 5 independently selected $R^{1e}$ groups; provided that $R^{1a}$, $R^{1b}$ and $R^{1c}$ are not each unsubstituted phenyl; wherein $R^{1a}$ and $R^{1b}$ are optionally connected to each other via a bond or a group selected from —O—, $NR^{6a}$, and $C_1$-$C_3$-alkylene;
$R^{1d}$ is independently at each occurrence selected from: $C_1$-$C_6$-alkyl, $C_2$-$C_6$-alkynyl, $C_2$-$C_6$-alkenyl, $C_1$-$C_6$-haloalkyl, $C_3$-$C_6$-cycloalkyl, 5- to 8-membered heterocycloalkyl, 5-, 6-, 9- or 10-membered heteroaryl, phenyl, $OR^6$, $SR^7$, $NR^7R^8$, $C(O)OR^7$, $C(O)NR^7R^7$, halo, cyano, nitro, $C(O)R^7$, $S(O)_2OR^7$, $S(O)R^7$, $S(O)_2R^7$, $NR^7C(O)OR^7$, $OC(O)NR^7R^7$ and $S(O)_2NR^7R^7$;
$R^{1e}$ is independently at each occurrence selected from: oxo, $C_1$-$C_6$-alkyl, $C_2$-$C_6$-alkynyl, $C_2$-$C_6$-alkenyl, $C_1$-$C_6$-haloalkyl, $C_3$-$C_6$-cycloalkyl, 5- to 8-membered heterocycloalkyl, 5-, 6-, 9- or 10-membered heteroaryl, phenyl, $OR^6$, $SR^7$, $NR^7R^8$, $C(O)OR^7$, $C(O)NR^7R^7$, halo, cyano, nitro, $C(O)R^7$, $S(O)_2OR^7$, $S(O)R^7$, $S(O)_2R^7$, $S(O)_2NR^7R^7$, $OC(O)NR^7R^7$ and $NR^7C(O)OR^7$;
$R^{2a}$ and $R^{2b}$ are each independently selected from H and $C_1$-$C_4$-alkyl;

$R^{3a}$ is independently at each occurrence selected from H, $C_1$-$C_6$-alkyl, —C(O)—$C_1$-$C_6$-alkyl and —$S(O)_2$—$C_1$-$C_6$-alkyl;
$R^{3b}$ is each independently at each occurrence selected from H and $C_1$-$C_6$-alkyl;
$R^4$ is independently at each occurrence selected from: $C_1$-$C_6$-alkyl, $C_2$-$C_6$-alkynyl, $C_2$-$C_6$-alkenyl, $C_1$-$C_6$-haloalkyl, $OR^6$, $SR^7$, $NR^7R^8$, $C(O)OR^7$, $C(O)NR^7R^7$, halo, cyano, nitro, $C(O)R^7$, $S(O)_2OR^7$, $S(O)R^7$, $S(O)_2R^7$, $NR^7C(O)OR^7$, $OC(O)NR^7R^7$ and $S(O)_2NR^7R^7$;
$R^5$ is independently at each occurrence selected from H, $C_1$-$C_4$-alkyl and halo;
$R^6$ is independently at each occurrence selected from: H, $C_1$-$C_6$-alkyl and $C_1$-$C_6$-haloalkyl;
$R^7$ and $R^{6a}$ are each independently at each occurrence selected from: H and $C_1$-$C_6$-alkyl;
$R^8$ is independently at each occurrence selected from: H, $C_1$-$C_6$-alkyl, $C(O)C_1$-$C_6$-alkyl and $S(O)_2$—$C_1$-$C_6$-alkyl;
and wherein any of the abovementioned alkyl, alkenyl, alkynyl, cycloalkyl, heterocycloalkyl, heteroaryl or phenyl groups is optionally substituted where chemically allowable by from 1 to 4 groups independently selected from oxo, $C_1$-$C_6$-alkyl, $C_2$-$C_6$-alkynyl, $C_2$-$C_6$-alkenyl, $C_1$-$C_6$-haloalkyl, $OR^a$, $NR^aR^b$, $SR^a$, $C(O)OR^a$, $C(O)NR^aR^a$, halo, cyano, nitro, $C(O)R^a$, $S(O)_2OR^a$, $S(O)_2R^a$, $S(O)R^a$ and $S(O)_2NR^aR^a$; wherein $R^a$ is independently at each occurrence selected from: H and $C_1$-$C_6$-alkyl; and $R^b$ is independently at each occurrence selected from: H, $C_1$-$C_6$-alkyl, $C(O)C_1$-$C_6$-alkyl and $S(O)_2$—$C_1$-$C_6$-alkyl.

A compound comprising an ion of formula (I) or a pharmaceutically acceptable salt thereof:

(I)

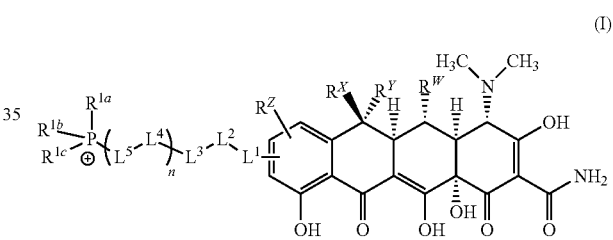

wherein
$R^W$ is H or OH;
$R^X$ is H or OH;
$R^Y$ is H, $C_1$-$C_6$-alkyl or $C_1$-$C_6$-haloalkyl;
$R^Z$ is H, $NR^{Z1}R^{Z2}$, $C_1$-$C_6$-haloalkyl, or halo, wherein $R^{Z1}$ and $R^{Z2}$ are both independently selected from H or $C_1$-$C_6$-alkyl;
-$L^1$- is absent or is —$CR^{2a}R^{2b}$—;
-$L^2$- is absent or is independently selected from —O—, —S—, —$NR^{3a}$—, —$C(O)NR^{3b}$—, —C(O)—, —OC(O)—, —$NR^{3b}C(O)$—, $NR^5S(O)_2$—, —$OC(O)NR^{3b}$—, —$NR^{3b}C(O)O$— and —$NR^{3b}C(O)NR^{3b}$;
-$L^3$- and -$L^5$- are each independently at each occurrence selected from —$C_1$-$C_4$-alkylene-, each alkylene group being unsubstituted or substituted with from 1 to 10 independently selected $R^4$ groups; provided that any -$L^3$- or -$L^5$- group that is attached at each end to an atom selected from oxygen, nitrogen, sulphur or phosphorous is —$C_2$-$C_4$-alkylene-;
-$L^4$- is independently at each occurrence either absent or is selected from: —O—, —S—, —$NR^{3a}$—, —C(O)—, —OC(O)—, —C(O)O—, —$SO_2$—, —S(O)—, —$NR^{3b}C(O)$—, —$C(O)NR^{3b}$, $NR^{3b}S(O)_2$—, —$S(O)_2NR^{3b}$—, —$OC(O)NR^{3b}$—, —$NR^{3b}C(O)O$—, $NR^{3b}C(O)NR^{3b}$, —$CR^5$=$CR^5$— and —C≡C—;
n is an integer selected from 0, 1, 2, 3, 4 and 5;
wherein $L^1$, $L^2$, $L^3$ $L^4$ and $L^5$ together form a linker and $L^1$, $L^2$, $L^3$ $L^4$ and $L^5$ are selected such that length of the linker is from 3 to 16 atoms;

$R^{1a}$, $R^{1b}$ and $R^{1c}$ are each independently selected from phenyl, biphenyl, naphthyl, 5-, 6-, 9- or 10-membered heteroaryl, $C_3$ to $C_8$-cycloalkyl, $C_1$-$C_8$-alkyl and 5- to 8-membered heterocycloalkyl; wherein said phenyl, biphenyl, naphthyl, 5-, 6-, 9- or 10-membered heteroaryl is optionally substituted with from 1 to 5 independently selected $R^{1d}$ groups; and wherein said $C_3$ to $C_8$-cycloalkyl, $C_1$-$C_8$-alkyl and 5- to 8-membered heterocycloalkyl is optionally substituted with from 1 to 5 independently selected $R^{1e}$ groups; provided that $R^{1a}$, $R^{1b}$ and $R^{1c}$ are not each unsubstituted phenyl;

$R^{1d}$ is independently at each occurrence selected from: $C_1$-$C_6$-alkyl, $C_2$-$C_6$-alkynyl, $C_2$-$C_6$-alkenyl, $C_1$-$C_6$-haloalkyl, $C_3$-$C_6$-cycloalkyl, 5- to 8-membered heterocycloalkyl, 5-, 6-, 9- or 10-membered heteroaryl, phenyl, $OR^6$, $SR^7$, $NR^7R^8$, $C(O)OR^7$, $C(O)NR^7R^7$, halo, cyano, nitro, $C(O)R^7$, $S(O)_2OR^7$, $S(O)R^7$, $S(O)_2R^7$, $NR^7C(O)OR^7$, $OC(O)NR^7R^7$ and $S(O)_2NR^7R^7$;

$R^{1e}$ is independently at each occurrence selected from: oxo, $C_1$-$C_6$-alkyl, $C_2$-$C_6$-alkynyl, $C_2$-$C_6$-alkenyl, $C_1$-$C_6$-haloalkyl, $C_3$-$C_6$-cycloalkyl, 5- to 8-membered heterocycloalkyl, 5-, 6-, 9- or 10-membered heteroaryl, phenyl, $OR^6$, $SR^7$, $NR^7R^8$, $C(O)OR^7$, $C(O)NR^7R^7$, halo, cyano, nitro, $C(O)R^7$, $S(O)_2OR^7$, $S(O)R^7$, $S(O)_2R^7$, $S(O)_2NR^7R^7$, $OC(O)NR^7R^7$ and $NR^7C(O)OR^7$;

$R^{2a}$ and $R^{2b}$ are each independently selected from H and $C_1$-$C_4$-alkyl;

$R^{3a}$ is independently at each occurrence selected from H, $C_1$-$C_6$-alkyl, —C(O)—$C_1$-$C_6$-alkyl and —S(O)$_2$—$C_1$-$C_6$-alkyl;

$R^{3b}$ is each independently at each occurrence selected from H and $C_1$-$C_6$-alkyl;

$R^4$ is independently at each occurrence selected from: $C_1$-$C_6$-alkyl, $C_2$-$C_6$-alkynyl, $C_2$-$C_6$-alkenyl, $C_1$-$C_6$-haloalkyl, $OR^6$, $SR^7$, $NR^7R^8$, $C(O)OR^7$, $C(O)NR^7R^7$, halo, cyano, nitro, $C(O)R^7$, $S(O)_2OR^7$, $S(O)R^7$, $S(O)_2R^7$, $NR^7C(O)OR^7$, $OC(O)NR^7R^7$ and $S(O)_2NR^7R^7$;

$R^5$ is independently at each occurrence selected from H, $C_1$-$C_4$-alkyl and halo;

$R^6$ is independently at each occurrence selected from: H, $C_1$-$C_6$-alkyl and $C_1$-$C_6$-haloalkyl;

$R^7$ is independently at each occurrence selected from: H and $C_1$-$C_6$-alkyl;

$R^8$ is independently at each occurrence selected from: H, $C_1$-$C_6$-alkyl, $C(O)C_1$-$C_6$-alkyl and $S(O)_2$—$C_1$-$C_6$-alkyl;

and wherein any of the abovementioned alkyl, alkenyl, alkynyl, cycloalkyl, heterocycloalkyl, heteroaryl or phenyl groups is optionally substituted where chemically allowable by from 1 to 4 groups independently selected from oxo, $C_1$-$C_6$-alkyl, $C_2$-$C_6$-alkynyl, $C_2$-$C_6$-alkenyl, $C_1$-$C_6$-haloalkyl, $OR^a$, $NR^aR^b$, $SR^a$, $C(O)OR^a$, $C(O)NR^aR^a$, halo, cyano, nitro, $C(O)R^a$, $S(O)_2OR^a$, $S(O)_2R^a$, $S(O)R^a$ and $S(O)_2NR^aR^a$; wherein $R^a$ is independently at each occurrence selected from: H and $C_1$-$C_6$-alkyl; and $R^b$ is independently at each occurrence selected from: H, $C_1$-$C_6$-alkyl, $C(O)C_1$-$C_6$-alkyl and $S(O)_2$—$C_1$-$C_6$-alkyl.

It may be that $R^x$ is H.

For the absence of doubt, where n is greater than 1, each -$L^4$-$L^5$- unit is selected independently of the other -$L^4$-$L^5$- unit or -$L^4$-$L^5$- units. Thus, each -$L^4$-$L^5$- unit may be the same or they may be different.

For the absence of doubt the atom length of the linkers formed by $L^1$, $L^2$, $L^3$ $L^4$ and $L^5$ is the number of atoms in a straight chain from the phosphorous atom of the phosphonium to the carbon atom via which the linker is attached to the tetracycline portion of the cations. The length does not include any substituents or branching that might be present on the chain.

For the absence of doubt where a bivalent group (e.g. $L^1$, $L^2$, $L^3$, $L^4$, $L^5$ or a combination thereof) is represented in text, the left-hand portion of the linker group is attached, either directly or indirectly, to the carbon atom via which the linker is attached to the tetracycline portion of the cation and the right hand portion of the linker group is attached, either directly or indirectly, to the phosphorous atom of the phosphonium.

In embodiments the ion of formula (I) may be an ion according to formula (II):

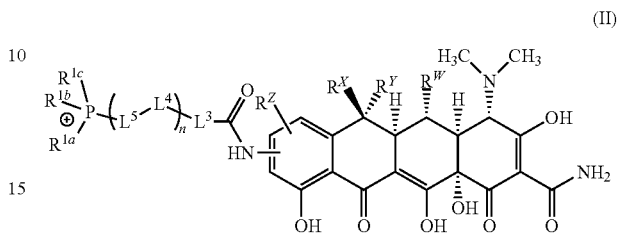

(II)

In embodiments the ion of formula (I) may be an ion according to formula (III):

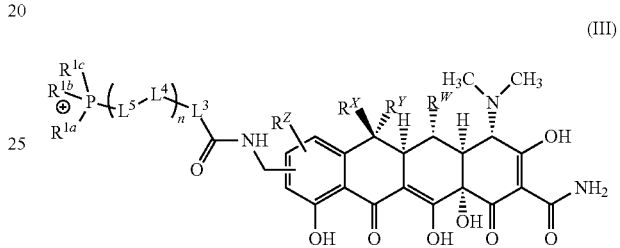

(III)

In embodiments the ion of formula (I) may be an ion according to formula (IIa):

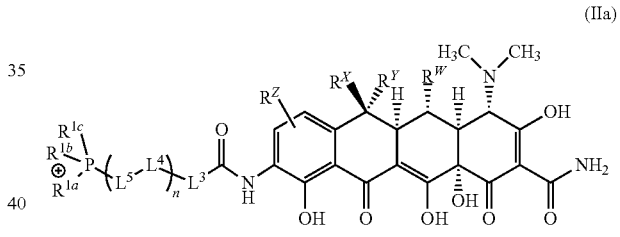

(IIa)

In embodiments the ion of formula (I) may be an ion according to formula (IIIa):

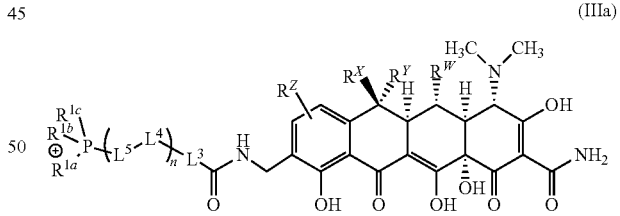

(IIIa)

In embodiments the ion of formula (I) may be an ion according to formula (IIb):

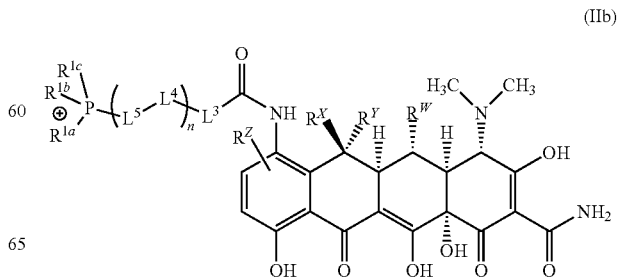

(IIb)

In embodiments the ion of formula (I) may be an ion according to formula (IIIb):

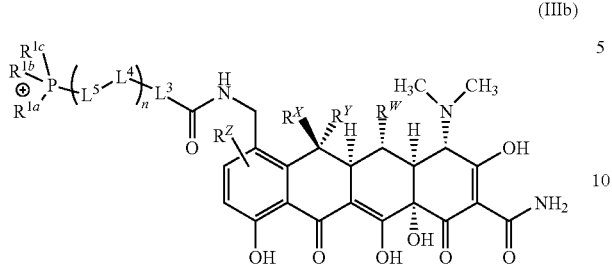

(IIIb)

In an embodiment the ion of formula (I) may be an ion according to formula (IV):

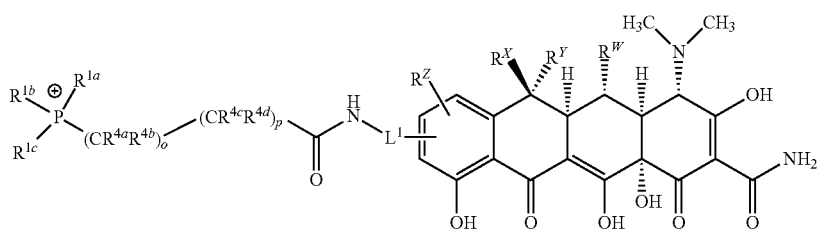

(IV)

wherein o is selected from 3 to 10; p is selected from 1 to 3, wherein $R^{4a}$ and $R^{4b}$ are each independently at each occurrence selected from: H, $C_1$-$C_6$-alkyl, $C_2$-$C_6$-alkynyl, $C_2$-$C_6$-alkenyl, $C_1$-$C_6$-haloalkyl, $OR^6$, $SR^7$, $NR^7R^8$, $C(O)OR^7$, $C(O)NR^7R^7$, halo, cyano, nitro, $C(O)R^7$, $S(O)_2OR^7$, $S(O)_2R^7$ and $S(O)_2NR^7R^7$; and $R^{4c}$ and $R^{4d}$ are each independently at each occurrence selected from: H, $C_1$-$C_6$-alkyl, $C_1$-$C_6$-haloalkyl, $NR^7R^8$, $OR^6$, and halo.

In an embodiment the ion of formula (I) may be an ion according to formula (V):

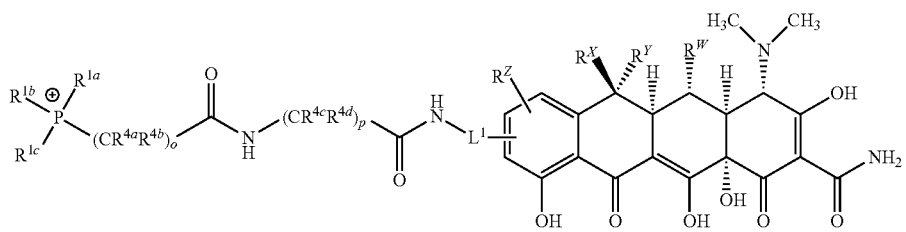

(V)

wherein o is selected from 3 to 10; p is selected from 1 to 3, wherein $R^{4a}$ and $R^{4b}$ are each independently at each occurrence selected from: H, $C_1$-$C_6$-alkyl, $C_2$-$C_6$-alkynyl, $C_2$-$C_6$-alkenyl, $C_1$-$C_6$-haloalkyl, $OR^6$, $SR^7$, $NR^7R^8$, $C(O)OR^7$, $C(O)NR^7R^7$, halo, cyano, nitro, $C(O)R^7$, $S(O)_2OR^7$, $S(O)_2R^7$ and $S(O)_2NR^7R^7$; and $R^{4c}$ and $R^{4d}$ are each independently at each occurrence selected from: H, $C_1$-$C_6$-alkyl, $C_1$-$C_6$-haloalkyl, $NR^7R^8$, $OR^6$, and halo.

In embodiments the ion of formula (I) may be an ion according to formula (IVa):

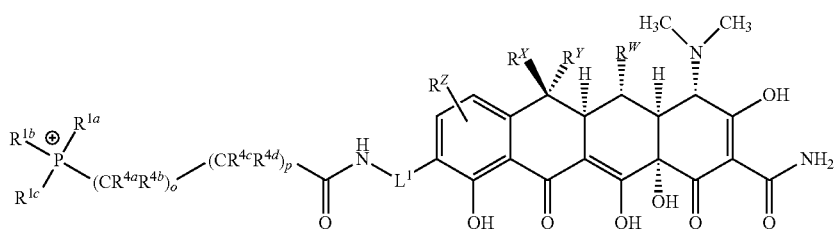

(IVa)

wherein o is selected from 3 to 10; p is selected from 1 to 3, wherein $R^{4a}$ and $R^{4b}$ are each independently at each occurrence selected from: H, $C_1$-$C_6$-alkyl, $C_2$-$C_6$-alkynyl, $C_2$-$C_6$-alkenyl, $C_1$-$C_6$-haloalkyl, $OR^6$, $SR^7$, $NR^7R^8$, $C(O)OR^7$, $C(O)NR^7R^7$, halo, cyano, nitro, $C(O)R^7$, $S(O)_2OR^7$, $S(O)_2R^7$ and $S(O)_2NR^7R^7$; and $R^{4c}$ and $R^{4d}$ are each independently at each occurrence selected from: H, $C_1$-$C_6$-alkyl, $C_1$-$C_6$-haloalkyl, $NR^7R^8$, $OR^6$, and halo.

In embodiments the ion of formula (I) may be an ion according to formula (IVb):

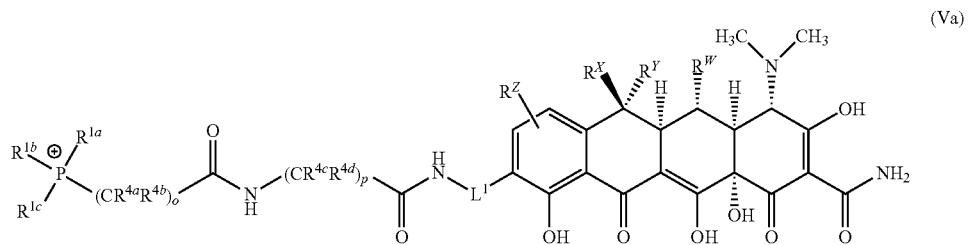

(IVb)

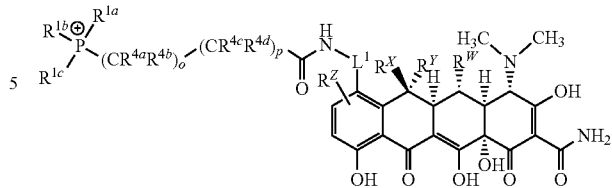

(Va)

wherein o is selected from 3 to 10; p is selected from 1 to 3, wherein $R^{4a}$ and $R^{4b}$ are each independently at each occurrence selected from: H, $C_1$-$C_6$-alkyl, $C_2$-$C_6$-alkynyl, $C_2$-$C_6$-alkenyl, $C_1$-$C_6$-haloalkyl, $OR^6$, $SR^7$, $NR^7R^8$, $C(O)OR^7$, $C(O)NR^7R^7$, halo, cyano, nitro, $C(O)R^7$, $S(O)_2OR^7$, $S(O)_2R^7$ and $S(O)_2NR^7R^7$; and $R^{4c}$ and $R^{4d}$ are each independently at each occurrence selected from: H, $C_1$-$C_6$-alkyl, $C_1$-$C_6$-haloalkyl, $NR^7R^8$, $OR^6$, and halo.

In embodiments the ion of formula (I) may be an ion according to formula (Va):

wherein o is selected from 3 to 10; p is selected from 1 to 3, wherein $R^{4a}$ and $R^{4b}$ are each independently at each occurrence selected from: H, $C_1$-$C_6$-alkyl, $C_2$-$C_6$-alkynyl, $C_2$-$C_6$-alkenyl, $C_1$-$C_6$-haloalkyl, $OR^6$, $SR^7$, $NR^7R^8$, $C(O)OR^7$, $C(O)NR^7R^7$, halo, cyano, nitro, $C(O)R^7$, $S(O)_2OR^7$, $S(O)_2R^7$ and $S(O)_2NR^7R^7$; and $R^{4c}$ and $R^{4d}$ are each independently at each occurrence selected from: H, $C_1$-$C_6$-alkyl, $C_1$-$C_6$-haloalkyl, $NR^7R^8$, $OR^6$, and halo.

In embodiments the ion of formula (I) may be an ion according to formula (Vb):

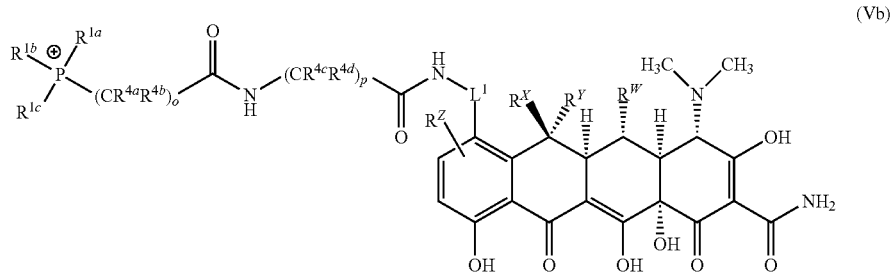

(Vb)

wherein o is selected from 3 to 10; p is selected from 1 to 3, wherein $R^{4a}$ and $R^{4b}$ are each independently at each occurrence selected from: H, $C_1$-$C_6$-alkyl, $C_2$-$C_6$-alkynyl, $C_2$-$C_6$-alkenyl, $C_1$-$C_6$-haloalkyl, $OR^6$, $SR^7$, $NR^7R^8$, $C(O)OR^7$, $C(O)NR^7R^7$, halo, cyano, nitro, $C(O)R^7$, $S(O)_2OR^7$, $S(O)_2R^7$ and $S(O)_2NR^7R^7$; and $R^{4c}$ and $R^{4d}$ are each independently at each occurrence selected from: H, $C_1$-$C_6$-alkyl, $C_1$-$C_6$-haloalkyl, $NR^7R^8$, $OR^6$, and halo.

The following statements apply to compounds of any of formulae (I) to (Vb). These statements are independent and interchangeable. In other words, any of the features described in any one of the following statements may (where chemically allowable) be combined with the features described in one or more other statements below. In particular, where a compound is exemplified or illustrated in this specification, any two or more of the statements below which describe a feature of that compound, expressed at any level of generality, may be combined so as to represent subject matter which is contemplated as forming part of the disclosure of this invention in this specification.

In embodiments $R^Z$ is H, NMe$_2$, CF$_3$, Cl or F. In embodiments $R^Z$ is H. In embodiments $R^Z$ is NMe$_2$, In embodiments $R^X$ is H. In embodiments $R^X$ is OH.

In embodiments $R^Y$ is H or C$_1$-C$_6$ alkyl, e.g. CH$_3$. In embodiments $R^Y$ is C$_1$-C$_6$ alkyl, e.g. CH$_3$.

In embodiments $R^W$ is H. In embodiments $R^W$ is OH.

In embodiments $R^Z$ is H, NMe$_2$, CF$_3$, Cl or F; $R^X$ is H or OH, $R^Y$ is H or CH$_3$, and $R^W$ is H or OH. In embodiments $R^Z$ is H, NMe$_2$, CF$_3$, Cl or F; $R^X$ is H, $R^Y$ is H or CH$_3$, and $R^W$ is H or OH.

Where $R^z$ is not H, it is preferably positioned para to the OH group depicted in formula (I).

In embodiments $R^Z$ is H, $R^X$ is H, $R^Y$ is CH$_3$, and $R^W$ is OH. Accordingly, the tetracyclic core of formula (I) is equivalent to doxycycline. In embodiments $R^Z$ is H, $R^X$ is OH, $R^Y$ is CH$_3$, and $R^W$ is H. Accordingly, the tetracyclic core of formula (I) is equivalent to tetracycline. In embodiments $R^Z$ is NMe$_2$, $R^X$ is H, $R^Y$ is H, and $R^W$ is H. Accordingly, the tetracyclic core of formula (I) is equivalent to minocycline. In embodiments $R^Z$ is Cl, $R^X$ is OH, $R^Y$ is CH$_3$, and $R^W$ is H. Accordingly, the tetracyclic core of formula (I) is equivalent to chlorotetracycline. In embodiments $R^Z$ is H, $R^X$ is OH, $R^Y$ is CH$_3$, and $R^W$ is OH. Accordingly, the tetracyclic core of formula (I) is equivalent to oxytetracycline.

It may be that the tetracyclic core of the compound of formula (I) is not tetracycline or oxytetracycline.

In embodiments, $R^{1a}$, $R^{1b}$ and $R^{1c}$ are each independently selected from phenyl, biphenyl, 5- or 6-membered heteroaryl and C$_3$ to C$_8$-cycloalkyl, wherein said phenyl, biphenyl and 5- or 6-membered heteroaryl is optionally substituted with from 1 to 5 independently selected R$^{1d}$ groups, and wherein said C$_3$ to C$_8$-cycloalkyl is optionally substituted with from 1 to 5 independently selected R$^{1e}$ groups; provided that $R^{1a}$, $R^{1b}$ and $R^{1c}$ are not each unsubstituted phenyl.

In embodiments, $R^{1a}$, $R^{1b}$ and $R^{1c}$ are each independently selected from phenyl, biphenyl, pyridyl and cyclohexyl, wherein said phenyl, biphenyl and pyridyl is optionally substituted with from 1 to 5 independently selected R$^{1d}$ groups, and wherein said cyclohexyl group is optionally substituted with from 1 to 5 independently selected R$^{1e}$ groups; provided that $R^{1a}$, $R^{1b}$ and $R^{1c}$ are not each unsubstituted phenyl.

In embodiments, $R^{1a}$, $R^{1b}$ and $R^{1c}$ are each independently selected from phenyl, biphenyl, pyridyl and cyclohexyl, wherein said phenyl, biphenyl and pyridyl is optionally substituted with 1 to 3 independently selected R$^{1d}$ groups, and wherein said cyclohexyl group is optionally substituted with 1 to 3 independently selected R$^{1e}$ groups; provided that $R^{1a}$, $R^{1b}$ and $R^{1c}$ are not each unsubstituted phenyl.

In embodiments, $R^{1a}$, $R^{1b}$ and $R^{1c}$ are each independently selected from phenyl, biphenyl, naphthyl, 5-, 6-, 9- or 10-membered heteroaryl; wherein said phenyl, biphenyl, naphthyl, 5-, 6-, 9- or 10-membered heteroaryl is optionally substituted with from 1 to 5 independently selected R$^{1d}$ groups, provided that $R^{1a}$, $R^{1b}$ and $R^{1c}$ are not each unsubstituted phenyl.

In embodiments, $R^{1a}$, $R^{1b}$ and $R^{1c}$ are each independently selected from phenyl, optionally substituted with from 1 to 5 independently selected R$^{1d}$ groups, provided that $R^{1a}$, $R^{1b}$ and $R^{1c}$ are not each unsubstituted phenyl.

In embodiments, $R^{1a}$, $R^{1b}$ and $R^{1c}$ are each independently selected from phenyl; wherein said phenyl is optionally substituted with from 1, 2 or 3 independently selected R$^{1d}$ groups, provided that $R^{1a}$, $R^{1b}$ and $R^{1c}$ are not each unsubstituted phenyl.

In embodiments, $R^{1a}$, $R^{1b}$ and $R^{1c}$ are each independently selected from phenyl; wherein said phenyl is optionally substituted with from 1, 2 or 3 R$^{1d}$ groups; provided that $R^{1a}$, $R^{1b}$ and $R^{1c}$ are not each unsubstituted phenyl.

In embodiments, $R^{1a}$, $R^{1b}$ and $R^{1c}$ are each independently selected from C$_3$ to C$_8$ cycloalkyl, C$_1$-C$_8$-alkyl and 5- to 8-membered heterocycloalkyl; wherein said C$_3$ to C$_8$ cycloalkyl, C$_1$-C$_8$-alkyl and 5- to 8-membered heterocycloalkyl is optionally substituted with from 1 to 5 independently selected R$^{1e}$ groups. In embodiments, $R^{1a}$, $R^{1b}$ and $R^{1c}$ are each independently selected from C$_3$ to C$_8$ cycloalkyl, C$_1$-C$_8$-alkyl and 4- to 8-membered heterocycloalkyl; wherein said C$_3$ to C$_8$ cycloalkyl, C$_1$-C$_8$-alkyl and 4- to 8-membered heterocycloalkyl is optionally substituted with from 1 to 5 independently selected R$^{1e}$ groups.

In embodiments, $R^{1a}$, $R^{1b}$ and $R^{1c}$ are each independently selected from C$_3$ to C$_8$ cycloalkyl, C$_1$-C$_8$-alkyl and 5- to 8-membered heterocycloalkyl; wherein said C$_3$ to C$_8$ cycloalkyl, C$_1$-C$_8$-alkyl and 5- to 8-membered heterocycloalkyl is optionally substituted with from 1 to 5 independently selected R$^{1e}$ groups.

In embodiments $R^{1a}$, $R^{1b}$ and $R^{1c}$ are different or the same.

In embodiments, R$^{1e}$ is independently at each occurrence selected from C$_1$-C$_6$-alkyl, halo, OR$^6$, NR$^7$R$^8$ and S(O)$_2$OR$^7$.

In embodiments, R$^{1e}$ is independently at each occurrence selected from OCH$_3$, OCH$_2$(CH$_3$)$_2$, N(CH$_3$)$_2$, SO$_2$OH, F and Cl.

In embodiments, $R^{1a}$, $R^{1b}$ and $R^{1c}$ are each independently selected from phenyl, biphenyl, pyridyl and cyclohexyl, wherein said phenyl, biphenyl and pyridyl is optionally substituted with 1 to 3 independently selected R$^{1d}$ groups, wherein R$^{1d}$ is independently at each occurrence selected from C$_1$-C$_6$-alkyl, halo, OR$^6$, NR$^7$R$^8$ and S(O)$_2$OR$^7$.

In embodiments, $R^{1a}$, $R^{1b}$ and $R^{1c}$ are each independently selected from phenyl, biphenyl, pyridyl and cyclohexyl, wherein said phenyl, biphenyl and pyridyl is optionally substituted with 1 to 3 independently selected R$^{1d}$ groups, wherein R$^{1d}$ is independently at each occurrence selected from OCH$_3$, OCH$_2$(CH$_3$)$_2$, N(CH$_3$)$_2$, SO$_2$OH, F and Cl.

In embodiments, $R^{1a}$ is C$_3$ to C$_8$-cycloalkyl, $R^{1b}$ is C$_3$ to C$_8$-cycloalkyl and $R^{1c}$ is C$_3$ to C$_8$-cycloalkyl.

In embodiments, $R^{1a}$ and $R^{1b}$ are each unsubstituted phenyl and $R^{1c}$ is independently selected from: substituted phenyl, biphenyl, naphthyl, 5-, 6-, 9- or 10-membered heteroaryl, C$_3$ to C$_8$-cycloalkyl, C$_1$-C$_8$-alkyl and 4- to 8-membered heterocycloalkyl.

In embodiments, $R^{1a}$ and $R^{1b}$ are each unsubstituted phenyl and $R^{1c}$ is independently selected from: substituted phenyl, biphenyl, naphthyl, 5-, 6-, 9- or 10-membered heteroaryl, C$_3$ to C$_8$-cycloalkyl, C$_1$-C$_8$-alkyl and 5- to 8-membered heterocycloalkyl.

In embodiments, $R^{1a}$ and $R^{1b}$ are each unsubstituted phenyl and $R^{1c}$ is substituted phenyl.

In embodiments, $R^{1a}$ and $R^{1b}$ are each unsubstituted phenyl and $R^{1c}$ is pyridyl.

In embodiments, $R^{1a}$ and $R^{1b}$ are each $C_3$ to $C_8$-cycloalkyl and $R^{1c}$ is independently selected from: phenyl, biphenyl, naphthyl, 5-, 6-, 9- or 10-membered heteroaryl, $C_1$-$C_8$-alkyl and 4- to 8-membered heterocycloalkyl.

In embodiments, $R^{1a}$ and $R^{1b}$ are each $C_3$ to $C_8$-cycloalkyl and $R^{1c}$ is independently selected from: phenyl, biphenyl, naphthyl, 5-, 6-, 9- or 10-membered heteroaryl, $C_1$-$C_8$-alkyl and 5- to 8-membered heterocycloalkyl.

In embodiments, $R^{1a}$ and $R^{1b}$ are each cyclohexyl and $R^{1c}$ is substituted biphenyl.

In embodiments, $R^{1a}$, $R^{1b}$ and $R^{1c}$ are each substituted phenyl. It may be that $R^{1a}$, $R^{1b}$ and $R^{1c}$ are each fluorophenyl, e.g. para-fluorophenyl. It may be that $R^{1a}$, $R^{1b}$ and $R^{1c}$ are each chlorophenyl, e.g. para-chlorophenyl. It may be that $R^{1a}$, $R^{1b}$ and $R^{1c}$ are each methoxyphenyl, e.g. para-methoxyphenyl.

In embodiments, $R^{1a}$, $R^{1b}$ and $R^{1c}$ are each $C_3$ to $C_8$-cycloalkyl. In embodiments, $R^{1a}$, $R^{1b}$ and $R^{1c}$ are each cyclohexyl.

In embodiments, $R^{1a}$, $R^{1b}$ and $R^{1c}$ are each benzyl.

In embodiments, at least one of $R^{1a}$, $R^{1b}$ and $R^{1c}$ is 5-, 6-, 9- or 10-membered heteroaryl or 4- to 8-membered heterocycloalkyl. It may be that a single one of $R^{1a}$, $R^{1b}$ and $R^{1c}$ is 5-, 6-, 9- or 10-membered heteroaryl or 4- to 8-membered heterocycloalkyl. In embodiments, at least one of $R^{1a}$, $R^{1b}$ and $R^{1c}$ is 5-, 6-, 9- or 10-membered heteroaryl or 4- to 8-membered heterocycloalkyl, wherein said heteroaryl or heterocycloalkyl group comprises at least one nitrogen atom in the ring. It may be that a single one of $R^{1a}$, $R^{1b}$ and $R^{1c}$ is 5-, 6-, 9- or 10-membered heteroaryl or 4- to 8-membered heterocycloalkyl, wherein said heteroaryl or heterocycloalkyl group comprises at least one nitrogen atom in the ring. In embodiments, at least one of $R^{1a}$, $R^{1b}$ and $R^{1c}$ is 5- or 6-membered heteroaryl group, wherein said heteroaryl group comprises at least one nitrogen atom in the ring. It may be that a single one of $R^{1a}$, $R^{1b}$ and $R^{1c}$ is 5- or 6-membered heteroaryl group, wherein said heteroaryl group comprises at least one nitrogen atom in the ring. In these embodiments, it may be that any of $R^{1a}$, $R^{1b}$ and $R^{1c}$ that are not heteroaryl or heterocyclolkyl are phenyl, e.g. unsubstituted phenyl.

In embodiments, at least one of $R^{1a}$, $R^{1b}$ and $R^{1c}$ is 5-, 6-, 9- or 10-membered heteroaryl or 5- to 8-membered heterocycloalkyl. It may be that a single one of $R^{1a}$, $R^{1b}$ and $R^{1c}$ is 5-, 6-, 9- or 10-membered heteroaryl or 5- to 8-membered heterocycloalkyl. In embodiments, at least one of $R^{1a}$, $R^{1b}$ and $R^{1c}$ is 5-, 6-, 9- or 10-membered heteroaryl or 4- to 8-membered heterocycloalkyl, wherein said heteroaryl or heterocycloalkyl group comprises at least one nitrogen atom in the ring. It may be that a single one of $R^{1a}$, $R^{1b}$ and $R^{1c}$ is 5-, 6-, 9- or 10-membered heteroaryl or 5- to 8-membered heterocycloalkyl, wherein said heteroaryl or heterocycloalkyl group comprises at least one nitrogen atom in the ring. In embodiments, at least one of $R^{1a}$, $R^{1b}$ and $R^{1c}$ is 5- or 6-membered heteroaryl group, wherein said heteroaryl group comprises at least one nitrogen atom in the ring. It may be that a single one of $R^{1a}$, $R^{1b}$ and $R^{1c}$ is 5- or 6-membered heteroaryl group, wherein said heteroaryl group comprises at least one nitrogen atom in the ring. In these embodiments, it may be that any of $R^{1a}$, $R^{1b}$ and $R^{1c}$ that are not heteroaryl or heterocyclolkyl are phenyl, e.g. unsubstituted phenyl.

In embodiments, at least one of $R^{1a}$, $R^{1b}$ and $R^{1c}$ is $C_1$-$C_6$-alkyl (e.g. methyl). It may be that a single one of $R^{1a}$, $R^{1b}$ and $R^{1c}$ is $C_1$-$C_6$-alkyl (e.g. methyl). It may be that two or more of $R^{1a}$, $R^{1b}$ and $R^{1c}$ is $C_1$-$C_6$-alkyl (e.g. methyl). It may be that each of $R^{1a}$, $R^{1b}$ and $R^{1c}$ is $C_1$-$C_6$-alkyl (e.g. methyl). In these embodiments, it may be that any of $R^{1a}$, $R^{1b}$ and $R^{1c}$ that are not $C_1$-$C_6$-alkyl are phenyl, e.g. unsubstituted phenyl.

It may be that $R^{1a}$ and $R^{1b}$ are connected to each other via a bond or a group selected from —O—, $NR^{6a}$, and $C_1$-$C_3$-alkylene. It may be that $R^{1a}$ and $R^{1b}$ are connected to each other via a bond or a $C_1$-$C_3$-alkylene group. It may be that $R^{1a}$ and $R^{1b}$ are connected to each other via a bond. It may be that $R^{1a}$ and $R^{1b}$ are each phenyl and are connected to each other via a bond or a group selected from —O—, $NR^{6a}$, and $C_1$-$C_3$-alkylene. It may be that $R^{1a}$ and $R^{1b}$ are each phenyl and are connected to each other via a bond or a $C_1$-$C_3$-alkylene group. It may be that $R^{1a}$ and $R^{1b}$ are each phenyl and are connected to each other via a bond.

It may be that $R^{1a}$ and $R^{1b}$ are not connected to each other via a bond or a group selected from —O—, $NR^{6a}$, and $C_1$-$C_3$-alkylene.

In embodiments, $-^{+}PR^{1a}R^{1b}R^{1c}$ is selected from:

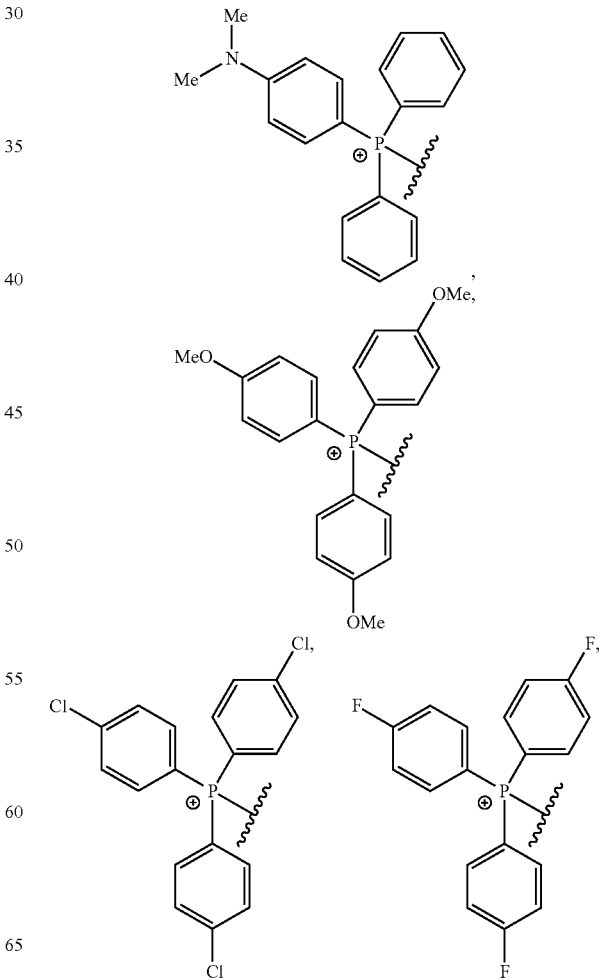

-continued
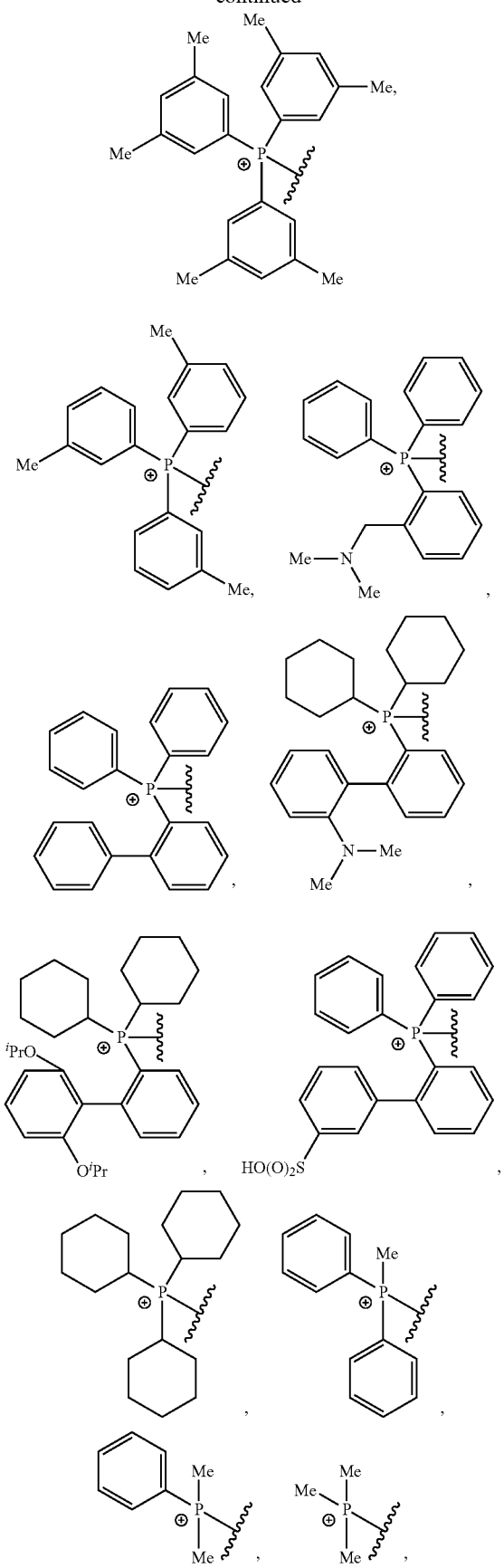
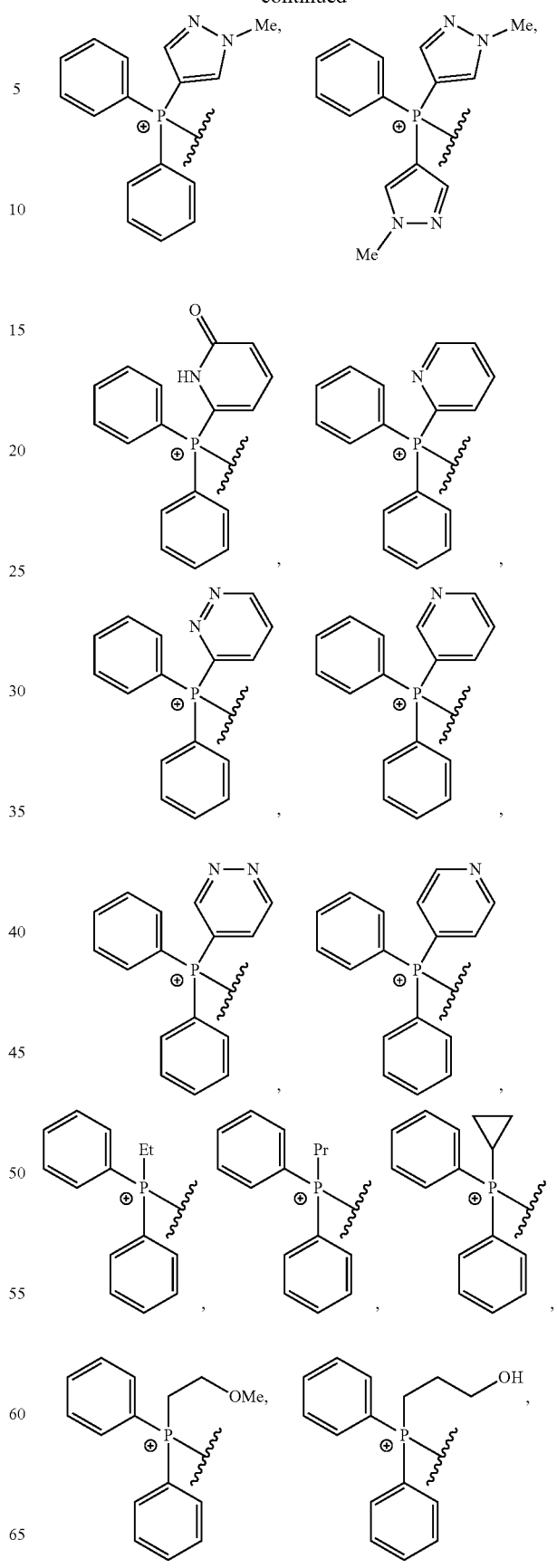

-continued

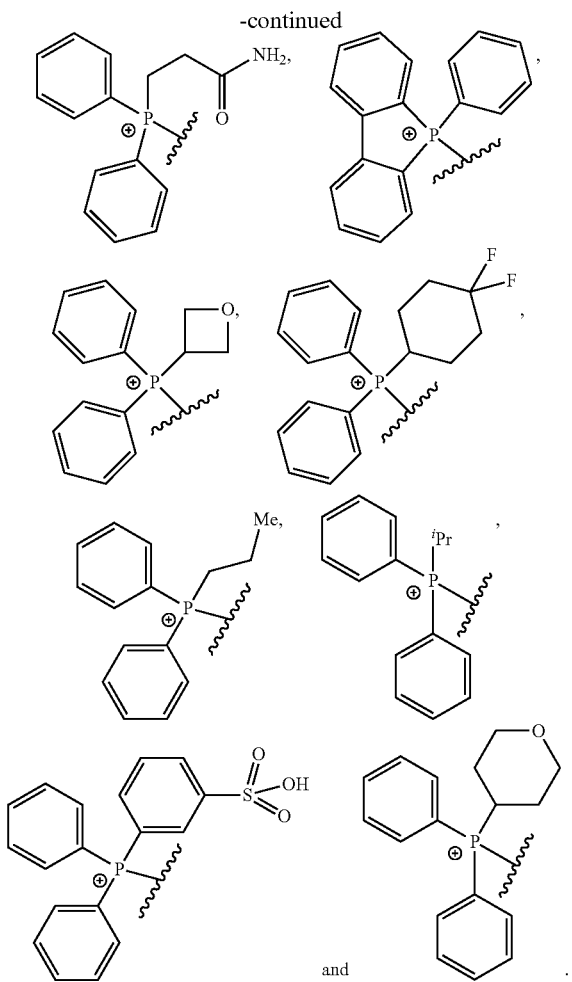

and

In embodiments $R^{2a}$ and $R^{2b}$ are each independently selected from H and methyl.

In embodiments, $L^1$ is absent.

In embodiments, $L^1$ is $CR^{2a}R^{2b}$, e.g. —$CH_2$—.

In embodiments, $L^1$ is absent or —$CH_2$—.

In embodiments, $L^2$ is —$NR^{3a}$, —C(O)—, —C(O)NR^{3b}$— or —$NR^{3b}C(O)$—. Preferably, $L^2$ is —C(O)NR^{3b}$— or —$NR^{3b}C(O)$—. In embodiments $R^{3a}$ and $R^{3b}$ are each independently at each occurrence selected from H and methyl. In embodiments $R^{3b}$ is H. Accordingly, in embodiments $L^2$ may be —C(O)NR^{3b}$—, for example C(O)NH—.

In embodiments -$L^2$-$L^1$- represents —C(O)NR^{3b}$—, e.g. —C(O)NH—.

In embodiments -$L^2$-$L^1$- represents —C(O)NR^{3b}CR^{2a}R^{2b}$—, e.g. —C(O)NHCH_2$—.

In a preferred embodiment the ion of formula (I) may be an ion according to formula (II) wherein $R^Z$ is H, $R^X$ is H, $R^Y$ is $CH_3$, and $R^W$ is OH.

In a preferred embodiment the ion of formula (I) may be an ion according to formula (III) wherein $R^Z$ is H, $R^X$ is H, $R^Y$ is $CH_3$, and $R^W$ is OH.

In a preferred embodiment the ion of formula (I) may be an ion according to formula (IIa) wherein $R^Z$ is H, $R^X$ is H, $R^Y$ is $CH_3$, and $R^W$ is OH.

In a preferred embodiment the ion of formula (I) may be an ion according to formula (IIIa) wherein $R^Z$ is H, $R^X$ is H, $R^Y$ is $CH_3$, and $R^W$ is OH.

In a preferred embodiment the ion of formula (I) may be an ion according to formula (IIb) wherein $R^Z$ is H, $R^X$ is H, $R^Y$ is $CH_3$, and $R^W$ is OH.

In a preferred embodiment the ion of formula (I) may be an ion according to formula (IIIb) wherein $R^Z$ is H, $R^X$ is H, $R^Y$ is $CH_3$, and $R^W$ is OH.

In embodiments, -($L^5$-$L^4$-)$_n$-$L^3$- is —$(CR^{4a}R^{4b})_o$-$L^4$-$(CR^{4c}R^{4d})_p$—, —$(CR^{4a}R^{4b})_j$-$L^4$-$(CR^{4c}R^{4d})_k$—, —$(CH_2)_q$-$L^4$-[O—$(CH_2)_r]_{1-3}$—$(CH_2)_s$—, —$(CH_2)_q$—[O—$(CH_2)_r]_{1-3}$-$L^4$-$(CH_2)_s$—, —$(CH_2)_q$-$L^4$-[$(CH_2)_r$—O]$_{1-3}$—$(CH_2)_s$— or —$(CH_2)_q$—[$(CH_2)_r$—O]$_{1-3}$-$L^4$-$(CH_2)_s$—; wherein o is selected from 3 to 10; p is selected from 1 to 3; j is selected from 1 to 3; k is 3 to 10; q and s are each independently selected from 0 to 3; and r is selected from 1 to 3.

In embodiments $R^{4a}$ and $R^{4b}$ are each independently at each occurrence selected from: H, $C_1$-$C_6$-alkynyl, $C_2$-$C_6$-alkenyl, $C_1$-$C_6$-haloalkyl, $OR^6$, $NR^7R^8$, C(O)OR^7$, C(O)NR^7R^8$, halo, cyano, nitro, C(O)R^7$, S(O)_2OR^7$, S(O)_2R^7$ and S(O)_2NR^7R^8$; and $R^{4c}$ and $R^{4d}$ are each independently at each occurrence selected from: H, $C_1$-$C_6$-alkyl, $C_1$-$C_6$-haloalkyl, $NR^7R^8$, $OR^6$, and halo.

In embodiments $R^{4a}$ and $R^{4b}$ are each independently at each occurrence selected from: H, $C_1$-$C_6$-alkyl, $C_2$-$C_6$-alkynyl, $C_2$-$C_6$-alkenyl, $C_1$-$C_6$-haloalkyl, $OR^6$, $SR^7$, $NR^7R^8$, C(O)OR^7$, C(O)NR^7R^8$, halo, cyano, nitro, C(O)R^7$, S(O)_2OR^7$, S(O)_2R^7$ and S(O)_2NR^7R^8$; and $R^{4c}$ and $R^{4d}$ are each independently at each occurrence selected from: H, $C_1$-$C_6$-alkyl, $C_1$-$C_6$-haloalkyl, $NR^7R^8$, $OR^6$, and halo.

In embodiments, -($L^5$-$L^4$-)$_n$-$L^3$- is —$(CR^{4a}R^{4b})_o$-$L^4$-$(CR^{4c}R^{4d})_p$—, —$(CR^{4a}R^{4b})_j$-$L^4$-$(CR^{4c}R^{4d})_k$—, —$(CH_2)_q$-$L^4$-[O—$(CH_2)_r]_{1-3}$—$(CH_2)_s$—, —$(CH_2)_q$—[O—$(CH_2)_r]_{1-3}$-$L^4$-$(CH_2)_s$—, —$(CH_2)_q$-$L^4$-[$(CH_2)_r$—O]$_{1-3}$—$(CH_2)_s$— or —$(CH_2)_q$—[$(CH_2)_r$—O]$_{1-3}$-$L^4$-$(CH_2)_s$—; wherein o is selected from 3 to 10; p is selected from 1 to 3; j is selected from 1 to 3; k is 3 to 10; q and s are each independently selected from 0 to 3; and r is selected from 1 to 3; $R^{4a}$ and $R^{4b}$ are each independently at each occurrence selected from: H, $C_1$-$C_6$-alkyl, $C_2$-$C_6$-alkynyl, $C_2$-$C_6$-alkenyl, $C_1$-$C_6$-haloalkyl, $OR^6$, $SR^7$, $NR^7R^8$, C(O)OR^7$, C(O)NR^7R^8$, halo, cyano, nitro, C(O)R^7$, S(O)_2OR^7$, S(O)_2R^7$ and S(O)_2NR^7R^8$; and $R^{4c}$ and $R^{4d}$ are each independently at each occurrence selected from: H, $C_1$-$C_6$-alkyl, $C_1$-$C_6$-haloalkyl, $NR^7R^8$, $OR^6$, and halo.

In embodiments, -($L^5$-$L^4$-)$_n$-$L^3$- is —$(CR^{4a}R^{4b})_o$-$L^4$-$(CR^{4c}R^{4d})_p$—, —$(CR^{4a}R^{4b})_j$-$L^4$-$(CR^{4c}R^{4d})_k$—, —$(CH_2)_q$-$L^4$-[O—$(CH_2)_r]_{1-3}$—$(CH_2)_s$—, —$(CH_2)_q$—[O—$(CH_2)_r]_{1-3}$-$L^4$-$(CH_2)_s$—, —$(CH_2)_q$-$L^4$-[$(CH_2)_r$—O]$_{1-3}$—$(CH_2)_s$— or —$(CH_2)_q$—[$(CH_2)_r$—O]$_{1-3}$-$L^4$-$(CH_2)_s$—; wherein o is selected from 3 to 10; p is selected from 1 to 3; j is selected from 1 to 3; k is 3 to 10; q and s are each independently selected from 0 to 3; and r is selected from 1 to 3; $R^{4a}$ and $R^{4b}$ are each independently at each occurrence selected from: H, $C_1$-$C_6$-alkyl, $C_2$-$C_6$-alkynyl, $C_2$-$C_6$-alkenyl, $C_1$-$C_6$-haloalkyl, $OR^6$, $SR^7$, $NR^7R^8$, C(O)OR^7$, C(O)NR^7R^7$, halo, cyano, nitro, C(O)R^7$, S(O)_2OR^7$, S(O)_2R^7$ and S(O)_2NR^7R^8$; and $R^{4c}$ and $R^{4d}$ are each independently at each occurrence selected from: H, $C_1$-$C_6$-alkyl, $C_1$-$C_6$-haloalkyl, $NR^7R^8$, $OR^6$, and halo.

In embodiments r is 2.

In embodiments, -($L^5$-$L^4$-)$_n$-$L^3$- is —$(CR^{4a}R^{4b})_o$-$L^4$-$(CR^{4c}R^{4d})_p$—, or —$(CR^{4a}R^{4b})_j$-$L^4$-$(CR^{4c}R^{4d})_k$—; wherein o is selected from 3 to 10; p is selected from 1 to 3; j is selected from 1 to 3; k is 3 to 10; wherein $R^{4a}$ and $R^{4b}$ are each independently at each occurrence selected from: H, $C_1$-$C_6$-alkyl, $C_1$-$C_6$-haloalkyl, $OR^6$, and $NR^7R^8$; and $R^{4c}$ and $R^{4d}$ are each independently at each occurrence selected from: H and methyl.

In embodiments, -($L^5$-$L^4$-)$_n$-$L^3$- is —$(CR^{4a}R^{4b})_o$-$L^4$-$(CR^{4c}R^{4d})_p$—, wherein o is selected from 3 to 10; p is selected from 1 to 3; wherein $R^{4a}$ and $R^{4b}$ are each independently at each occurrence selected from: H, $C_1$-$C_6$-alkyl, $C_1$-$C_6$-haloalkyl, $OR^6$, and $NR^7R^8$; and $R^{4c}$ and $R^{4d}$ are each independently at each occurrence selected from: H and methyl.

In embodiments $L^1$, $L^2$, $L^3$, $L^4$ and $L^5$ together form a linker and n, $L^1$, $L^2$, $L^3$, $L^4$ and $L^5$ are selected such that length of the linker is from 8 to 14 atoms.

In embodiments -$L^4$- at each occurrence is absent or is selected from: —O—, —S—, $NR^{3a}$—, —C(O)—, —OC(O)—, —C(O)O—, —$NR^{3b}$C(O)—, —C(O)$NR^{3b}$, $NR^{3b}$S(O)$_2$—, —S(O)$_2NR^{3b}$—, —OC(O)$NR^{3b}$—, —$NR^{3b}$C(O)O—, $NR^{3b}$C(O)$NR^{3b}$, —$CR^5$=$CR^5$— and —C≡C—.

In embodiments, $L^4$ is at each occurrence absent or is selected from —C(O)$NR^{3b}$— and —$NR^{3b}$C(O)—.

In embodiments, $L^4$ is at each occurrence absent.

In embodiments, $L^4$ is at each occurrence C(O)$NR^{3b}$.

In embodiments, $L^4$ is at each occurrence $NR^{3b}$C(O).

In a preferred embodiment the ion of formula (I) may be an ion according to formula (IV) wherein $R^Z$ is H, $R^X$ is H, $R^Y$ is $CH_3$, and $R^W$ is OH.

In a preferred embodiment the ion of formula (I) may be an ion according to formula (V) wherein $R^Z$ is H, $R^X$ is H, $R^Y$ is $CH_3$, and $R^W$ is OH.

In a preferred embodiment the ion of formula (I) may be an ion according to formula (IVa)) wherein $R^Z$ is H, $R^X$ is H, $R^Y$ is $CH_3$, and $R^W$ is OH.

In a preferred embodiment the ion of formula (I) may be an ion according to formula (IVb) wherein $R^Z$ is H, $R^X$ is H, $R^Y$ is $CH_3$, and $R^W$ is OH.

In a preferred embodiment the ion of formula (I) may be an ion according to formula (Va) wherein $R^Z$ is H, $R^X$ is H, $R^Y$ is $CH_3$, and $R^W$ is OH.

In a preferred embodiment the ion of formula (I) may be an ion according to formula (Vb) wherein $R^Z$ is H, $R^X$ is H, $R^Y$ is $CH_3$, and $R^W$ is OH.

In embodiments -(-$L^5$-$L^4$-)$_n$-$L^3$-$L^2$-$L^1$- represents —$(CH_2)_{11}$C(O)NH—, —$(CH_2)_{10}$C(O)NH—, —$(CH_2)_9$C(O)NH—, —$(CH_2)_8$C(O)NH—, —$(CH_2)_7$C(O)NH, —$(CH_2)_9$C(O)NHCH$_2$C(O)NH—, —$(CH_2)_8$C(O)NHCH$_2$C(O)NH—, —$(CH_2)_7$C(O)NHCH$_2$C(O)NH—, —$(CH_2)_6$C(O)NHCH$_2$C(O)NH—, —$(CH_2)_5$C(O)NHCH$_2$C(O)NH—, —$(CH_2)_4$C(O)NHCH$_2$C(O)NH—, $(CH_2)_3$C(O)NHCH$_2$C(O)NH—, —$(CH_2)_7$C(O)NH$(CH_2)_2$C(O)NH—, —$(CH_2)_8$C(O)NH$(CH_2)_2$C(O)NH—, —$(CH_2)_9$C(O)NH$(CH_2)_2$C(O)NH—, —$(CH_2)_6$C(O)NH$(CH_2)_2$C(O)NH—, —$(CH_2)_5$C(O)NH$(CH_2)_2$C(O)NH—, —$(CH_2)_4$C(O)NH$(CH_2)_2$C(O)NH—, —$(CH_2)_3$C(O)NH$(CH_2)_2$C(O)NH—, —$(CH_2)_9$C(O)NHCH$_2$—, —$(CH_2)_8$C(O)NHCH$_2$—, —$(CH_2)_7$C(O)NHCH$_2$—, —$(CH_2)_6$C(O)NHCH$_2$—, —$(CH_2)_5$C(O)NHCH$_2$— and —$(CH_2)_4$C(O)NHCH$_2$—.

In embodiments -($L^5$-$L^4$-)$_n$-$L^3$-$L^2$-$L^1$- represents —$(CH_2)_{11}$C(O)NH—, —$(CH_2)_{10}$C(O)NH—, —$(CH_2)_9$C(O)NH—, —$(CH_2)_8$C(O)NH—, and —$(CH_2)_7$C(O)NH.

In embodiments -(-$L^5$-$L^4$-)$_n$-$L^3$-$L^2$-$L^1$- represents —$(CH_2)_9$C(O)NHCH$_2$C(O)NH—, —$(CH_2)_8$C(O)NHCH$_2$C(O)NH—, —$(CH_2)_7$C(O)NHCH$_2$C(O)NH—, —$(CH_2)_6$C(O)NHCH$_2$C(O)NH—, —$(CH_2)_5$C(O)NHCH$_2$C(O)NH—, —$(CH_2)_4$C(O)NHCH$_2$C(O)NH—, $(CH_2)_3$C(O)NHCH$_2$C(O)NH—.

In embodiments -(-$L^5$-$L^4$-)$_n$-$L^3$-$L^2$-$L^1$- represents —$(CH_2)_7$C(O)NH$(CH_2)_2$C(O)NH—, —$(CH_2)_8$C(O)NH$(CH_2)_2$C(O)NH—, —$(CH_2)_9$C(O)NH$(CH_2)_2$C(O)NH—, —$(CH_2)_6$C(O)NH$(CH_2)_2$C(O)NH—, —$(CH_2)_5$C(O)NH$(CH_2)_2$C(O)NH—, —$(CH_2)_4$C(O)NH$(CH_2)_2$C(O)NH—, and —$(CH_2)_3$C(O)NH$(CH_2)_2$C(O)NH—.

In embodiments -(-$L^5$-$L^4$-)$_n$-$L^3$-$L^2$-$L^1$- represents —$(CH_2)_9$C(O)NHCH$_2$—, —$(CH_2)_8$C(O)NHCH$_2$—, —$(CH_2)_7$C(O)NHCH$_2$—, —$(CH_2)_6$C(O)NHCH$_2$—, —$(CH_2)_5$C(O)NHCH$_2$— and —$(CH_2)_4$C(O)NHCH$_2$—.

In embodiments -(-$L^5$-$L^4$-)$_n$-$L^3$-$L^2$-$L^1$-represents —$(CH_2)_{11}$C(O)NH—, —$(CH_2)_7$C(O)NH, —$(CH_2)_{10}$C(O)NH, —$(CH_2)_9$C(O)NH, —$(CH_2)_7$C(O)NHCH$_2$C(O)NH—, —$(CH_2)_5$C(O)NHCH$_2$C(O)NH—, $(CH_2)_3$C(O)NHCH$_2$C(O)NH—, —$(CH_2)_7$C(O)NH$(CH_2)_2$C(O)NH—, —$(CH_2)_5$C(O)NH$(CH_2)_2$C(O)NH—, —$(CH_2)_4$C(O)NH$(CH_2)_2$C(O)NH—, —$(CH_2)_9$C(O)NHCH$_2$—, —$(CH_2)_5$C(O)NHCH$_2$— and —$(CH_2)_7$C(O)NHCH$_2$—.

In embodiments -(-$L^5$-$L^4$-)$_n$-$L^3$-$L^2$-$L^1$- is such that the length of the linker is 9, 10, 11, 12, 13, or 14 atoms in length.

In embodiments n is an integer selected from 0 or 1.

In embodiments, $R^{3a}$ is at any particular occurrence H. In embodiments, $R^{3a}$ is at each occurrence H.

In embodiments, $R^{3a}$ is at any particular occurrence $C_1$-$C_4$-alkyl, e.g. methyl. In embodiments, $R^{3a}$ is at each occurrence $C_1$-$C_4$-alkyl, e.g. methyl.

In embodiments, $R^{3b}$ is at any particular occurrence H. In embodiments, $R^{3b}$ is at each occurrence H.

In embodiments, $R^{3b}$ is at any particular occurrence $C_1$-$C_4$-alkyl, e.g. methyl. In embodiments, $R^{3b}$ is at each occurrence $C_1$-$C_4$-alkyl, e.g. methyl.

In embodiments, $R^5$ is at any particular occurrence H. In embodiments, $R^5$ is at each occurrence H.

In embodiments, $R^4$ is at any particular occurrence selected from $C_1$-$C_4$-alkyl, e.g. methyl. In embodiments, $R^4$ is at each occurrence selected from $C_1$-$C_4$-alkyl, e.g. methyl.

In embodiments, $L^3$ and $L^5$ are unsubstituted.

In embodiments, $R^4$ is at any particular occurrence $C_1$-$C_4$-alkyl, e.g. methyl. In embodiments, $R^4$ is at each occurrence $C_1$-$C_4$-alkyl, e.g. methyl.

In embodiments, $R^6$ is at any particular occurrence H. In embodiments, $R^6$ is at each occurrence H.

In embodiments, $R^6$ is at any particular occurrence $C_1$-$C_4$-alkyl, e.g. methyl. In embodiments, $R^6$ is at each occurrence $C_1$-$C_4$-alkyl, e.g. methyl.

In embodiments, $R^7$ is at any particular occurrence H. In embodiments, $R^7$ is at each occurrence H.

In embodiments, $R^7$ is at any particular occurrence $C_1$-$C_4$-alkyl, e.g. methyl. In embodiments, $R^7$ is at each occurrence $C_1$-$C_4$-alkyl, e.g. methyl.

In embodiments, $R^8$ is at any particular occurrence H. In embodiments, $R^8$ is at each occurrence H.

In embodiments, $R^8$ is at any particular occurrence $C_1$-$C_4$-alkyl, e.g. methyl. In embodiments, $R^8$ is at each occurrence $C_1$-$C_4$-alkyl, e.g. methyl.

In an embodiment, the ion according to formula (I) is selected from:

-continued
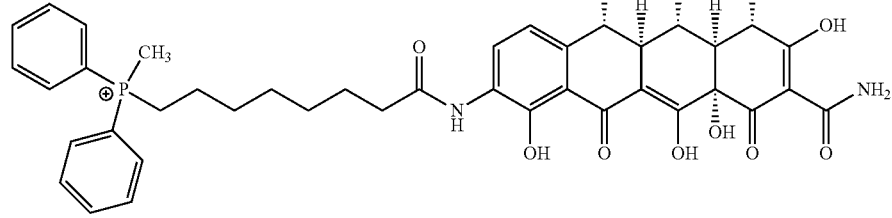
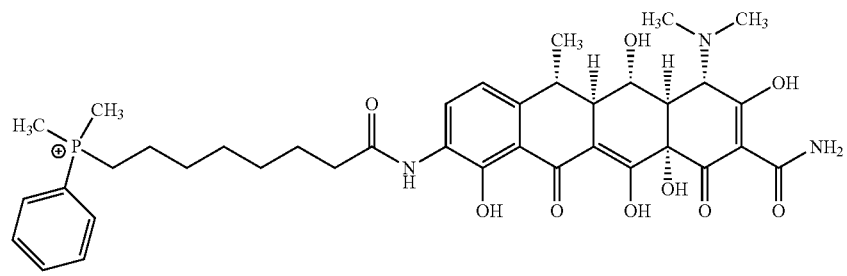
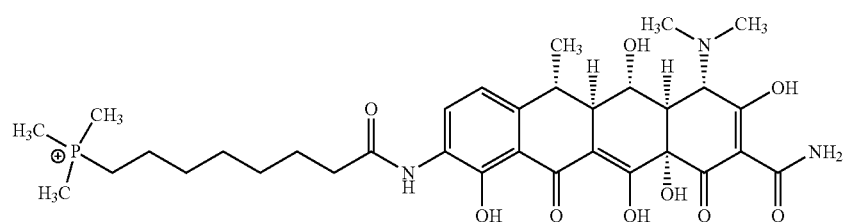
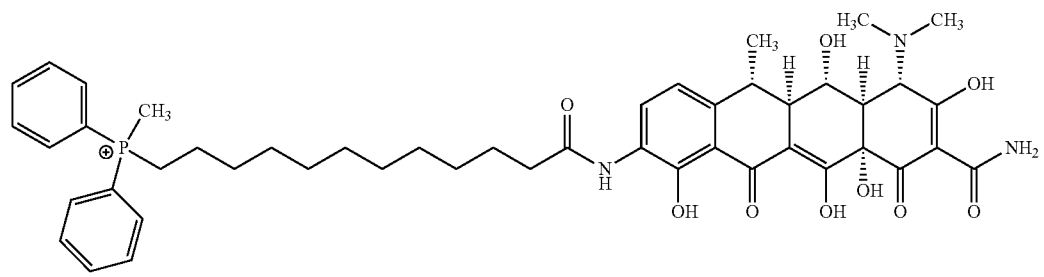
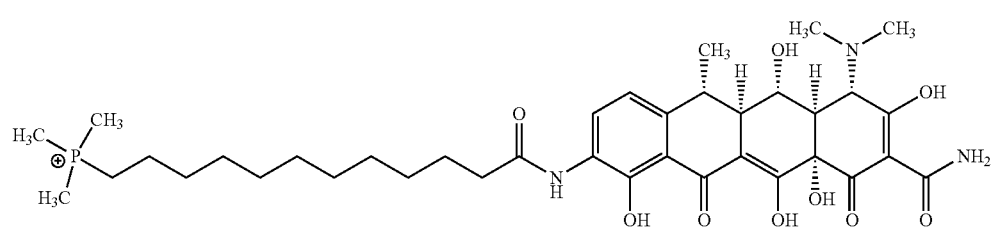
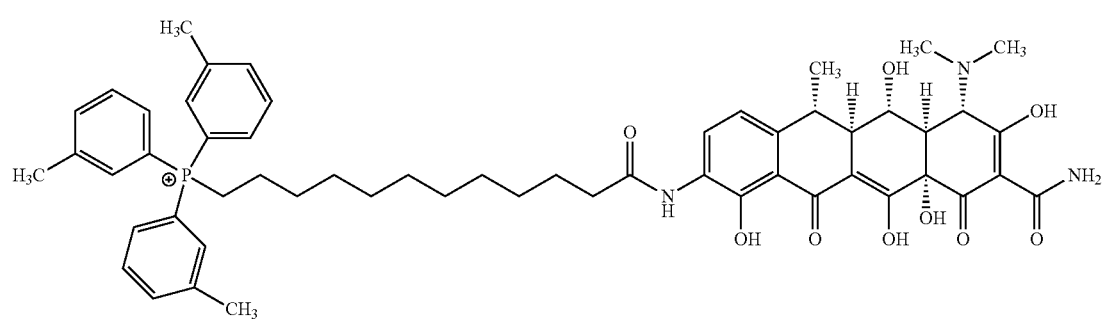

-continued
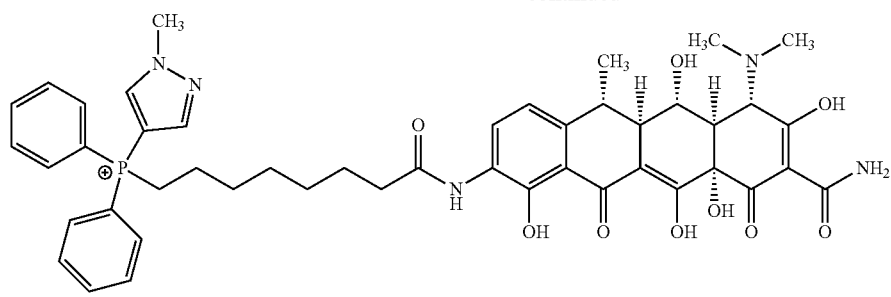
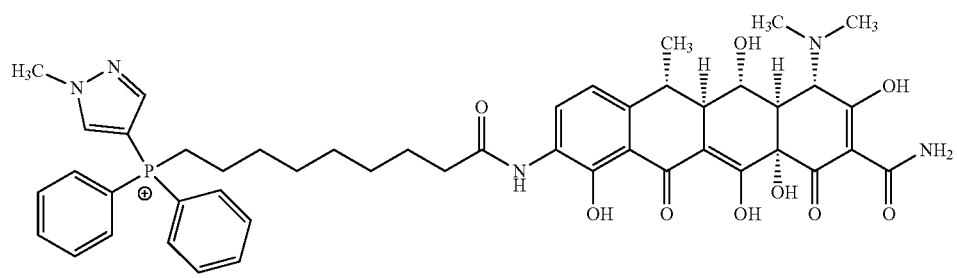
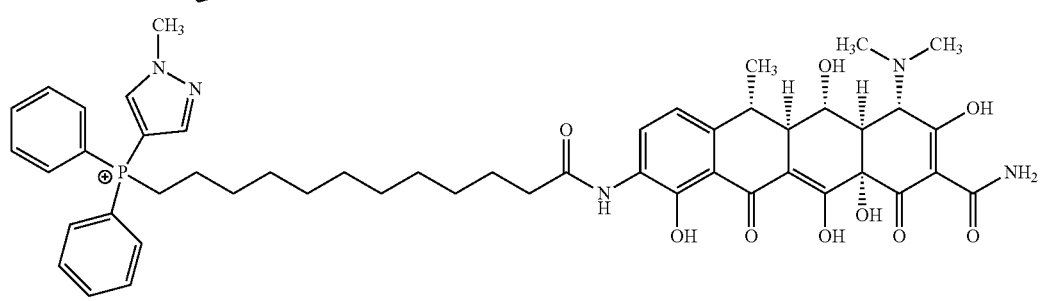
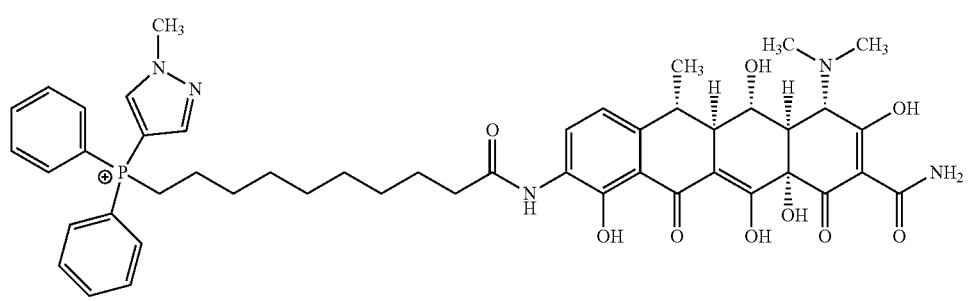
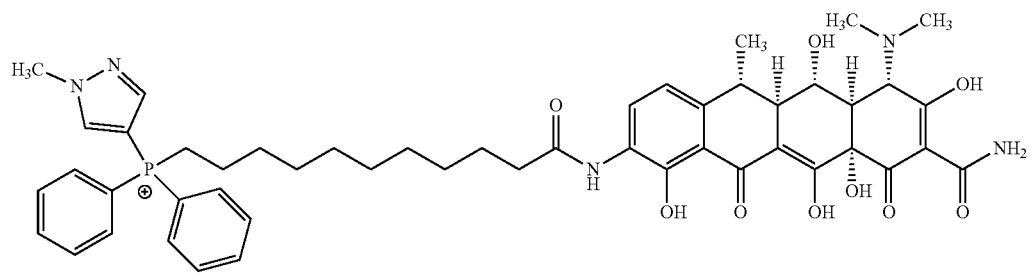
and
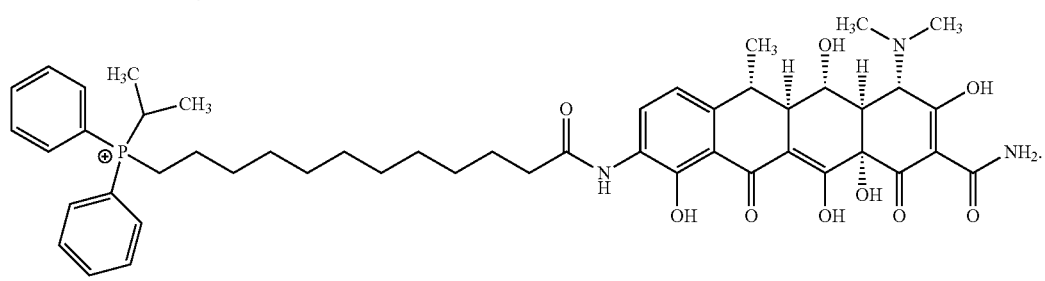

In an embodiment, the ion according to formula (I) is selected from:
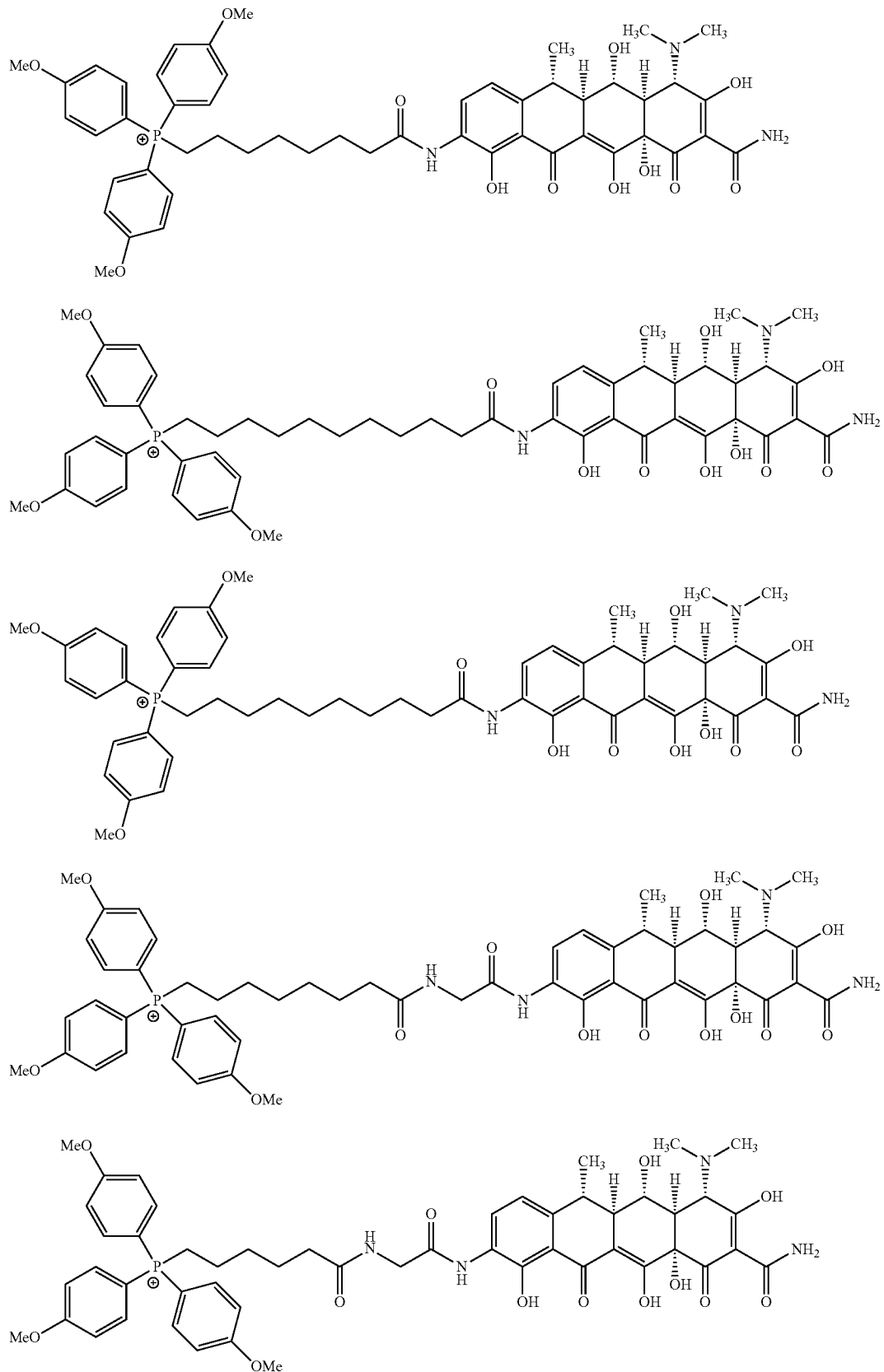

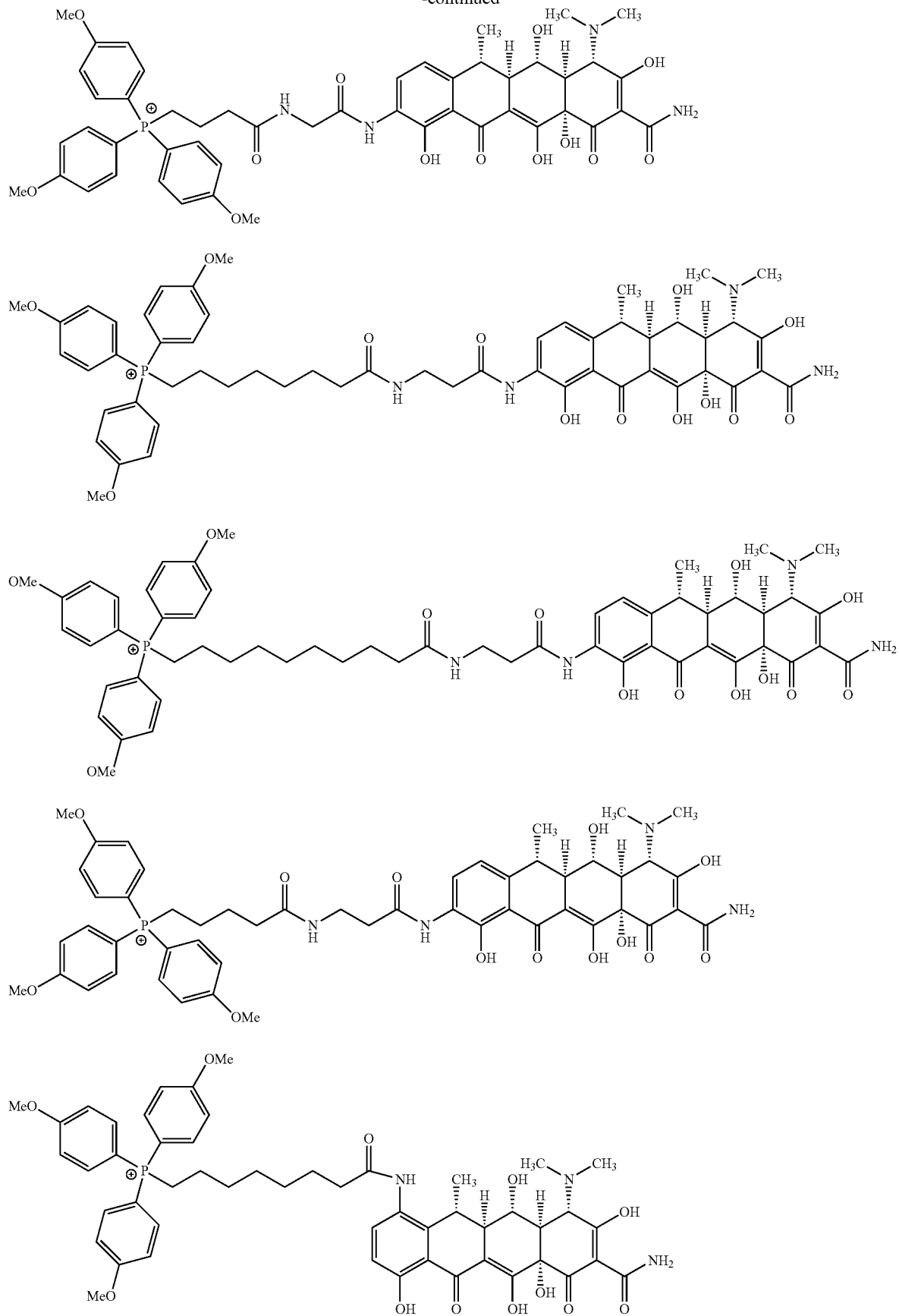

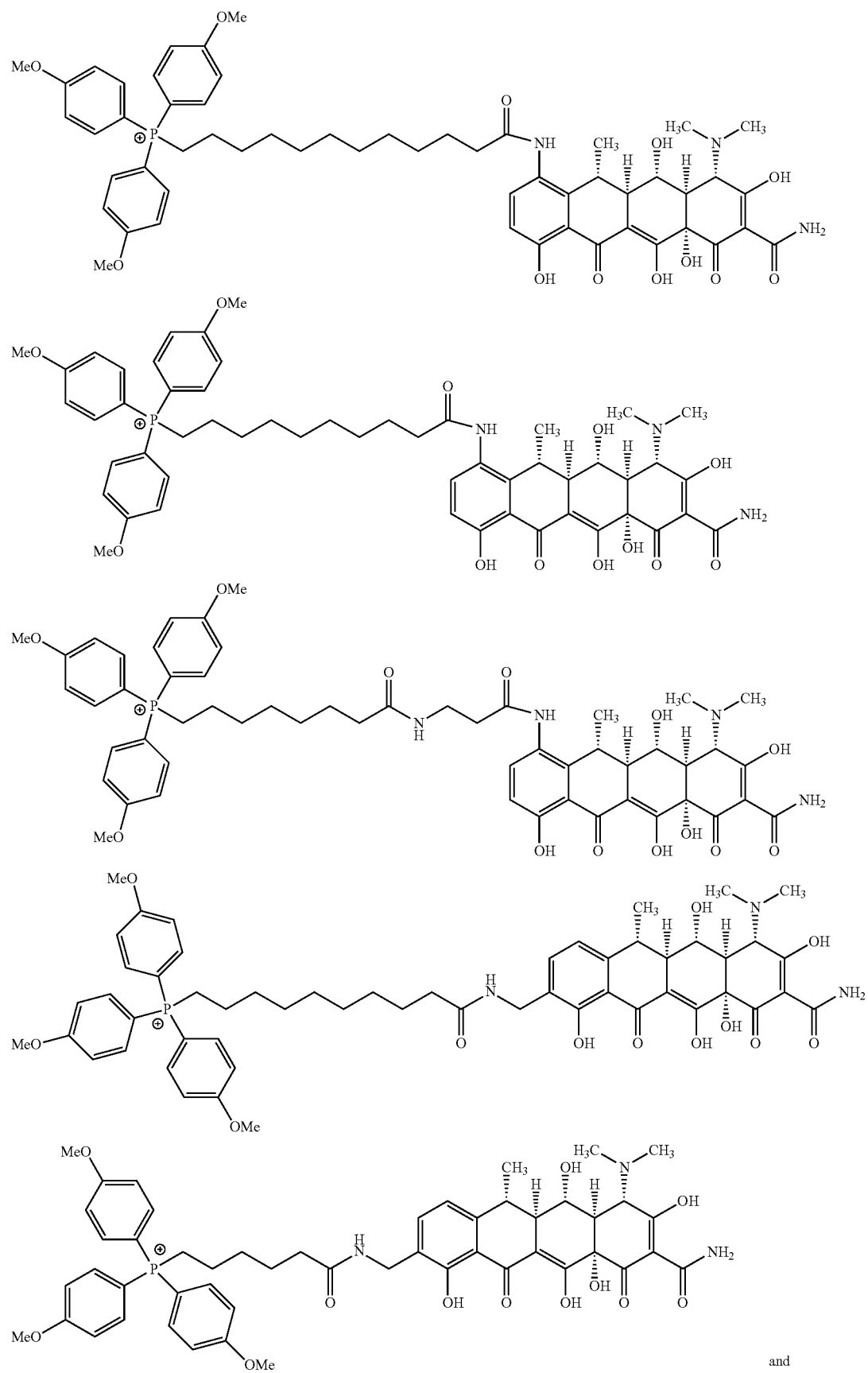

-continued
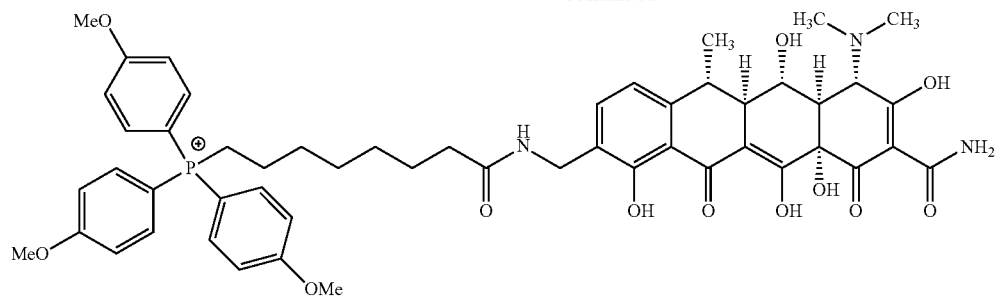
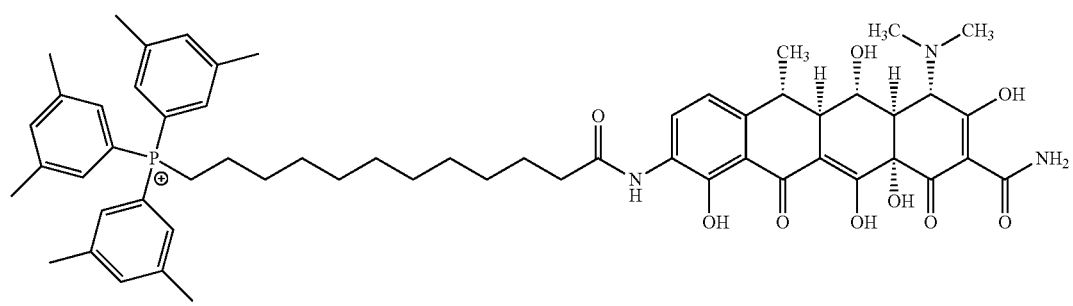
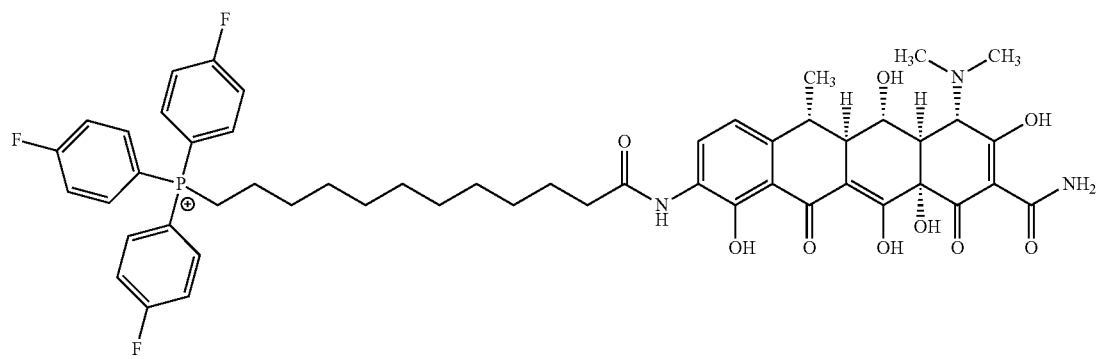
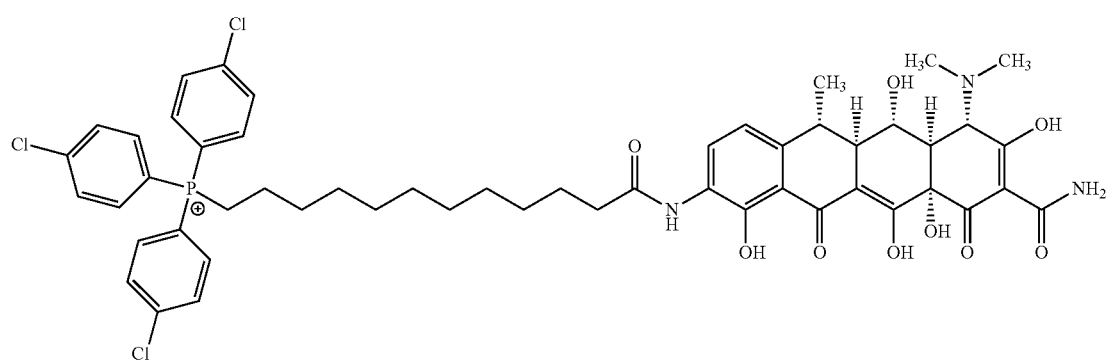
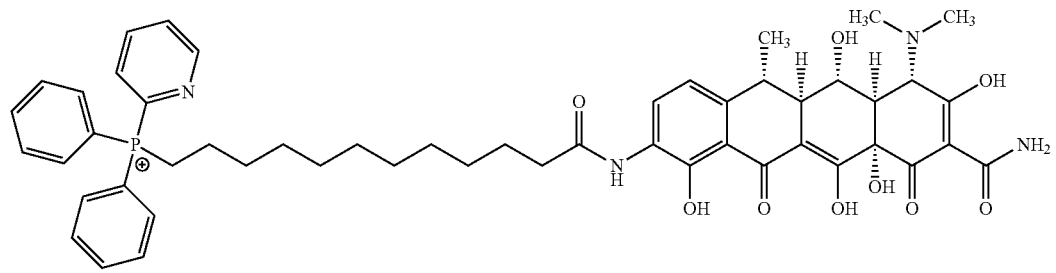

33
-continued
34
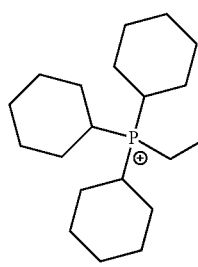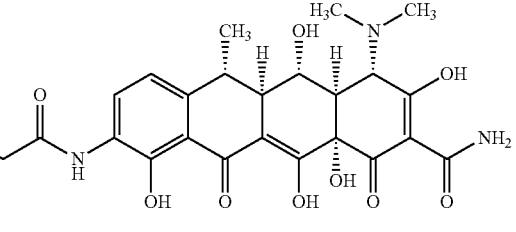
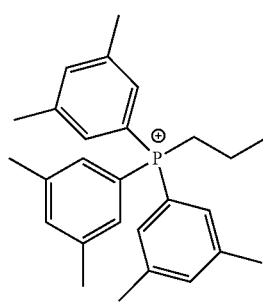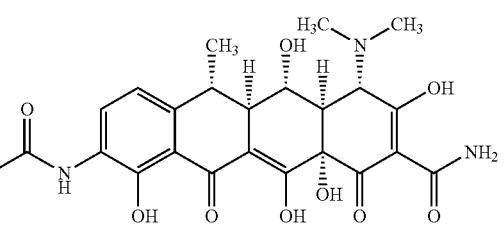
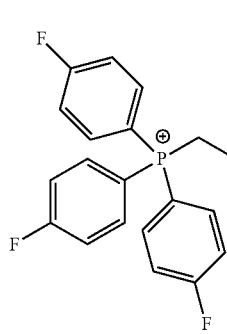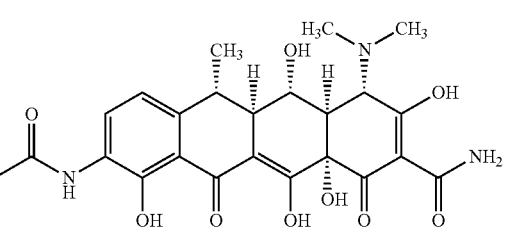
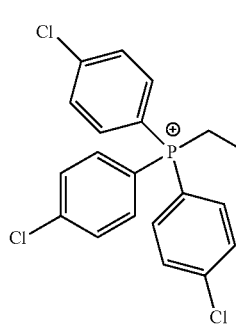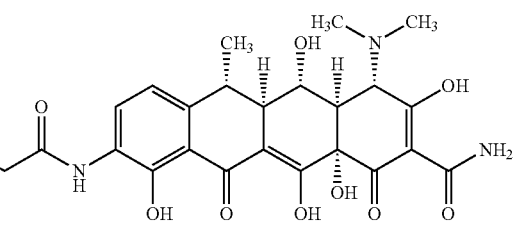
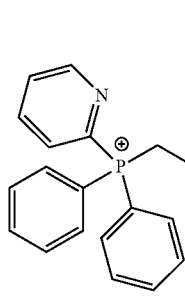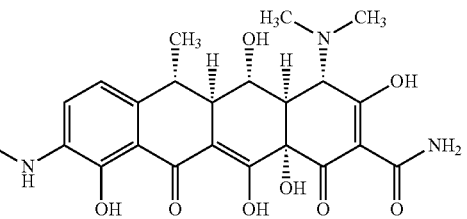

-continued
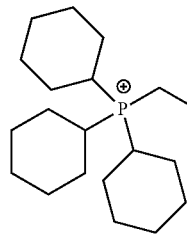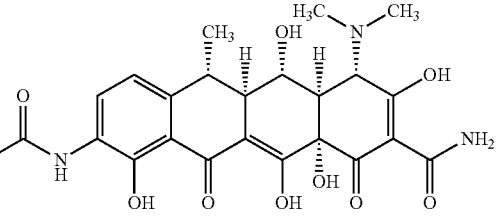
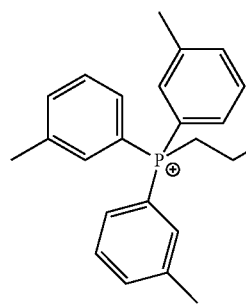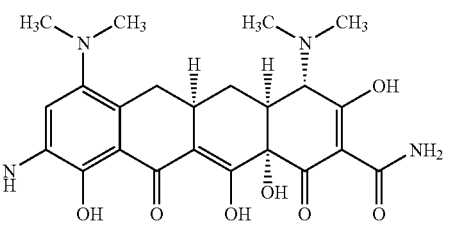
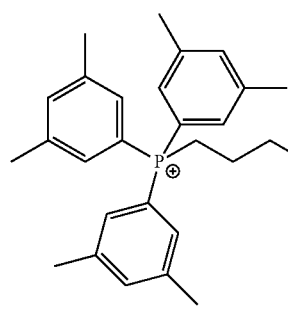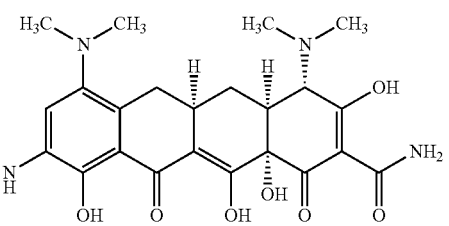
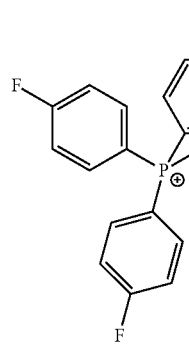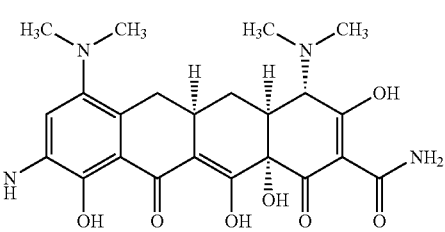
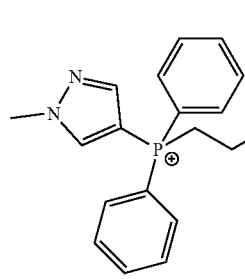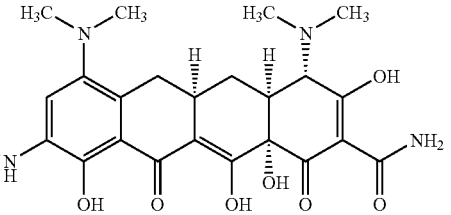

-continued
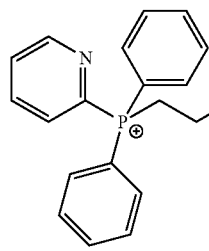 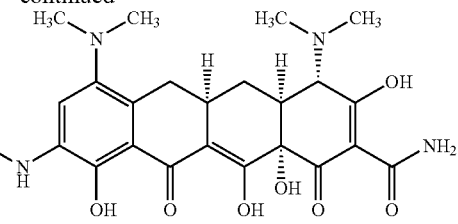
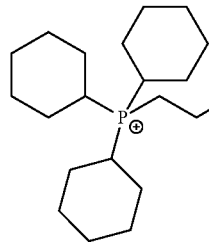 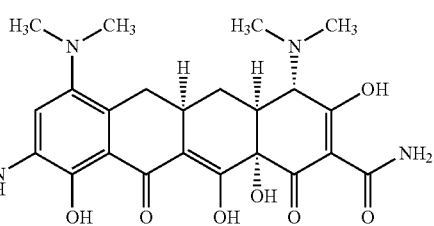
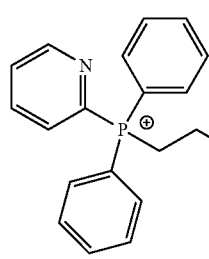 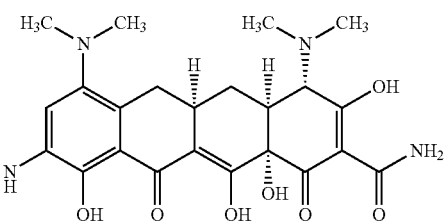
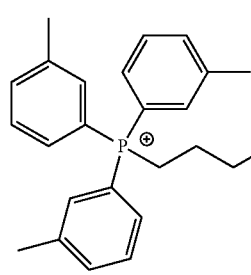 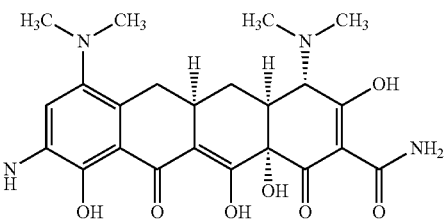
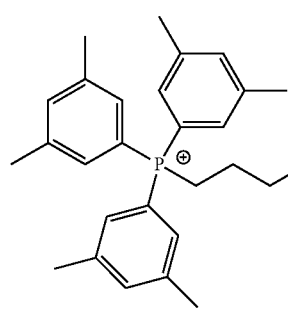 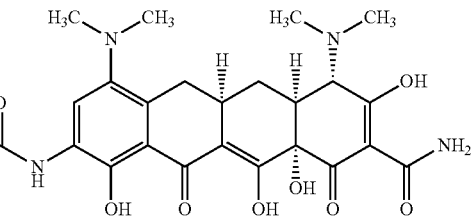

-continued

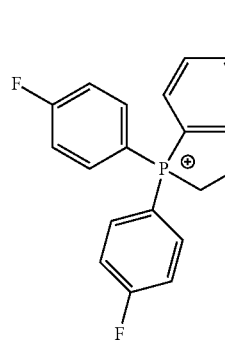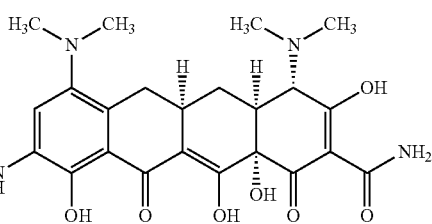

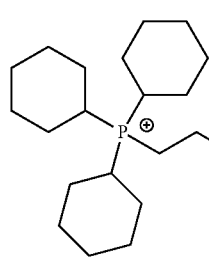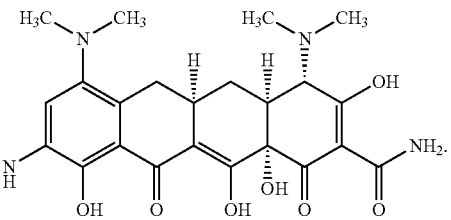

and

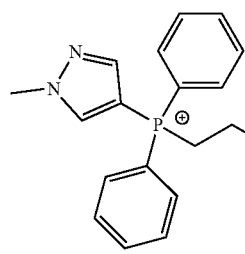

The cation of formula (I) will be associated with an anionic counter ion. For administration to a subject, the cation of formula (I) will be associated with a pharmaceutically acceptable anionic counterion. The first aspect of the invention also, therefore, provides a compound comprising the ion of formula (I) and a pharmaceutically acceptable anion. The anion may have a single negative charge. For example the anion may be selected from: halo (e.g. Cl, Br and I), $BF_4^-$, $PF_6^-$, $CF_3C(O)O^-$, $HC(O)O^-$, $HCO_3^-$, $(CF_3SO_2)_2N^-$, $(C_2F_5)_3PF_3^-$, $HSO_4^-$, $C_1$-$C_{15}$-alkylSO$_4^-$, $CH_3C(O)O^-$, $CF_3SO_3^-$, Tosyl-O$^-$, $C(CN)_3^-$, $N(CN)_2^-$ or the carboxylate anion of a proteinogenic amino acid. For the avoidance of doubt each anion listed in the preceding sentence possesses a single negative charge. The anion may have multiple negative charges, e.g. $PO_4^{3-}$ or $CO_3^{2-}$. The anion may be derived from a di- or tri-acid, e.g. glutamic acid, succinic acid, malic acid, citric acid, tartaric acid. It may be a mono-carboxylate of said di- or tri-acid. The remaining carboxylic acid groups may be in the form of protonated carboxylic acids, $C_1$-$C_{12}$-alkylesters, or they may likewise be carboxylate anions. Said carboxylate anions may each be accompanied by a pharmaceutically acceptable metal cation or by another cation of formula (I).

The anions associated with the cations of the invention can be quite labile. It may be therefore that the cation of the invention is present associated with two or more different anions. Ion exchange processes can be used to control the identity of the anion associated with the cation of the invention.

In embodiments the anion is Cl, Br, I, $PF_6^-$, $CF_3C(O)O^-$, or $HC(O)O^-$.

In an aspect of the invention, the compounds of the invention are for medical use.

In an aspect, the compounds of the first aspect of the invention are for use in the treatment of cancer. The compounds may be effective in treating cancer stem cells. The compounds may also be for use in reducing cell proliferation of abnormal cells, such as cancer cells.

In an embodiment, the compounds of the first aspect of the invention are for use in the treatment of solid tumours and other cancers, e.g. cancers classed as not being solid cancers. Amongst cancers that can be treated by the compounds of the invention are: leukaemia, lymphoma, sarcoma, or carcinoma.

In a further aspect of the invention, there is provided a method for the treatment of cancer, wherein the method comprises the administration of a therapeutically effective amount of a compound of the first aspect of the invention. The method may be effective in treating cancer stem cells. The method may also be for use in reducing cell proliferation of abnormal cells, such as cancer cells.

In an embodiment, the method is for the treatment of solid tumours and other cancers, e.g. cancers classed as not being solid cancers. Amongst cancers that can be treated by the methods of the invention are: leukaemia, lymphoma, sarcoma, or carcinoma.

The "treatment" of cancer may be taken to include prevention. Treatment also encompasses including any improvement of pathology, symptoms or prognosis that is achieved in respect of cancer in a subject receiving compounds of the invention. Treatment may be indicated by a partial improvement of such indications, or by a total improvement (e.g. the absence of cancer following medical use of the compounds of the invention).

The "prevention" of cancer may be taken as including the prevention of the formation of new tumours, including new primary tumours or new metastatic tumours. The prevention of cancer may also be taken as encompassing the prevention of the progression of cancer. In this context, prevention of development of cancer may be demonstrated by preventing an increase in the "stage" of a tumour (using an appropriate cancer staging method) that has been treated using the compounds of the invention. The prevention of increase in cancer stage may be compared to progression of an untreated tumour, or compared to the extent of progression that would be expected by a clinician in the event that the tumour was not treated.

The compounds of the first aspect of the invention may be for use in increasing cancer cell death or for decreasing cell proliferation by another mechanism, such as inhibiting cell replication. The compounds may be used for this purpose in vitro or in vivo.

The compounds of the invention may be for use in the modulation of cancer cells or other dysfunctional cells (such as tumour initiating cells, stem-like cancer cells, cancer stem cells, or a population of cells with stem cell-like features that exist in tumors and that give rise to the bulk of tumor cells with more differentiated phenotypes). Accordingly, there is provided a method of modulating cancer cells or other dysfunctional cells in vivo or in vitro by exposing the cancer cells or other dysfunctional cells to a compound of the invention. The compound may be exposed to the cancer cells or other dysfunctional cells in an effective amount, for example a therapeutically effective amount such as in the case of a method of treatment or an in vivo method.

In another aspect of the invention there is provided a pharmaceutical composition, wherein the composition comprises a compound of the invention and one or more pharmaceutically acceptable excipients.

In an embodiment, the pharmaceutical composition may be a combination product comprising one or more different pharmaceutically active agents. The one or more additional pharmaceutically active agents may be an anti-cancer agent described below. The one or more pharmaceutically active agents may independently be selected from a different therapeutic class, e.g. antibiotic, anti-viral, anti-emetic, pain management, etc.

The present invention also contemplates the subject matter contained in the following numbered clauses:

1. A compound comprising an ion of formula (I) or a pharmaceutically acceptable salt thereof:

(I)

wherein
$R^W$ is H or OH;
$R^X$ is H;
$R^Y$ is H, $C_1$-$C_6$-alkyl or $C_1$-$C_6$-haloalkyl;
$R^Z$ is H, $NR^{Z1}R^{Z2}$, $C_1$-$C_6$-haloalkyl, or halo, wherein $R^{Z1}$ and $R^{Z2}$ are both independently selected from H or $C_1$-$C_6$-alkyl;

-$L^1$- is absent or is —$CR^{2a}R^{2b}$—;
-$L^2$- is absent or is independently selected from —O—, —S—, —$NR^{3a}$—, —C(O)$NR^{3b}$—, —C(O)—, —OC(O)—, —$NR^{3b}$C(O)—, $NR^5S(O)_2$—, —OC(O)$NR^{3b}$—, —$NR^{3b}$C(O)O— and —$NR^{3b}$C(O)$NR^{3c}$;
-$L^3$- and -$L^5$- are each independently at each occurrence selected from —$C_1$-$C_4$-alkylene-, each alkylene group being unsubstituted or substituted with from 1 to 10 independently selected $R^4$ groups; provided that any -$L^3$- or -$L^5$- group that is attached at each end to an atom selected from oxygen, nitrogen, sulphur or phosphorous is —$C_2$-$C_4$-alkylene-;
-$L^4$- is independently at each occurrence either absent or is selected from: —O—, —S—, —$NR^{3a}$—, —C(O)—, —OC(O)—, —C(O)O—, —$SO_2$—, —S(O)—, —$NR^{3b}$C(O)—, —C(O)$NR^{3b}$, $NR^{3b}S(O)_2$—, —$S(O)_2NR^{3b}$—, —OC(O)$NR^{3b}$—, —$NR^{3b}$C(O)O—, $NR^{3b}$C(O)$NR^{3c}$, —$CR^{5a}$=$CR^{5b}$— and —C≡C—;

n is an integer selected from 0, 1, 2, 3, 4 and 5;
wherein $L^1$, $L^2$, $L^3$ $L^4$ and $L^5$ together form a linker and $L^1$, $L^2$, $L^3$ $L^4$ and $L^5$ are selected such that length of the linker is from 3 to 16 atoms;
$R^{1a}$, $R^{1b}$ and $R^{1c}$ are each independently selected from phenyl, biphenyl, naphthyl, 5-, 6-, 9- or 10-membered heteroaryl, $C_3$ to $C_8$-cycloalkyl, $C_1$-$C_8$-alkyl and 5- to 8-membered heterocycloalkyl; wherein said phenyl, biphenyl, naphthyl, 5-, 6-, 9- or 10-membered heteroaryl is optionally substituted with from 1 to 5 independently selected $R^{1d}$ groups; and wherein said $C_3$ to $C_8$-cycloalkyl, $C_1$-$C_8$-alkyl and 5- to 8-membered heterocycloalkyl is optionally substituted with from 1 to 5 independently selected $R^{1e}$ groups; provided that $R^{1a}$, $R^{1b}$ and $R^{1c}$ are not each unsubstituted phenyl;
$R^{1d}$ is independently at each occurrence selected from: $C_1$-$C_6$-alkyl, $C_2$-$C_6$-alkynyl, $C_2$-$C_6$-alkenyl, $C_1$-$C_6$-haloalkyl, $C_3$-$C_6$-cycloalkyl, 5- to 8-membered heterocycloalkyl, 5-, 6-, 9- or 10-membered heteroaryl, phenyl, $OR^6$, $SR^7$, $NR^7R^8$, $C(O)OR^7$, $C(O)NR^7R^{7A}$, halo, cyano, nitro, $C(O)R^7$, $S(O)_2OR^7$, $S(O)R^7$, $S(O)_2R^7$ and $S(O)_2NR^7R^{7A}$;
$R^{1e}$ is independently at each occurrence selected from: oxo, $C_1$-$C_6$-alkyl, $C_2$-$C_6$-alkynyl, $C_2$-$C_6$-alkenyl, $C_1$-$C_6$-haloalkyl, $C_3$-$C_6$-cycloalkyl, 5- to 8-membered heterocycloalkyl, 5-, 6-, 9- or 10-membered heteroaryl, phenyl, $OR^6$, $SR^7$, $NR^7R^8$, $C(O)OR^7$, $C(O)NR^7R^{7A}$, halo, cyano, nitro, $C(O)R^7$, $S(O)_2OR^7$, $S(O)R^7$, $S(O)_2R^7$, $S(O)_2NR^7R^{7A}$, $OC(O)NR^7R^{7A}$ and $NR^7C(O)OR^6$;
$R^{2a}$ and $R^{2b}$ are each independently selected from H and $C_1$-$C_4$-alkyl;
$R^{3a}$, is independently at each occurrence selected from H, $C_1$-$C_6$-alkyl, —C(O)H, —C(O)—$C_1$-$C_6$-alkyl and —$S(O)_2$—$C_1$-$C_6$-alkyl
$R^{3b}$ and $R^{3c}$ are each independently at each occurrence selected from H and $C_1$-$C_6$-alkyl;
$R^4$ is independently at each occurrence selected from: $C_1$-$C_6$-alkyl, $C_2$-$C_6$-alkynyl, $C_2$-$C_6$-alkenyl, $C_1$-$C_6$-haloalkyl, $OR^6$, $SR^7$, $NR^7R^8$, $C(O)OR^7$, $C(O)NR^7R^{7A}$, halo, cyano, nitro, $C(O)R^7$, $S(O)_2OR^7$, $S(O)R^7$, $S(O)_2R^7$ and $S(O)_2NR^7R^{7A}$;
$R^{5a}$ and $R^{5b}$ are independently at each occurrence selected from H, $C_1$-$C_4$-alkyl and halo;
$R^6$ is independently at each occurrence selected from: H, $C_1$-$C_6$-alkyl and $C_1$-$C_6$-haloalkyl;

$R^7$ and $R^{7A}$ are independently at each occurrence selected from: H and $C_1$-$C_6$-alkyl;

$R^8$ is independently at each occurrence selected from: H, $C_1$-$C_6$-alkyl, $C(O)C_1$-$C_6$-alkyl and $S(O)_2$—$C_1$-$C_6$-alkyl;

and wherein any of the abovementioned alkyl, alkenyl, alkynyl, cycloalkyl, heterocycloalkyl, heteroaryl or phenyl groups is optionally substituted where chemically allowable by from 1 to 4 groups independently selected from oxo, $C_1$-$C_6$-alkyl, $C_2$-$C_6$-alkynyl, $C_2$-$C_6$-alkenyl, $C_1$-$C_6$-haloalkyl, $OR^a$, $NR^aR^b$, $SR^a$, $C(O)OR^a$, $C(O)NR^aR^a$, halo, cyano, nitro, $C(O)R^a$, $S(O)_2OR^a$, $S(O)_2R^a$ and $S(O)_2NR^aR^a$; wherein $R^a$ is independently at each occurrence selected from: H and $C_1$-$C_6$-alkyl; and $R^b$ is independently at each occurrence selected from: H, $C_1$-$C_6$-alkyl, $C(O)C_1$-$C_6$-alkyl and $S(O)_2$—$C_1$-$C_6$-alkyl.

2. The compound according to clause 1, wherein $R^Z$ is H, $R^X$ is H, $R^Y$ is $CH_3$, and $R^W$ is OH.

3. The compound according to clause 1 or clause 2, wherein $L^1$ is absent.

4. The compound according to clause 1 or clause 2, wherein $L^1$ is $CR^{2a}R^{2b}$.

5. The compound according to any one of clauses 1 to 3, wherein $L^2$ is —$NR^{3b}C(O)$—.

6. The compound according to any of clauses 1 to 5, wherein -$(L^5$-$L^4$-$)_n$-$L^3$ is —$(CR^{4a}R^{4b})_o$-$L^4$-$(CR^{4c}R^{4d})$, wherein o is selected from 3 to 10; p is selected from 1 to 3; wherein $R^{4a}$ and $R^{4b}$ are each independently at each occurrence selected from: H, $C_1$-$C_6$-alkyl, $C_1$-$C_6$-haloalkyl, $OR^6$, and $NR^7R^8$; and $R^{4c}$ and $R^{4d}$ are each independently at each occurrence selected from: H and methyl.

7. The compound according to clause 6, wherein -$L^4$- is —$NR^{3b}C(O)$—

8. The compound according to clause 6, wherein -$L^4$- is absent.

9. The compound according to any of clauses 1 to 8, wherein n, $L^1$, $L^2$, $L^3$, $L^4$ and $L^5$ are selected such that length of the linker is from 8 to 14 atoms 10. A compound of any one of clauses 1 to 9, wherein $R^{1a}$, $R^{1b}$ and $R^{1c}$ are each substituted phenyl.

11. A compound of any one of clauses 1 to 9, wherein $R^{1a}$, $R^{1b}$ and $R^{1c}$ are each $C_3$ to $C_8$-cycloalkyl.

12. A compound of any one of clauses 1 to 9, wherein $R^{1a}$, $R^{1b}$ and $R^{1c}$ are each benzyl.

13. A compound of any one of clauses 1 to 9, wherein $R^{1a}$ and $R^{1b}$ are each unsubstituted phenyl and $R^{1c}$ is independently selected from: substituted phenyl, biphenyl, naphthyl, 5-, 6-, 9- or 10-membered heteroaryl, $C_3$ to $C_8$-cycloalkyl, $C_1$-$C_8$-alkyl and 5- to 8-membered heterocycloalkyl.

14. A compound of any one of clauses 1 to 9, wherein $R^{1a}$ and $R^{1b}$ are each $C_3$ to $C_8$-cycloalkyl and $R^{1c}$ is independently selected from: phenyl, biphenyl, naphthyl, 5-, 6-, 9- or 10-membered heteroaryl, $C_1$-$C_8$-alkyl and 5- to 8-membered heterocycloalkyl.

15. A compound of any one of clauses 1 to 9, wherein at least one of $R^{1a}$, $R^{1b}$ and $R^{1c}$ is $C_1$-$C_6$-alkyl.

16. A compound of clause 15, wherein any of $R^{1a}$, $R^{1b}$ and $R^{1c}$ that are not $C_1$-$C_6$-alkyl are phenyl.

18. A compound according to any of clauses 1 to 16, for medical use.

19. The compound according to any of clauses 1 to 16, for use in the treatment of cancer.

20. A method for the treatment of cancer, wherein the method comprises the administration of a therapeutically effective amount of a compound according to any one of clauses 1 to 16.

21. A pharmaceutical composition comprising the compound of clauses 1 to 16 and one or more pharmaceutically acceptable excipients.

DETAILED DESCRIPTION

Given below are definitions of terms used in this application. Any term not defined herein takes the normal meaning as the skilled person would understand the term.

The term "halo" or "halogen" refers to an atom selected from fluorine, chlorine, bromine and iodine. "Halo" or "halogen" may refer to an atom selected from Cl and F. "Halo" or "halogen" may refer to fluorine.

The term "alkyl" refers to a linear or branched hydrocarbon chain. The term "$C_1$-$C_8$ alkyl" refers to a linear or branched hydrocarbon chain containing 1, 2, 3, 4, 5, 6, 7 or 8 carbon atoms. The term "$C_1$-$C_6$ alkyl" refers to a linear or branched hydrocarbon chain containing 1, 2, 3, 4, 5 or 6 carbon atoms. The term "$C_1$-$C_6$ alkyl" for example refers to methyl, ethyl, n-propyl, iso-propyl, n-butyl, sec-butyl, tert-butyl, n-pentyl and n-hexyl. The "alkyl" group may be substituted or unsubstituted by one or more substituents. Substituents for the alkyl group may be halo (for example fluorine, chlorine, bromine and iodine), OH and $C_1$-$C_6$ alkoxy. In addition, alkylene groups may be linear or branched and may have two places of attachment to the remainder of the molecule.

The term "alkylene" refers to a divalent group which is a linear or branched hydrocarbon chain. With the "alkylene" group being divalent, the group must form two bonds to other groups. The term "$C_1$-$C_8$-alkylene" may refer to —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH_2CH_2CH_2CH_2CH_2CH_2CH_2$—, —$CH_2CH_2CH_2CH_2CH_2CH_2CH_2CH_2$— or substituted equivalents thereof. The alkylene group may be unsubstituted or substituted by one or more substituents.

The term "cycloalkyl" refers to a saturated hydrocarbon ring system. The term "$C_3$-$C_8$ cycloalkyl" refers to a saturated hydrocarbon ring system containing 3, 4, 5, 6, 7 or 8 carbon atoms. The ring system may be a single ring or a bi-cyclic or tri-cyclic ring system. Where the ring system is bicyclic one of the rings may be an aromatic ring, for example as in indane. The term "cycloalkyl" may refer to, for example, cyclopropyl, cyclobutyl, cyclopentyl, cyclohexyl, cycloheptyl, cyclooctyl, and indane. The cycloalkyl group may be substituted with one or more substituents.

The term "haloalkyl" refers to a linear or branched hydrocarbon chain which is substituted with at least one halogen atom which are independently selected at each occurrence from fluorine, chlorine, bromine and iodine. For example, the term "$C_1$-$C_6$ haloalkyl" refers to a linear or branched hydrocarbon chain containing 1, 2, 3, 4, 5 or 6 carbon atoms. The halogen atom may be substituted at any position on the hydrocarbon chain. The term "$C_1$-$C_6$ haloalkyl" may refer to, for example, fluoromethyl, trifluoromethyl, chloromethyl, fluoroethyl, trifluoroethyl, chloroethyl, trichloroethyl (such as 1,2,2-trichloroethyl and 2,2,2-trichloroethyl), fluoropropyl and chloropropyl. The haloalkyl group may be substituted with one or more substituents.

The term "alkenyl" refers to a linear or branched hydrocarbon chain containing at least one carbon-carbon double bond and having at least two carbon atoms. The term "$C_2$-$C_6$ alkenyl" refers to a linear or branched hydrocarbon chain containing at least one carbon-carbon double bond and having 2, 3, 4, 5 or 6 carbon atoms. The double bond or double bonds may be E or Z isomers. The double bond may be present at any possible position of the hydrocarbon chain. The term "$C_2$-$C_6$ alkenyl" may refer to, for example, ethenyl, propenyl, butenyl, butadienyl, pentenyl, pentadienyl, hexenyl and hexadienyl. The alkenyl group may be substituted or unsubstituted by one or more substituents.

The term "cycloalkenyl" refers to an unsaturated hydrocarbon ring system. The term "$C_3$-$C_8$ cycloalkenyl" refers to an unsaturated hydrocarbon ring system containing 3, 4, 5, 6, 7 or 8 carbon atoms. The ring may contain more than one double bond. The term cycloalkenyl may refer to, for example cyclopropenyl, cyclobutenyl, cyclopentenyl, cyclopentadienyl, cyclohexenyl, cyclohexadienyl, cycloheptenyl, cycloheptadiene, cyclooctenyl and cyclooctadienyl. The cycloalkenyl group may be substituted with one or more substituents.

The term "alkynyl" refers to a linear or branched hydrocarbon chain containing at least one carbon-carbon triple bond and having at least two carbon atoms. The term "$C_2$-$C_6$ alkynyl" refers to a linear or branched hydrocarbon chain containing at least one carbon-carbon triple bond and having 2, 3, 4, 5 or 6 carbon atoms. The triple bond or triple bonds may be present at any possible position of the hydrocarbon chain. The term "$C_2$-$C_6$ alkynyl" may refer to, for example, ethynyl, propynyl, butynyl, pentynyl and hexynyl. The alkynyl group may be unsubstituted or substituted by one or more substituents.

The term "heteroalkyl" refers to a linear or branched hydrocarbon chain containing at least one heteroatom selected from N, O and S which is positioned between any possible carbon atom in the chain or at the end of the chain. The term "$C_1$-$C_6$ heteroalkyl" refers to a linear or branched hydrocarbon chain containing 1, 2, 3, 4, 5, or 6 carbon atoms and at least one heteroatom selected from N, O and S which is positioned between any possible carbon atom in the chain or at the end of the chain. The heteroalkyl may be attached to another group by the heteroatom or the carbon atom. The term "$C_1$-$C_6$ heteroalkyl" may refer to, for example, —$CH_2NHCH_3$, —$NHCH_2CH_3$ and —$CH_2CH_2NH_2$. The heteroalkyl group may be unsubstituted or substituted by one or more substituents.

The term "heterocycloalkyl" refers to a saturated hydrocarbon ring system containing at least one heteroatom within the ring system selected from N, O and S. The term "5- to 8-membered heterocycloalkyl" refers to a saturated hydrocarbon ring with 5, 6, 7, 8, 9 or 10 atoms selected from carbon, N, O and S, at least one being a heteroatom. The "heterocycloalkyl" group may also be denoted as a "3 to 10 membered heterocycloalkyl" which is also a ring system containing 3, 4, 5, 6, 7, 8, 9 or 10 atoms at least one being a heteroatom. The ring system may be a single ring or a bi-cyclic or tri-cyclic ring system. Bicyclic systems may be spiro-fused, i.e. where the rings are linked to each other through a single carbon atom; vicinally fused, i.e. where the rings are linked to each other through two adjacent carbon or nitrogen atoms; or they may share a bridgehead, i.e. the rings are linked to each other by two non-adjacent carbon or nitrogen atoms. Where the ring system is bicyclic one of the rings may be an aromatic ring, for example as in chromane. The "heterocycloalkyl" may be bonded to the rest of the molecule through any carbon atom or heteroatom. The "heterocycloalkyl" may have one or more, e.g. one or two, bonds to the rest of the molecule: these bonds may be through any of the atoms in the ring. For example, the "heterocycloalkyl" may be oxirane, aziridine, azetidine, oxetane, tetrahydrofuran, pyrrolidine, imidazolidine, succinimide, pyrazolidine, oxazolidine, isoxazolidine, thiazolidine, isothiazolidine, piperidine, morpholine, thiomorpholine, piperazine, tetrahydropyran, and chromane.

The term "heterocycloalkenyl" refers to an unsaturated hydrocarbon ring system containing at least one heteroatom selected from N, O or S. The term "$C_3$-$C_8$ heterocycloalkenyl" refers to an unsaturated hydrocarbon ring system containing 3, 4, 5, 6, 7 or 8 carbon atoms and at least one heteroatom selected from N, O or S. There may be more than one double bond present. The double bond will typically be between two carbon atoms but may be between a carbon atom and a nitrogen atom. There may also be more than 1 heteroatom present. For example, there may be 1, 2 or 3 heteroatoms present. The ring system may be a single ring or a bi-cyclic or tri-cyclic ring system. Where the ring system is bicyclic one of the rings may be an aromatic ring, for example as in indoline and dihydrobenzofuran. The heterocycloalkenyl may be attached to another group by any carbon or heteroatom. The term heterocycloalkenyl may refer to, for example tetrahydropyridine, dihydropyran, dihydrofuran, pyrroline, dihydrobenzofuran, dihydrobenzothiophene and indoline. The heterocycloalkenyl group may be substituted with one or more substituents.

The term "aryl" refers to an aromatic hydrocarbon ring system which satisfies Huckel's rule for aromaticity or that contains a ring system which satisfies Huckel's rule for aromaticity. As such an aryl group may be a single ring or a bi-cyclic or tri-cyclic ring system. The term "aryl" may refer to, for example, phenyl, naphthyl, indane, tetralin and anthracene. The aryl group may be unsubstituted or substituted with one or more substituents. Any aryl group may be a phenyl ring.

The term "heteroaryl" refers to an aromatic hydrocarbon ring system with at least one heteroatom selected from N, O or S which satisfies Huckel's rule for aromaticity or a ring system that contains a heteroatom and an aromatic hydrocarbon ring. The heteroaryl may be a single ring system or a fused ring system. The term "5-, 6-, 9- or 10-membered heteroaryl" refers to an aromatic ring system within 5, 6, 9, or 10 members selected from carbon, N, O or S either in a single ring or a bicyclic ring system. The term heteroaryl may refer to, for example, imidazole, thiazole, oxazole, isothiazole, isoxazole, triazole, tetraazole, thiopheene, furan, thianthrene, pyrrole, benzimidazole, pyrazole, pyrazine, pyridine, pyrimidine, indole, isoindole, quinolone, and isoquinoline.

The term "alkoxy" refers to an alkyl group which is linked to another group by oxygen. The alkyl group may be linear or branched. The term "$C_1$-$C_6$ alkoxy" refers to an alkyl group containing 1, 2, 3, 4, 5 or 6 carbon atoms which is linked to another group by oxygen. The alkyl group may be, for example, methyl, ethyl, n-propyl, iso-propyl, n-butyl, sec-butyl, tert-butyl, n-pentyl and n-hexyl. The term "$C_1$-$C_6$ alkoxy" may refer to, for example, methoxy, ethoxy, n-propoxy, iso-propoxy, n-butoxy, sec-butoxy, tert-butoxy, n-pentoxy and n-hexoxy. The alkyl group may be substituted or unsubstituted by one or more substituents.

A bond terminating in a "⌇" means that the bond is connected to another group that is not shown. A bond terminating inside a cyclic structure and not terminating at an atom of the ring structure represents that the bond may be connected to any of the atoms in the ring structure where allowed by valency.

Where a group is substituted, it may be substituted at any point on the group where chemically possible and consistent with valency requirements. The group may be substituted by one or more substituents. For example, the group may be substituted with 1, 2, 3 or 4 substituents. Where there are two or more substituents, the substituents may be the same or different. Substituent(s) may be, for example, halo, CN, nitro, oxo, $C_1$-$C_6$-alkyl, $C_2$-$C_6$-alkynyl, $C_2$-$C_6$-alkenyl, $C_1$-$C_6$-haloalkyl, $OR^a$, $NR^aR^b$, $SR^a$, $C(O)OR^a$, $C(O)NR^aR^a$, halo, cyano, nitro, $C(O)R^a$, $S(O)_2OR^a$, $S(O)_2R^a$ and $S(O)_2NR^aR^a$; wherein $R^a$ is independently at each occurrence selected from: H and $C_1$-$C_6$-alkyl; and $R^b$ is independently at each occurrence selected from: H, $C_1$-$C_6$-alkyl, $C(O)C_1$-$C_6$-alkyl and $S(O)_2$—$C_1$-$C_6$-alkyl.

If chemically possible to do so, a cyclic substituent may be substituted on a group so as to form a spiro-cycle.

Substituents are only present at positions where they are chemically possible, the person skilled in the art being able to decide (either experimentally or theoretically) without inappropriate effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in "⁀".

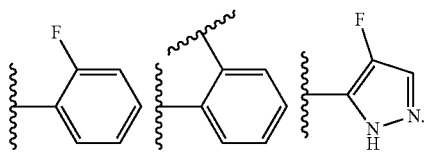

"Meta" substitution is a substitution pattern where two substituents are on carbons one carbon removed from each other, i.e with a single carbon atom between the substituted carbons. In other words there is a substituent on the second atom away from the atom with another substituent. For example the groups below are meta substituted.

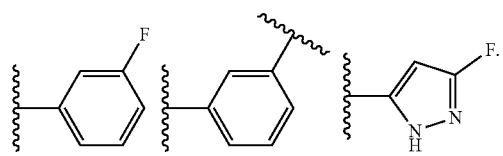

"Para" substitution is a substitution pattern where two substituents are on carbons two carbons removed from each other, i.e with two carbon atoms between the substituted carbons. In other words there is a substituent on the third atom away from the atom with another substituent. For example the groups below are para substituted.

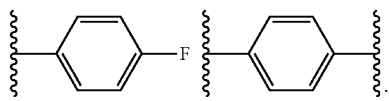

The cation of formula (I) will be associated with a pharmaceutically acceptable anionic counter ion for administration to a subject. Nevertheless, where either the cation of formula (I) or the anionic counter ion comprise either basic or acidic groups, those groups may themselves be protonated or deprotonated and associated with an appropriate counter ion.

Suitable acid addition salts are formed from acids which form non-toxic salts, for example, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts, for example include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts. A review of suitable salts can be found in "Handbook of Pharmaceutical Salts: Properties, Selection, and Use" by Stahl and Wermuth (Wiley-VCH, Weinheim, Germany, 2002).

The salt may be an acid addition salt.

The salts may be formate or hydrochloride.

Pharmaceutically acceptable salts of compounds of formula (I) may be prepared by one or more of the following methods:
(i) reacting the compound of formula (I) with the desired acid or base;
(ii) removing an acid- or base-labile protecting group from a suitable precursor of the compound of formula (I) or by ring-opening a suitable cyclic precursor, for example, a lactone or lactam, using the desired acid or base; or
(iii) converting one salt of the compound of formula (I) to another by reaction with an appropriate acid or base or by means of a suitable ion exchange column.

The reactions above are typically carried out in solution and the resulting salt may precipitate out and be collected by filtration or may be recovered by evaporation of the solvent. The degree of ionisation in the resulting salt may vary from completely ionised to almost non-ionised.

The compounds may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Complexes are contemplated, such as clathrates, drug-host inclusion complexes wherein, in contrast to the aforementioned solvates, the drug and host are present in stoichiometric or non-stoichiometric amounts. Complexes of the drug containing two or more organic and/or inorganic components which may be in stoichiometric or non-stoichiometric amounts are also contemplated. The resulting complexes may be ionised, partially ionised, or non- ionised. A review of such complexes is found in J Pharm Sci, 64 (8), 1269-1288 by Haleblian (August 1975).

Compounds, ions and salts described in this specification may be isotopically-labelled (or "radio-labelled"). Accordingly, one or more atoms are replaced by an atom having an atomic mass or mass number different from the atomic mass or mass number typically found in nature. Examples of radionuclides that may be incorporated include $^2$H (also written as "D" for deuterium), $^3$H (also written as "T" for tritium), $^{11}$C, $^{13}$C, $^{14}$C, $^{15}$O, $^{17}$O, $^{18}$O, $^{18}$F and the like. The radionuclide that is used will depend on the specific application of that radio-labelled derivative. For example, for in vitro competition assays, $^3$H or $^{14}$C are often useful. For radio-imaging applications, $^{11}$C or $^{18}$F are often useful. In some embodiments, the radionuclide is $^3$H. In some embodiments, the radionuclide is $^{14}$C. In some embodiments, the radionuclide is $^{11}$C. And in some embodiments, the radionuclide is $^{18}$F.

Hereinafter all references to compounds of any formula include references to salts, solvates and complexes thereof and to solvates and complexes of salts thereof.

The compounds include a number of formula as herein defined, including all polymorphs and crystal habits thereof, prodrugs and isomers thereof (including optical, geometric and tautomeric isomers) as hereinafter defined and isotopically-labelled compounds of the invention.

Before purification, the compounds may exist as a mixture of enantiomers depending on the synthetic procedure used. The enantiomers can be separated by conventional techniques known in the art. Thus, the compounds cover individual enantiomers as well as mixtures thereof.

For some of the steps of the process of preparation of the compounds of formula (I), it may be necessary to protect potential reactive functions that are not wished to react, and to cleave said protecting groups in consequence. In such a case, any compatible protecting radical can be used. In particular, methods of protection and deprotection such as those described by T. W. Greene (Protective Groups in Organic Synthesis, A. Wiley—Interscience Publication, 1981) or by P. J. Kocienski (Protecting groups, Georg Thieme Verlag, 1994), can be used. All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

Also, the compounds as well as intermediates for the preparation thereof can be purified according to various well-known methods, such as for example crystallization or chromatography.

The method of treatment or the compound for use in the treatment of solid tumours, leukaemia, lymphoma, sarcoma, or carcinoma as defined hereinbefore may be applied as a sole therapy or be a combination therapy with an additional active agent.

The method of treatment or the compound for use in the treatment of solid tumours, leukaemia, lymphoma, sarcoma, or carcinoma may involve, in addition to the compound of the invention, conventional surgery or radiotherapy or chemotherapy. Such chemotherapy may include one or more of the following categories of anti-cancer agents:

(i) antiproliferative/antineoplastic drugs and combinations thereof, such as alkylating agents (for example cis-platin, oxaliplatin, carboplatin, cyclophosphamide, nitrogen mustard, bendamustin, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, pemetrexed, cytosine arabinoside, and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, mitoxantrone and camptothecin);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors;

(v) antiangiogenic agents such as those which inhibit the effects of vascular endothelial growth factor, for example the anti-vascular endothelial cell growth factor antibody bevacizumab (Avastin™); thalidomide; lenalidomide; and for example, a VEGF receptor tyrosine kinase inhibitor such as vandetanib, vatalanib, sunitinib, axitinib and pazopanib;

(vi) gene therapy approaches, including for example approaches to replace aberrant genes such as aberrant p53 or aberrant BRCA1 or BRCA2;

(vii) immunotherapy approaches, including checkpoint inhibitors of targets such as PD-1, PD-L1 and CTCLA-4, for example antibody therapy such as alemtuzumab, rituximab, ibritumomab tiuxetan (Zevalin®), pembrolizumab and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); and toll-like receptor modulators for example TLR-7 or TLR-9 agonists; and (viii) cytotoxic agents for example fludaribine (fludara), cladribine, pentostatin (Nipent™);

(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, cloprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluorocortisone, fluorocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(x) targeted therapies, for example PI3Kd inhibitors, for example idelalisib and perifosine.

Such combination treatment may be achieved by way of the simultaneous, sequential or separate dosing of the individual components of the treatment. Such combination products may be administered so that the combination is provided in a therapeutically effective amount, for example the compounds of this invention may be administered within a therapeutically effective dosage range described herein and the other pharmaceutically-active agent may be administered in an amount of less than or within its approved dosage range.

According to a further aspect of the invention there is provided a pharmaceutical product comprising a compound of the first aspect of the invention, or a pharmaceutically acceptable salt thereof as defined herein and an additional active agent. The additional active agent may be a cancer therapy as defined hereinbefore for the combination treatment of cancer.

According to a further aspect of the invention there is provided a method of treating cancer comprising administering a therapeutically effective amount of a compound of the invention, or a pharmaceutically acceptable salt thereof simultaneously, sequentially or separately with an additional anti-cancer agent, as defined hereinbefore, to a patient in need thereof.

According to a further aspect of the invention there is provided a compound of the invention, or a pharmaceutically acceptable salt thereof for use simultaneously, sequentially or separately with an additional anti-cancer agent as defined herein, in the treatment of cancer.

According to another aspect of the invention there is provided a use of the compound of the invention in combination with an anti-cancer agent, such as those hereinbefore described. The compound of formula (I) may be used simultaneously, sequentially or separately with the additional anti-cancer agent. The use may be in a single combination product comprising the compound of the invention and the anti-cancer agent. The additional anti-cancer agent may be a further compound of the first aspect of the invention.

According to a further aspect there is provided a method of providing a combination product, wherein the method comprises providing a compound of the invention simultaneously, sequentially or separately with an anti-cancer agent, as defined hereinbefore. The method may comprise combining the compound of the invention and the anti-cancer agent in a single dosage form. Alternatively, the method may comprise providing the anti-cancer agent as separate dosage forms.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

For the above-mentioned compounds of the invention the dosage administered will, of course, vary with the compound employed, the mode of administration, the treatment desired and the disorder indicated. For example, if the compound of the invention is administered orally, then the daily dosage of the compound of the invention may be in the range from 0.01 micrograms per kilogram body weight (μg/kg) to 100 milligrams per kilogram body weight (mg/kg).

A compound of the invention, or pharmaceutically acceptable salt thereof, may be used on their own but will generally be administered in the form of a pharmaceutical composition in which the compounds of the invention, or pharmaceutically acceptable salt thereof, is in association with a pharmaceutically acceptable adjuvant, diluent or carrier. Conventional procedures for the selection and preparation of suitable pharmaceutical formulations are described in, for example, "Pharmaceuticals—The Science of Dosage Form Designs", M. E. Aulton, Churchill Livingstone, 1988.

Depending on the mode of administration of the compounds of the invention, the pharmaceutical composition which is used to administer the compounds of the invention will preferably comprise from 0.05 to 99% w (percent by weight) compounds of the invention, more preferably from 0.05 to 80% w compounds of the invention, still more preferably from 0.10 to 70% w compounds of the invention, and even more preferably from 0.10 to 50% w compounds of the invention, all percentages by weight being based on total composition.

The pharmaceutical compositions may be administered topically (e.g. to the skin) in the form, e.g., of creams, gels, lotions, solutions, suspensions, or systemically, e.g. by oral administration in the form of tablets, capsules, syrups, powders or granules; or by parenteral administration in the form of a sterile solution, suspension or emulsion for injection (including intravenous, subcutaneous, intramuscular, intravascular or infusion); by rectal administration in the form of suppositories; or by inhalation in the form of an aerosol.

For oral administration the compounds of the invention may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the compounds of the invention may be admixed with, for example, a vegetable oil or polyethylene glycol. Hard gelatine capsules may contain granules of the compound using either the above-mentioned excipients for tablets. Also liquid or semi-solid formulations of the compound of the invention may be filled into hard gelatine capsules. Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

For intravenous (parenteral) administration the compounds of the invention may be administered as a sterile aqueous or oily solution.

The size of the dose for therapeutic purposes of compounds of the invention will naturally vary according to the nature and severity of the conditions, the age and sex of the animal or patient and the route of administration, according to well-known principles of medicine.

Dosage levels, dose frequency, and treatment durations of compounds of the invention are expected to differ depending on the formulation and clinical indication, age, and co-morbid medical conditions of the patient.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with, or previous to, this specification in connection with this application and which are open to public inspection with this specification, and the contents of all such papers and documents are incorporated herein by reference.

Methods for Synthesizing Compounds

Certain ions of the invention can be synthesised according to or analogously to methods described in the General Schemes below and/by other techniques known to those of ordinary skill in the art. Certain ions of the invention can be synthesised according to or analogously to the methods described in the Examples.

Certain Ions of Formula (I) Can be Made by Scheme A

Scheme A

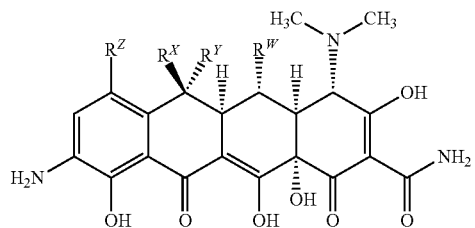

(1)

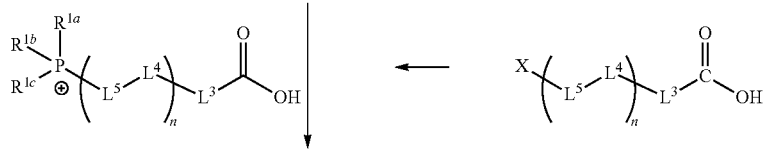

(2)        (4)

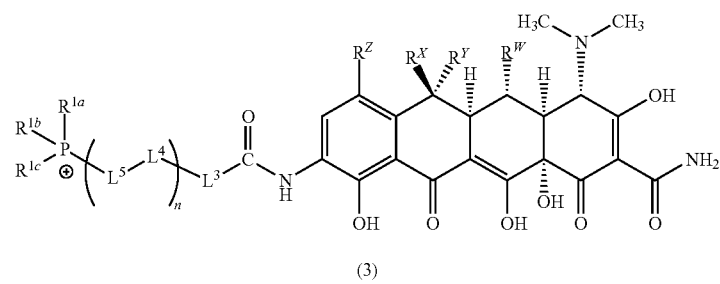

(3)

Reaction of aniline (1) with phosphonium acid (2) can furnish phosphonium amide (3). The reaction can be performed using standard peptide coupling agents, such as 1-chloro-N,N-2-trimethyl-1-propenylamine (Ghosez's reagent) or propylphosphoric anhydride in the presence of a base, such as DIEA or NaHCO$_3$ in a chlorinated solvent, such as DCM at a temperature from 10 to 30° C. Phosphonium acid (2) can be prepared from reaction of halide (4) (X=Cl or Br) with phosphine PR$^{1a}$R$^{1b}$R$^{1c}$ (10). The reaction can be accomplished by heating in an organic solvent, such as MeCN at a temperature from 50 to 80° C.

Certain Ions of Formula (I) Can be Made by Scheme B

Reaction of benzyl amine (5) with 2,5-dioxopyrrolidin-1-yl phosphonium (7) can furnish phosphonium amide (6). The reaction can be performed in the presence of a base, such as Et$_3$N, in an organic solvent, such as DCM from 10 to 30° C. The 2,5-dioxopyrrolidin-1-yl phosphonium (7) can be prepared from reaction of phosphonium acid (2) with N-hydroxysuccinimide in the presence of 1,3-dicyclohexylcarbodiimide in a chlorinated solvent, such as DCM, at a temperature from 10 to 30° C.

Scheme B

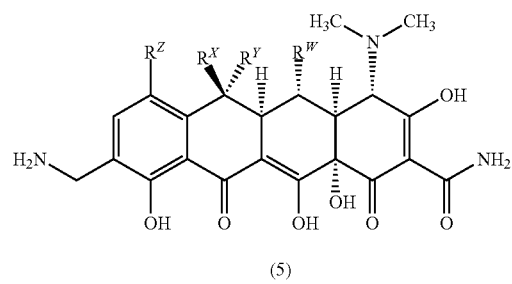

(5)

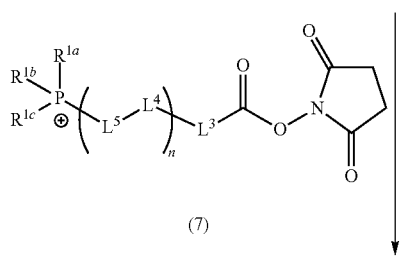

(7)

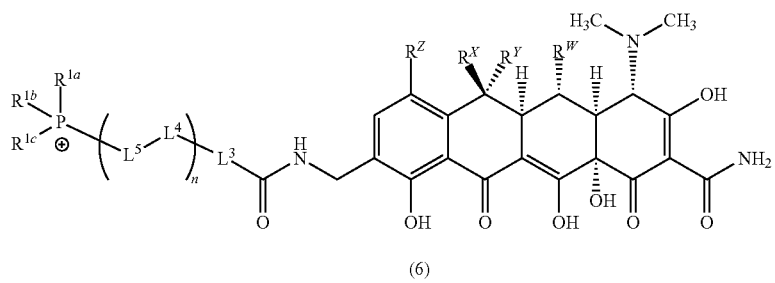

(6)

Certain Ions of Formula (I) Can be Made by Scheme C

Reaction of aniline (1) with halo sulphonic acid (8) (where X=Cl or Br; L$^6$ is a C$_2$-C$_{13}$-alkylene group optionally substituted with from 0 to 10 R$^4$ groups) can furnish halo sulphonamide (9). The reaction can be performed using SOCl$_2$ in an organic solvent, such as DMF or DCM, at a temperature from 20 to 60° C. Reaction of phosphine (10) with halo sulphonamide (9) can deliver phosphonium sulphonamide (11). The reaction can be accomplished by heating in an organic solvent, such as MeCN at a temperature from 50 to 80° C.

Scheme C

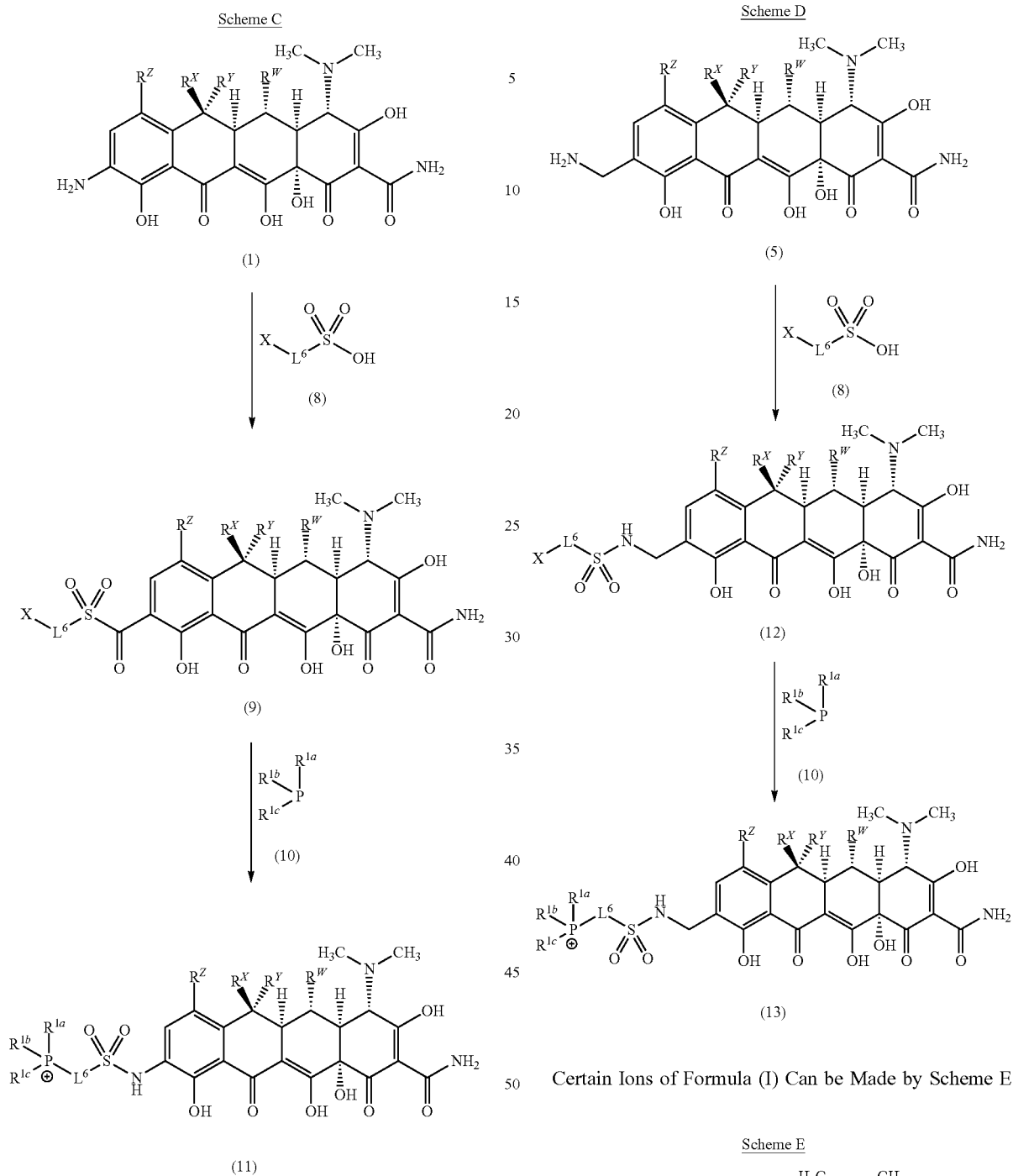

Scheme D

Certain Ions of Formula (I) Can be Made by Scheme D

Reaction of benzyl amine (5) with halo sulphonic acid (8) (where X=Cl or Br) can furnish halo sulphonamide (12). The reaction can be performed using SOCl$_2$ in an organic solvent, such as DMF or DCM, at a temperature from 20 to 60° C. Reaction of phosphine (10) with halo sulphonamide (12) can deliver phosphonium sulphonamide (13). The reaction can be accomplished by heating in an organic solvent, such as MeCN at a temperature from 50 to 80° C.

Certain Ions of Formula (I) Can be Made by Scheme E

Scheme E

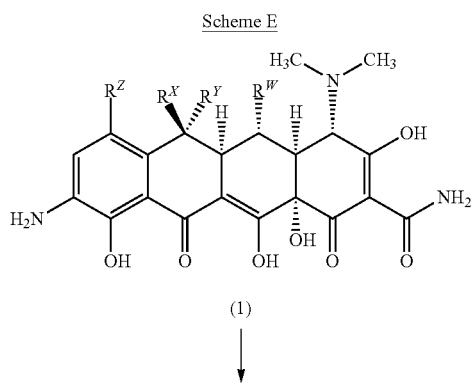

(1)

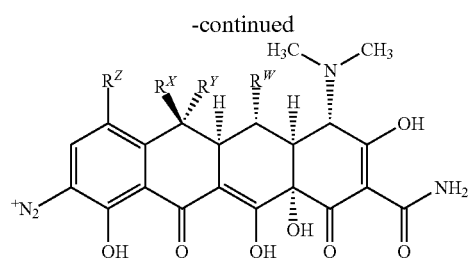

(14)

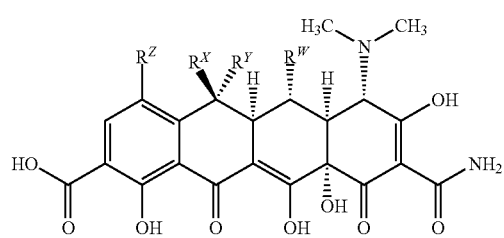

(15)

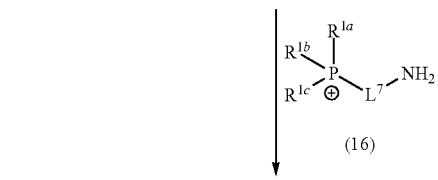

(16)

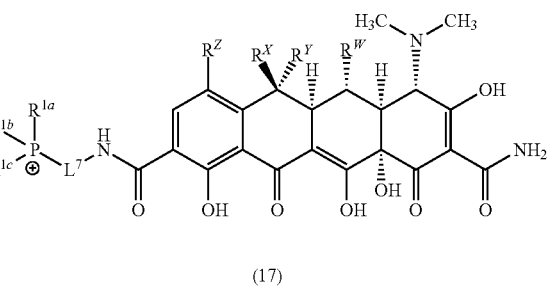

(17)

Aniline (1) can be converted to its diazonium salt (14) through the action of butyl nitrite in the presence of an acid, such as HCl. The reaction can be performed in an alcoholic solvent, such as MeOH, at a temperature from −5 to 0° C. Reaction of diazonium salt (14) with CO in the presence of a Pd catalyst, such as Pd(OAc)$_2$ can deliver carboxylic acid (15). The reaction can be accomplished in an anhydrous organic solvent, such as DMF, at room temperature. Reaction of carboxylic acid (15) with phosphonium amine (16) (L$^7$ is a C$_2$-C$_{13}$-alkylene group optionally substituted with from 0 to 10 R$^4$ groups) can furnish phosphonium amide (17). The reaction can be performed using standard peptide coupling agents, such as N-(3-dimethylaminopropyl)-N-ethylcarbodiimide HCl (EDCI) and HOBt in an organic solvent, such as DMF, at room temperature.

Phosphonium Amine (16) Can Synthesised by Scheme F.

Scheme F

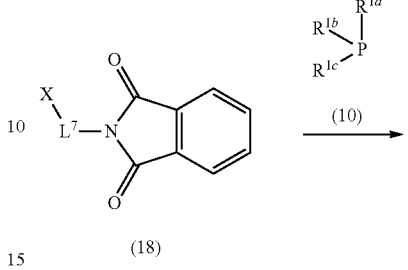

(18)

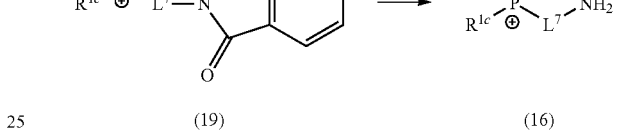

(19)            (16)

Reaction of halo isoindoline-1,3-dione (18) (where X=Cl or Br) with phosphine (10) can deliver phosphonium isoindoline-1,3-dione (19). The reaction can be performed by heating in an organic solvent, such as MeCN, at a temperature from 50 to 80° C. Reaction of the phosphonium isoindoline-1,3-dione (19) with hydrazine hydrate in an alcoholic solvent, such as EtOH, at a temperature from 50 to 75° C. can furnish phosphonium amine (16).

Certain Ions of Formula (I) Can be Made by Scheme G

Scheme G

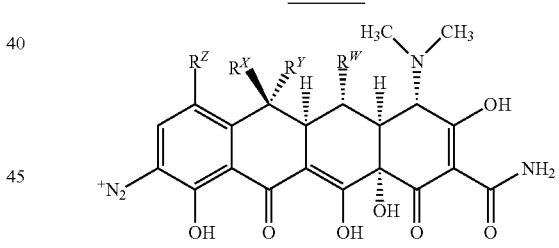

(14)

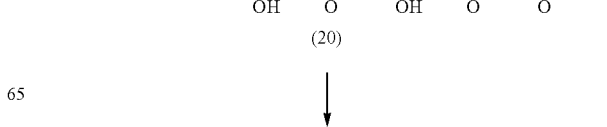

(20)

-continued

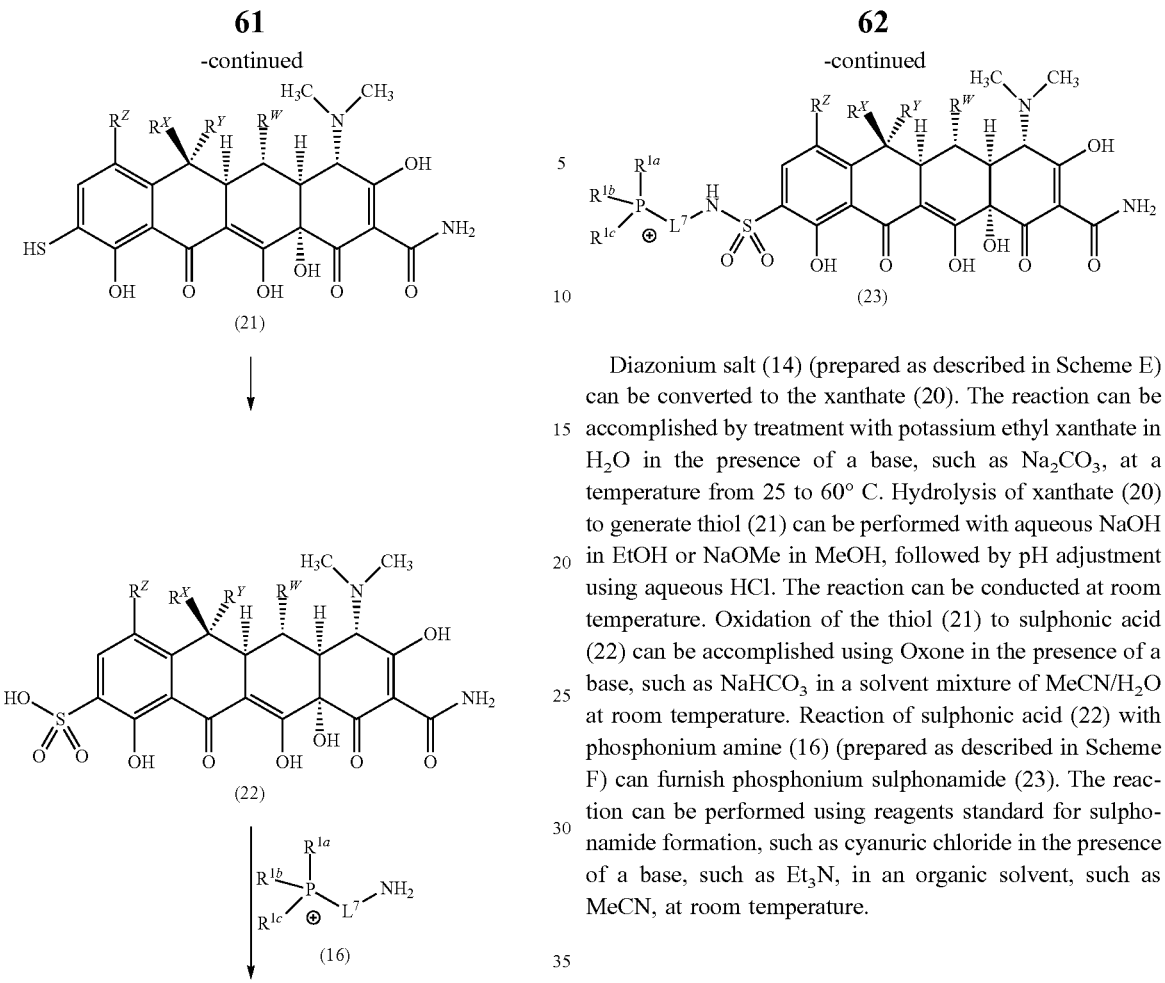

Diazonium salt (14) (prepared as described in Scheme E) can be converted to the xanthate (20). The reaction can be accomplished by treatment with potassium ethyl xanthate in $H_2O$ in the presence of a base, such as $Na_2CO_3$, at a temperature from 25 to 60° C. Hydrolysis of xanthate (20) to generate thiol (21) can be performed with aqueous NaOH in EtOH or NaOMe in MeOH, followed by pH adjustment using aqueous HCl. The reaction can be conducted at room temperature. Oxidation of the thiol (21) to sulphonic acid (22) can be accomplished using Oxone in the presence of a base, such as $NaHCO_3$ in a solvent mixture of $MeCN/H_2O$ at room temperature. Reaction of sulphonic acid (22) with phosphonium amine (16) (prepared as described in Scheme F) can furnish phosphonium sulphonamide (23). The reaction can be performed using reagents standard for sulphonamide formation, such as cyanuric chloride in the presence of a base, such as $Et_3N$, in an organic solvent, such as MeCN, at room temperature.

Certain Ions of Formula (I) Can be Made by Scheme H

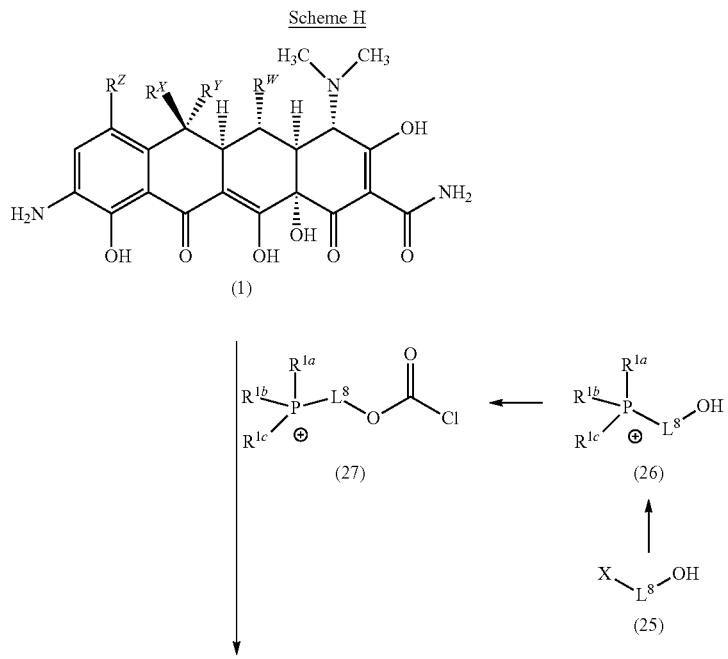

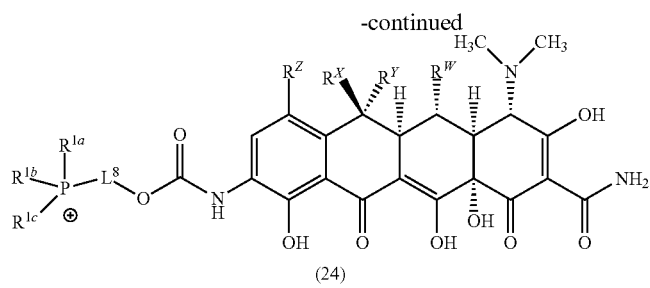

Reaction of aniline (1) with phosphonium chlorocarbonate (27) ($L^8$ is a $C_2$-$C_{13}$-alkylene group optionally substituted with from 0 to 10 $R^4$ groups) can furnish phosphonium carbamate (24). The reaction can be accomplished in the presence of a base, such as pyridine, in an organic solvent, such as DCM, at a temperature from 0° C. to room temperature. Phosphonium chloroacetate (27) can be synthesised from phosphonium alcohol (26) through treatment with triphosgene in the presence of a base, such as DIEA, in an organic solvent, such as THF, at a temperature from −5 to 5° C. Phosphonium alcohol (26) can be synthesised from halo alcohol (25) (where X=Cl or Br) and phosphine $PR^{1a}R^{1b}R^{1c}$ (10). The reaction can be accomplished by heating in an organic solvent, such as MeCN, at a temperature from 50 to 80° C.

Certain Ions of Formula (I) Can be Made by Scheme I

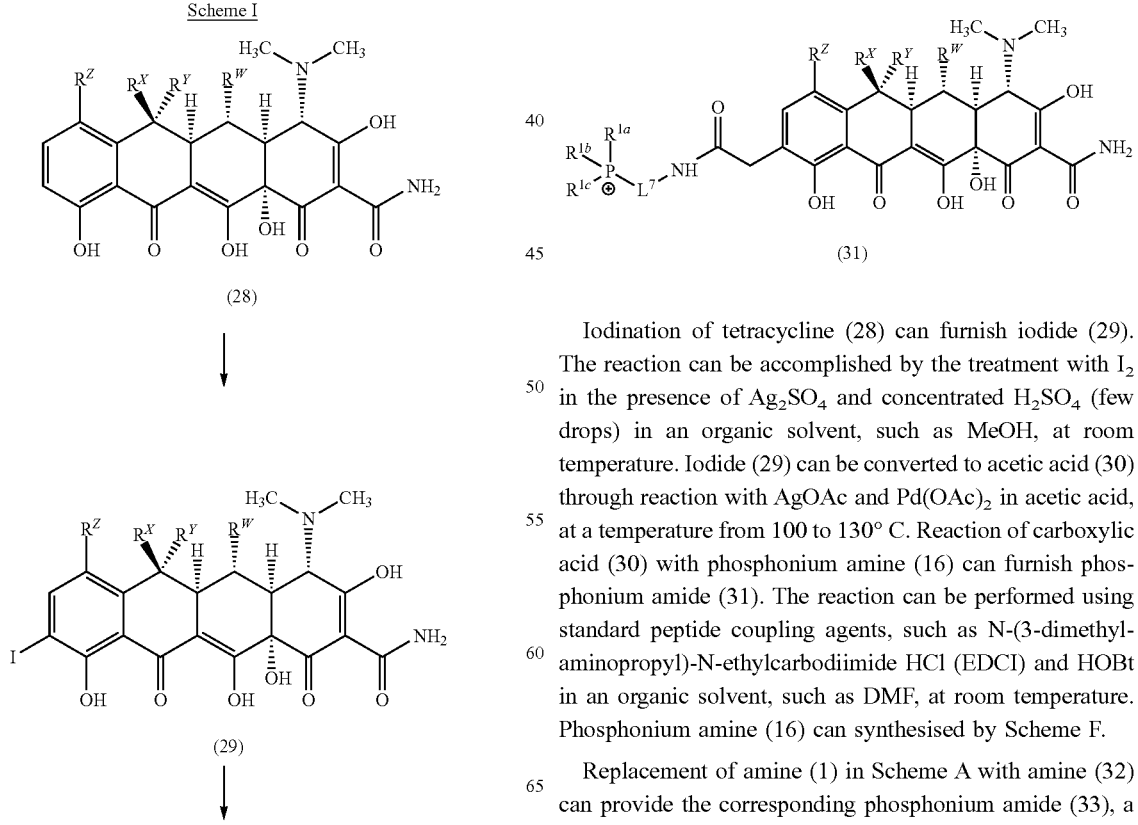

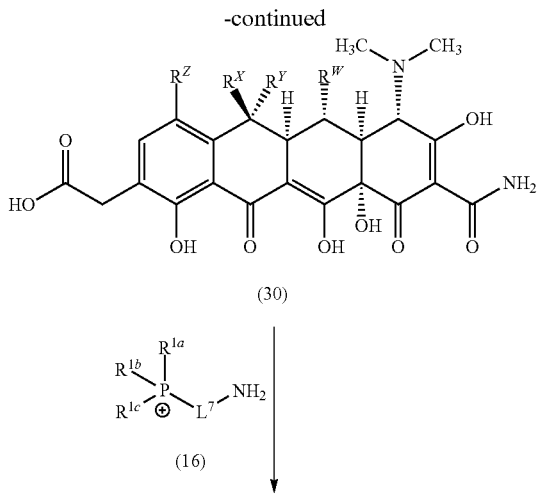

Iodination of tetracycline (28) can furnish iodide (29). The reaction can be accomplished by the treatment with $I_2$ in the presence of $Ag_2SO_4$ and concentrated $H_2SO_4$ (few drops) in an organic solvent, such as MeOH, at room temperature. Iodide (29) can be converted to acetic acid (30) through reaction with AgOAc and $Pd(OAc)_2$ in acetic acid, at a temperature from 100 to 130° C. Reaction of carboxylic acid (30) with phosphonium amine (16) can furnish phosphonium amide (31). The reaction can be performed using standard peptide coupling agents, such as N-(3-dimethylaminopropyl)-N-ethylcarbodiimide HCl (EDCI) and HOBt in an organic solvent, such as DMF, at room temperature. Phosphonium amine (16) can synthesised by Scheme F.

Replacement of amine (1) in Scheme A with amine (32) can provide the corresponding phosphonium amide (33), a subset of ions of formula (I).

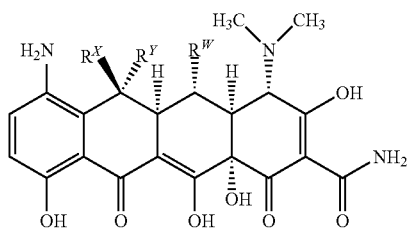

(32)

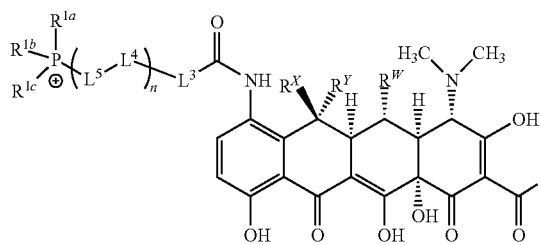

(33)

Replacement of benzyl amine (5) in Scheme B with benzyl amine (34) can provide phosphonium amide (35), a subset of ions of formula (I).

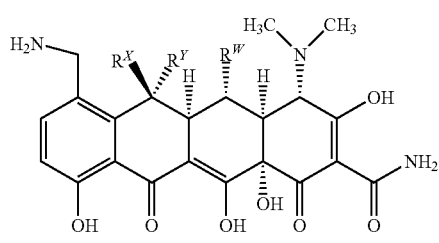

(34)

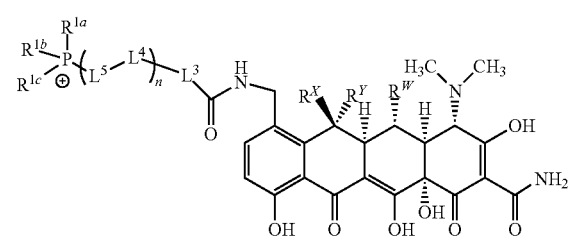

(35)

Replacement of amine (1) in Scheme C with amine (32) can provide phosphonium sulphonamide (36), a subset of ions of formula (I).

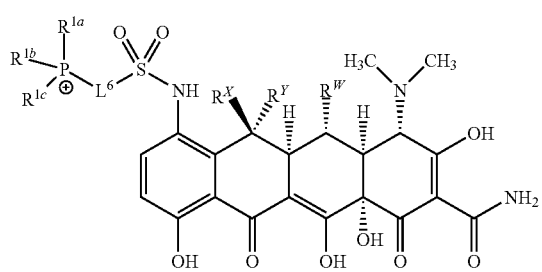

(36)

Replacement of benzyl amine (5) in Scheme D with benzyl amine (34) can provide phosphonium sulphonamide (37), a subset of ions of formula (I).

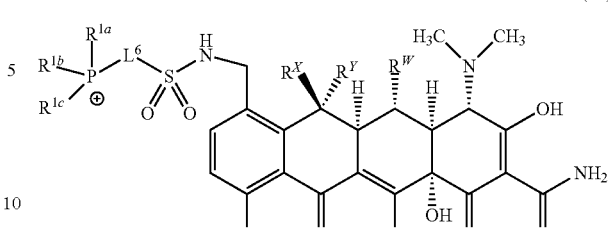

(37)

Replacement of diazonium (14) in Scheme E with diazonium (38) can provide phosphonium amide (39), a subset of ions of formula (1).

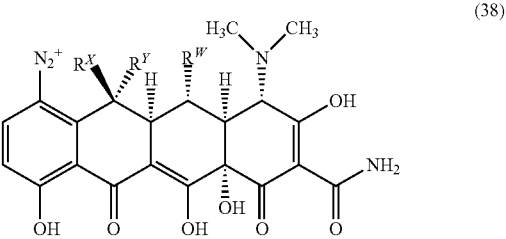

(38)

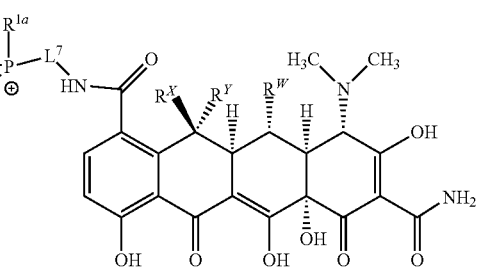

(39)

Replacement of diazonium (14) in Scheme G with diazonium (38) can provide phosphonium sulphonamide (40), a subset of ions of formula (1).

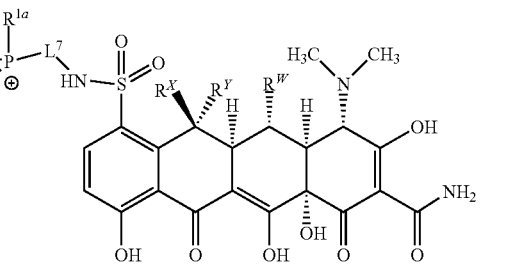

(40)

Replacement of amine (1) in Scheme H with amine (32) can provide phosphonium carbamate (41), a subset of ions of formula (I).

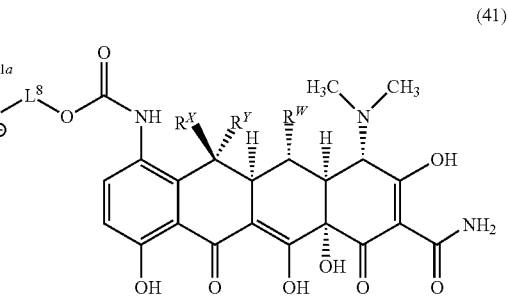

(41)

Replacement of iodide (29) in Scheme I with iodide (42) can provide phosphonium amide (43), a subset of ions of formula (I).

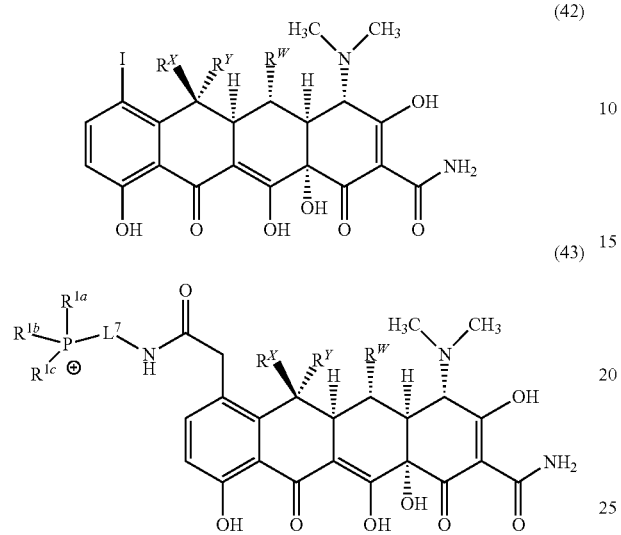

EXPERIMENTAL

Analytical Methods
NMR spectra were obtained on a 400 MHz Bruker AV III (Method A)
UPLC/MS was carried out using a Waters Acquity QDa mass detector and Method A, C or Waters SQ mass detector and Method B
Method A
Column: Waters Acquity UPLC CSH C18, 1.7 μm, 2.1×30 mm; Gradient Eluent: 5-95% MeCN/H$_2$O containing 0.1% HCOOH; Time: 0-10 min
Method B
Column: Waters Acquity UPLC CSH C18, 1.7 μm, 2.1×30 mm; Gradient Eluent: 5-95% MeCN/H$_2$O containing 0.1% HCOOH; Time: 0-15 min
Method C
Column: Waters Acquity UPLC CSH C18, 1.7 μm, 2.1×30 mm; Gradient Eluent: 5-95% MeCN/H$_2$O containing 0.1% HCOOH; Time: 0-3 min
Preparative HPLC was carried out using a ZQ Mass Spectrometer and Method A or B Method A
Waters X-Select Prep-C18, 5 μm, 19×50 mm eluting with MeCN/H$_2$O/0.1% HCOOH
Method B
Waters X-Select Prep-C18, 5 μm, 19×50 mm eluting with MeCN/H$_2$O/0.2% HCl
Abbreviations
The following abbreviations have been used throughout the specification in the Examples and in the description; N-(3-dimethylaminopropyl)-N-ethylcarbodiimide HCl (EDCI); Hydroxybenzotriazole (HOBt); Methyl tert-butyl ether (MTBE); N,N-Diisopropylethylamine (DIEA); Dichloromethane (DCM); Dimethylformamide (DMF); N-Methyl-2-pyrrolidone (NMP); Methyl tert-butyl ether (MTBE).

Example 1—(11-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}undecyl)tris(4-methoxyphenyl)phosphonium formate (11-carboxyundecyl)tris(4-methoxyphenyl)phosphonium bromide

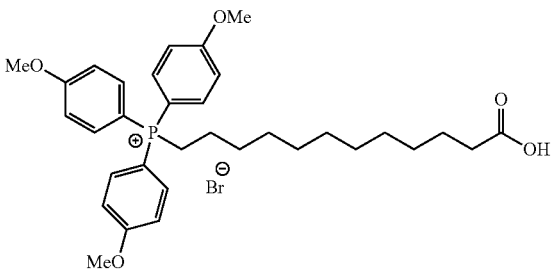 [SMILES: COc1ccc([P+](CCCCCCCCCCCC(=O)O)(c2ccc(OC)cc2)c2ccc(OC)cc2)cc1 ; [Br-]]

A mixture of 12-bromododecanoic acid (302 mg, 1.08 mmol) and tris(4-methoxyphenyl)phosphine (400 mg, 1.14 mmol) in degassed MeCN (5 mL) under N$_2$ was heated at 80° C. for 3 d. On cooling the solvent was removed in vacuo and the resulting residue purified by column chromatography eluting with 0-10% MeOH in DCM to give (11-carboxyundecyl)tris(4-methoxyphenyl)phosphonium bromide (545 mg, 80%) as a white solid.

(11-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}undecyl)tris(4-methoxyphenyl)phosphonium formate (Example 1)

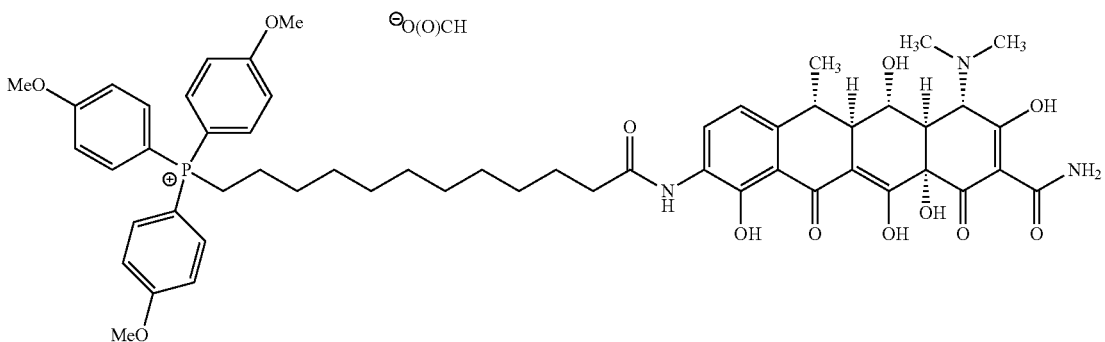 [SMILES: COc1ccc([P+](CCCCCCCCCCCC(=O)Nc2ccc3c(c2O)C(=O)C2=C(O)[C@]4(O)C(=O)C(C(N)=O)=C(O)[C@@H](N(C)C)[C@@H]4[C@@H](O)[C@@H]2[C@H]3C)(c2ccc(OC)cc2)c2ccc(OC)cc2)cc1 ; "O(O)CH"]

To a solution of 11-carboxyundecyl)tris(4-methoxyphenyl)phosphonium bromide (prepared as described in step (a)) (249 mg, 0.40 mmol) in DCM (1 mL) was added 1-chloro-N,N-2-trimethyl-1-propenylamine (Ghosez's reagent) (57 μL, 0.43 mmol). The resulting mixture was stirred at room temperature for 30 min and then added dropwise to a stirred suspension of 9-aminodoxycyline sulphate (200 mg, 0.36 mmol) and $NaHCO_3$ (301 mg, 3.59 mmol) in NMP (1 mL). The resulting reaction mixture was stirred at room temperature for 30 min, then filtered through a phase separator, which was washed with EtOH. The combined organics were concentrated under reduced pressure and dripped into cold MTBE (500 mL). The resulting precipitate was collected by filtration, washed with fresh MTBE and dried under vacuo overnight. The crude product was purified by preparative HPLC (Method A) to give (11-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}undecyl)tris(4-methoxyphenyl)phosphonium formate (35 mg, 9% yield) as a brown solid.

1H NMR (Method A) ($CD_3OD$): δ (delta) ppm 8.31 (s, 1H), 8.12 (d, J=8.5 Hz, 1H), 7.69-7.59 (m, 6H), 7.27-7.20

A suspension of 8-bromodecanoic acid (1.06 g, 4.76 mmol) in MeCN (10 mL) was heated at 40° C. until solubilised. The resulting solution was degassed with bubbling $N_2$ for 30 min and then treated with methyldiphenylphosphine (0.93 mL, 4.99 mmol). The resulting reaction mixture was heated at 90° C. under $N_2$ for 16 h. On cooling the reaction mixture was added dropwise to a stirred solution of MTBE (100 mL) and the resulting gum collected by removal of excess MTBE and dried to give ((7-carboxyheptyl)(methyl)diphenylphosphonium bromide (1.8 g, 85%) as a pale orange gum, which was used in the next step without any further purification.

LC-MS (Method C) 343.3 [M]$^+$; RT 0.80 min (7-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}heptyl)(methyl)diphenylphosphonium chloride

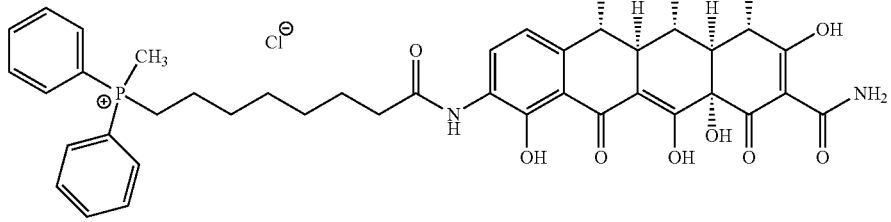

(m, 6H), 6.90 (d, J=8.5 Hz, 1H), 3.91 (s, 9H), 3.62 (dd, J=10.4, 7.8 Hz, 1H), 3.21-3.08 (m, 2H), 2.84 (s, 4H), 2.79-2.69, (m, 1H), 2.69-2.52 (m, 3H), 2.48-2.38 (m, 2H), 1.77-1.13 (m, 23H); 31P NMR (162 MHz, $CD_3OD$) δ (delta) ppm +21.41 (s); LC-MS (Method A) 992.7 [M]$^+$; RT 3.65 min Example 2—(7-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}heptyl)(methyl) diphenylphosphonium chloride (7-carboxyheptyl)(methyl)diphenylphosphonium bromide

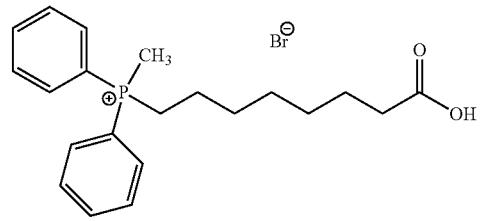 [SMILES: C[P+](CCCCCCCC(=O)O)(c1ccccc1)c1ccccc1 ; [Br-]]

To a solution of (7-carboxyheptyl)(methyl)diphenylphosphonium bromide (prepared as described in Example 2 step (a)) (205 mg, 0.48 mmol) in DCM (2.7 mL) was added 1-chloro-N,N-2-trimethyl-1-propenylamine (Ghosez's reagent) (80 μL, 0.61 mmol). The resulting mixture was stirred at room temperature for 10 min and then added dropwise to a stirred suspension of 9-aminodoxycyline hydrochloride (200 mg, 0.40 mmol) in DMF (1 mL). The resulting reaction mixture was stirred at room temperature for 20 min and then treated dropwise with 4 M HCl in dioxane (0.50 mL, 2.02 mmol). The resulting solution was added dropwise to a stirred solution of MTBE (100 mL). The resulting brown oil was isolated by removal of excess MTBE and dissolved in MeOH (2 mL), which on dropwise addition to fresh MTBE (100 mL) gave a beige solid. The solid was isolated by filtration under $N_2$ and slurried in MeCN (10 mL) at 70° C. After 1 h the hot slurry was filtered and the solid collected was further purified by preparative HPLC (Method B) to give the title compound (35 mg) as a yellow solid as its HCl salt.

31P NMR (162 MHz, DMSO-$d_6$) δ (delta) ppm +24.30 (s); LC-MS (Method B) 784 [M]$^+$; RT 2.71 min

Example 3—(7-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}heptyl) dimethylphenylphosphonium chloride (7-carboxyheptyl)dimethylphenylphosphonium bromide

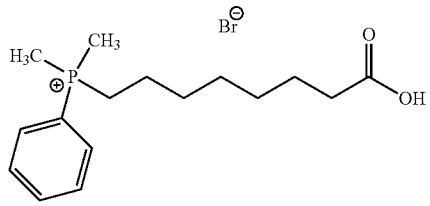 [SMILES: [Br-] ; C[P+](C)(CCCCCCCC(=O)O)c1ccccc1]

Prepared following the procedure in Example 2 step (a) but using dimethylphenylphosphine. (7-carboxyheptyl)dimethylphenylphosphonium bromide was isolated as a white solid, which was used in the next step without further purification.

(7-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}heptyl) dimethylphenylphosphonium chloride

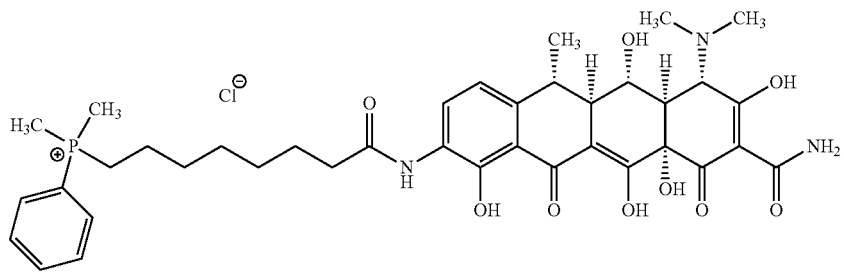 [SMILES: C[C@H]1c2ccc(NC(=O)CCCCCCC[P+](C)(C)c3ccccc3)c(O)c2C(=O)C2=C(O)[C@]3(O)C(=O)C(C(N)=O)=C(O)[C@@H](N(C)C)[C@@H]3[C@@H](O)[C@@H]21 ; [Cl-]]

Prepared following the procedure in Example 2 step (b) but using (7-carboxyheptyl)dimethylphenylphosphonium bromide (prepared as described in Example 3 step (a)). Title compound isolated as a yellow brown solid as its HCl salt. 31P NMR (162 MHz, DMSO-$d_6$) δ (delta) ppm +26.11 (s); LC-MS (Method B) 722 [M]$^+$; RT 2.11 min

Example 4—(7-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}heptyl) trimethylphosphonium chloride (7-carboxyheptyl)trimethylphosphonium bromide

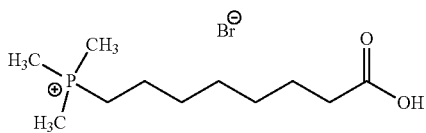

Prepared following the procedure in Example 2 step (a) but using trimethylphosphine (1 M in toluene). (7-carboxyheptyl)trimethylphosphonium bromide was isolated as a white solid, which was used in the next step without further purification.

LC-MS (Method C) 219.3 [M]$^+$; RT 0.18 min (7-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}heptyl)trimethylphosphonium chloride

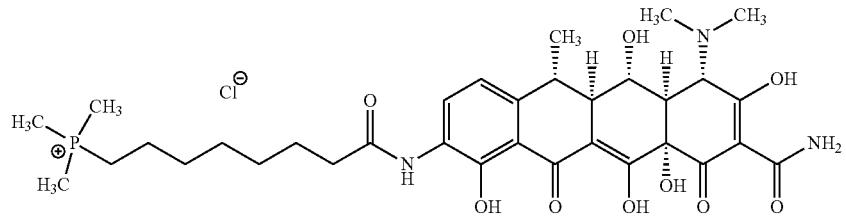 [SMILES: C[C@H]1c2ccc(NC(=O)CCCCCCC[P+](C)(C)C)c(O)c2C(=O)C2=C(O)[C@]3(O)C(=O)C(C(N)=O)=C(O)[C@@H](N(C)C)[C@@H]3[C@@H](O)[C@@H]21 ; [Cl-]]

To a solution of (7-carboxyheptyl)trimethylphosphonium bromide (prepared as described in Example 4 step (a)) (145 mg, 0.48 mmol) in DCM (2.7 mL) was added 1-chloro-N,N-2-trimethyl-1-propenylamine (Ghosez's reagent) (80 μL, 0.61 mmol). Further DCM (1 mL) was added and the resulting mixture stirred at room temperature. After 20 min the reaction mixture was added dropwise to a stirred suspension of 9-aminodoxycyline hydrochloride (200 mg, 0.40 mmol) in DMF (4.1 mL). The resulting reaction mixture was stirred at room temperature for 20 min and then treated dropwise with 4 M HCl in dioxane (0.50 mL, 2.02 mmol). The resulting solution was added dropwise to a stirred solution of MTBE (100 mL). The resulting brown oil was isolated by removal of excess MTBE and dissolved in MeOH (2 mL), which on dropwise addition to fresh MTBE (100 mL) gave a brown solid. The solid was isolated by filtration under $N_2$ and slurried in MeCN (10 mL) at 70° C. After 1 h the hot slurry was filtered and the hot filtrate concentrated under vacuo to give a dark green residue, which was further purified by preparative HPLC (Method B) to give the title compound (35 mg) as a yellow brown solid as its HCl salt.

31P NMR (162 MHz, DMSO-$d_6$) δ (delta) ppm +27.94 (s); LC-MS (Method B) 660 [M]$^+$; RT 1.51 min Example 5—(11-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}undecyl)(methyl)diphenylphosphonium chloride (11-carboxyundecyl)(methyl)diphenylphosphonium bromide

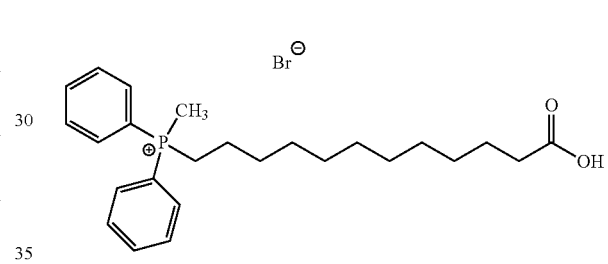

Prepared following the procedure in Example 2 step (a) but using 12-bromododecanoic acid. (11-carboxyundecyl)(methyl)diphenylphosphonium bromide was isolated as a pale orange gum, which was used in the next step without further purification.

LC-MS (Method C) 399.4 [M]$^+$; RT 1.08 min (11-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}undecyl)(methyl)diphenylphosphonium chloride

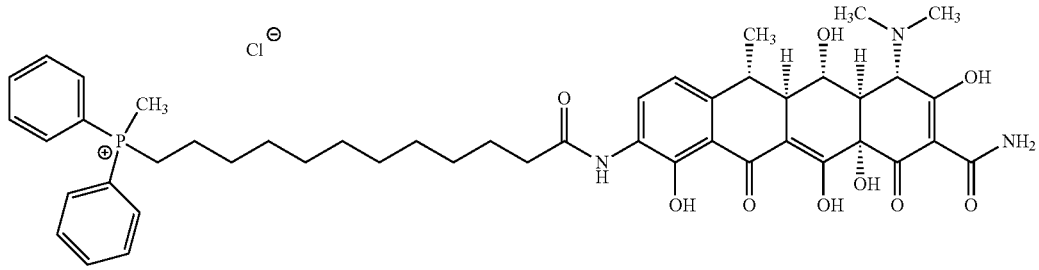 [SMILES: C[C@H]1c2ccc(NC(=O)CCCCCCCCCCC[P+](C)(c3ccccc3)c3ccccc3)c(O)c2C(=O)C2=C(O)[C@]3(O)C(=O)C(C(N)=O)=C(O)[C@@H](N(C)C)[C@@H]3[C@@H](O)[C@@H]21 ; [Cl-]]

Prepared following the procedure in Example 4 step (b) but using (11-carboxyundecyl)(methyl)diphenylphosphonium bromide (prepared as described in Example 5 step (a)). Title compound isolated as a yellow solid as its HCl salt.

31P NMR (162 MHz, DMSO-$d_6$) δ (delta) ppm +24.3 (s); LC-MS (Method B) 840 [M]$^+$; RT 3.97 min

Example 6—(11-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}undecyl)trimethylphosphonium chloride (11-carboxyundecyl)trimethylphosphonium bromide

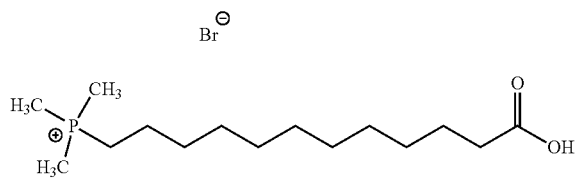 [SMILES: [Br-] ; C[P+](C)(C)CCCCCCCCCCCC(=O)O]

Prepared following the procedure in Example 2 step (a) but using 12-bromododecanoic acid and trimethylphosphine (1 M in toluene). (11-carboxyundecyl)trimethylphosphonium bromide was isolated as a white solid, which was used in the next step without further purification.

LC-MS (Method C) 275.3 [M]$^+$; RT 0.82 min (11-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}undecyl)trimethylphosphonium chloride

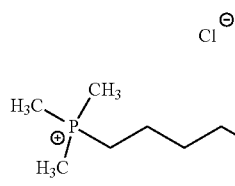
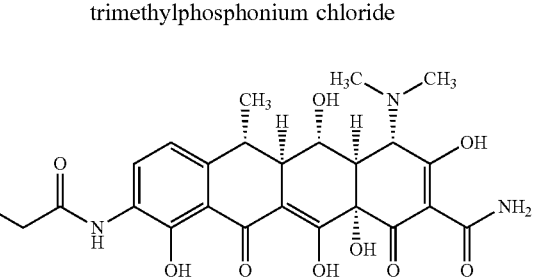

Prepared following the procedure in Example 2 step (b) but using ((11-carboxyundecyl)trimethylphosphonium bromide (prepared as described in Example 6 step (a)). Title compound isolated as a yellow brown solid as its HCl salt.

31P NMR (162 MHz, DMSO-d$_6$) δ (delta) ppm +27.91 (s); LC-MS (Method B) 716 [M]$^+$; RT 3.86 min

Example 7—(11-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}undecyl)tris(3-methylphenyl)phosphonium chloride (11-carboxyundecyl)tris(3-methylphenyl)phosphonium bromide

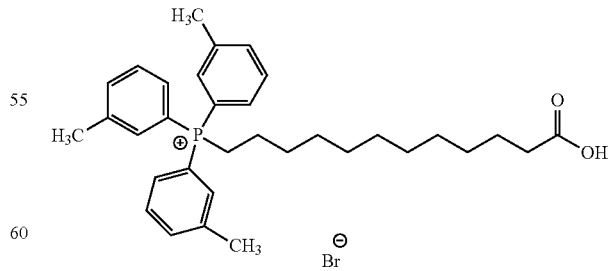

Prepared following the procedure in Example 1 step (a) but using tri(m-tolyl)phosphine. (11-carboxyundecyl)tris(3-methylphenyl)phosphonium bromide was isolated as a tar and used in the next step without any further purification.

(11-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}undecyl)tris(3-methylphenyl)phosphonium chloride

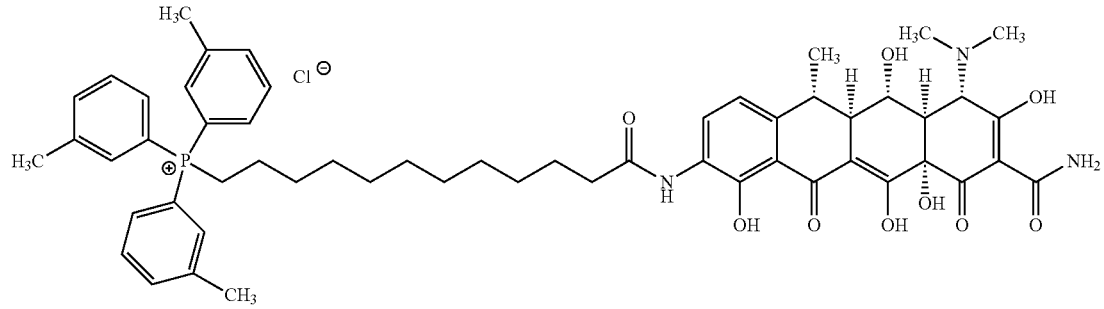 [SMILES: Cc1cccc([P+](CCCCCCCCCCCC(=O)Nc2ccc3c(c2O)C(=O)C2=C(O)[C@]4(O)C(=O)C(C(N)=O)=C(O)[C@@H](N(C)C)[C@@H]4[C@@H](O)[C@@H]2[C@H]3C)(c2cccc(C)c2)c2cccc(C)c2)c1 ; [Cl-]]

Prepared following the procedure in Example 4 step (b) but using (11-carboxyundecyl)tris(3-methylphenyl)phosphonium bromide (prepared as described in Example 7 step (a)). Title compound isolated as a yellow brown solid as its HCl salt.

31P NMR (162 MHz, DMSO-$d_6$) δ (delta) ppm +23.60 (s); LC-MS (Method B) 944.8 [M]$^+$; RT 5.21 min Example 8—(7-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}heptyl)(1-methyl-1H-pyrazol-4-yl)diphenylphosphonium chloride 4-(diphenylphosphonyl)-1-methyl-1H-pyrazole

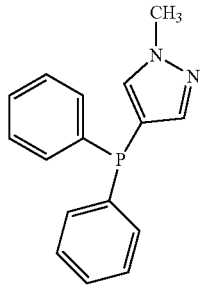 [SMILES: Cn1cc(P(c2ccccc2)c2ccccc2)cn1]

Butyllithium (2.5 M in hexanes) (2.73 mL, 6.83 mmol) was added dropwise to a solution of 4-bromo-1-methyl-1H-pyrazole (0.64 mL, 6.21 mmol) in toluene (10 mL) at −78° C. The resulting reaction mixture was allowed to warm to 0° C. After stirring for 15 min chlorodiphenylphosphine (1.27 mL, 6.83 mmol) was added dropwise and the reaction mixture allowed to warm to room temperature. After stirring for 1 h the reaction mixture was diluted with EtOAc (10 mL) and washed with H$_2$O (10 mL) followed by brine (10 mL). The resulting organics were dried over MgSO$_4$ and solvent removed under vacuo. The resulting residue was purified by chromatography eluting with 0-50% TBME in isohexane to give 4-(diphenylphosphonyl)-1-methyl-1H-pyrazole (0.78 g, 47%) as a colourless oil, which was used in the next step without any further purification.

LC-MS (Method C) 267 [M+H]$^+$; RT 1.56 min (7-carboxyheptyl)(1-methyl-1H-pyrazol-4-yl)diphenylphosphonium bromide

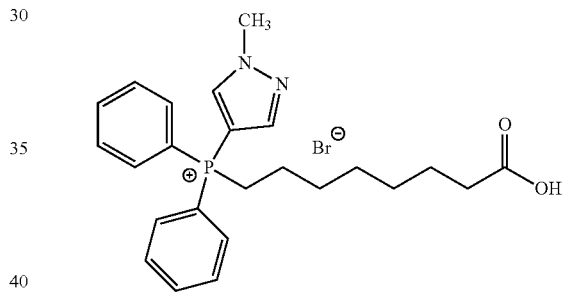

Prepared following the procedure in Example 1 step (a) but using 4-(diphenylphosphonyl)-1-methyl-1H-pyrazole (prepared as described in Example 7 step (a)). Purification was by 0-10% MeOH in DCM. (7-carboxyheptyl)(1-methyl-1H-pyrazol-4-yl)diphenylphosphonium bromide was isolated as colourless gum and used in the next step without any further purification.

LC-MS (Method C) 409 [M]$^+$; RT 0.85 min (7-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}heptyl)(1-methyl-1H-pyrazol-4-yl)diphenylphosphonium chloride

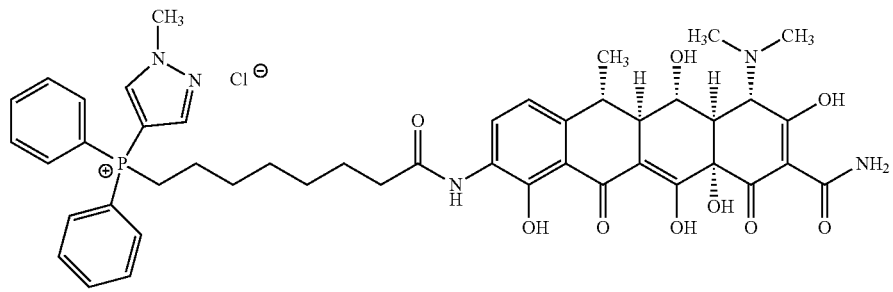 [SMILES: C[C@H]1c2ccc(NC(=O)CCCCCCC[P+](c3ccccc3)(c3ccccc3)c3cnn(C)c3)c(O)c2C(=O)C2=C(O)[C@]3(O)C(=O)C(C(N)=O)=C(O)[C@@H](N(C)C)[C@@H]3[C@@H](O)[C@@H]21 ; [Cl-]]

Prepared following the procedure in Example 2 step (b) but using (7-carboxyheptyl)(1-methyl-1H-pyrazol-4-yl)diphenylphosphonium bromide (prepared as described in Example 8 step (b)). Title compound isolated as a yellow brown solid as its HCl salt.

31P NMR (162 MHz, DMSO-d$_6$) δ (delta) ppm +13.45 (s); LC-MS (Method B) 850 [M]$^+$; RT 3.86 min Example 9—(8-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}octyl)(1-methyl-1H-pyrazol-4-yl)diphenylphosphonium chloride (8-carboxyoctyl)(1-methyl-1H-pyrazol-4-yl)diphenylphosphonium bromide

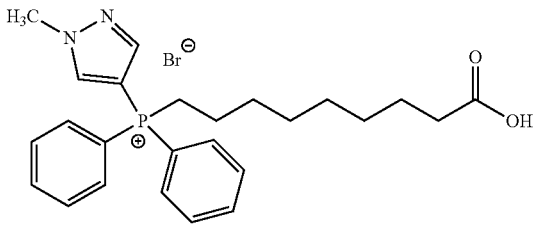 [SMILES: Cn1cc([P+](CCCCCCCCC(=O)O)(c2ccccc2)c2ccccc2)cn1 ; [Br-]]

Prepared following the procedure in Example 1 step (a) but using 4-(diphenylphosphonyl)-1-methyl-1H-pyrazole (prepared as described in Example 8 step (a)) and 9-bromononanoic acid. Purification was by silica column chromatography eluting with 0-10% MeOH in DCM. (8-carboxyoctyl)(1-methyl-1H-pyrazol-4-yl) diphenylphosphonium bromide was isolated as a clear oil and used in the next step without any further purification.

LC-MS (Method C) 423 [M]$^+$; RT 0.91 min (8-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}octyl)(1-methyl-1H-pyrazol-4-yl)diphenylphosphonium chloride

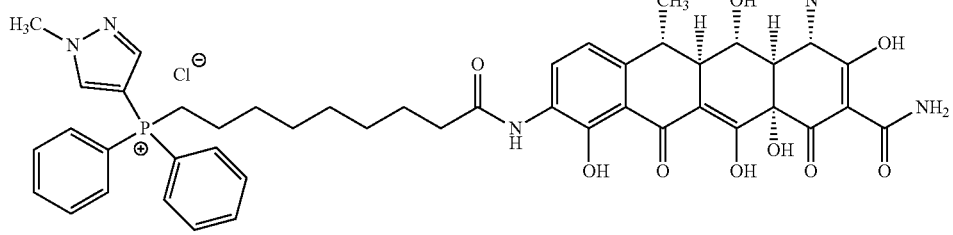

To a solution of (8-carboxyoctyl)(1-methyl-1H-pyrazol-4-yl)diphenylphosphonium bromide (prepared as described in Example 9 step (a)) (150 mg, 0.30 mmol) in DCM (1.3 mL) was added 1-chloro-N,N-2-trimethyl-1-propenylamine (Ghosez's reagent) (52.6 μL, 0.40 mmol). The resulting mixture was stirred at room temperature. After 1 h further 1-chloro-N,N-2-trimethyl-1-propenylamine (52.6 μL, 0.40 mmol) was added and stirring continued. After 30 min the reaction mixture was added dropwise to a stirred solution of 9-aminodoxycyline hydrochloride (99 mg, 0.2 mmol) in DMF (0.46 mL). The resulting reaction mixture was stirred at room temperature for 1 h and then added dropwise to MTBE (50 mL). Following sonication, a yellow solid was isolated by filtration, which was taken up in DCM (20 mL)/H$_2$O (20 mL). The aqueous layer was separated and extracted with DCM (3×20 mL). The combined organic phases were extracted with H$_2$O (3×20 mL). The combined aqueous phases were extracted with n-BuOH (3×20 mL) and the combined n-BuOH extracts concentrated under vacuo. The resulting residue was taken up in toluene and solvent removed under reduced pressure to give a brown residue, which was purified by preparative HPLC (Method A). The resulting brown solid was taken up in MeOH (2 mL) and filtered through an Amberlite IRA-400(CI) ion exchange resin. The collected MeOH was recycled through the column 3×, followed by a fresh volume of MeOH. The combined MeOH washings were concentrated under reduced pressure to give the title compound (48 mg) as a yellow brown solid as its HCl salt.

LC-MS (Method B) 864 [M]$^+$; RT 3.18 min

Example 10—(11-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}undecyl)(1-methyl-1H-pyrazol-4-yl)diphenylphosphonium chloride (11-carboxyundecyl)(1-methyl-1H-pyrazol-4-yl) diphenylphosphonium bromide

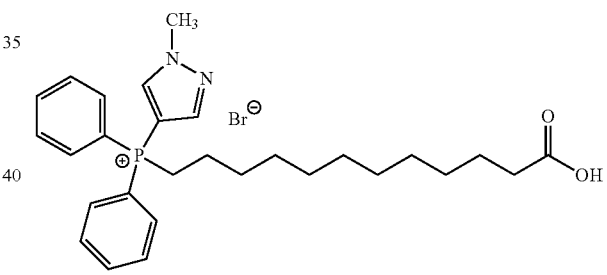

Prepared following the procedure in Example 1 step (a) but using 4-(diphenylphosphonyl)-1-methyl-1H-pyrazole (prepared as described in Example 8 step (a)) and 12-bromododecanoic acid. Purification was by silica column chromatography eluting with 0-10% MeOH in DCM. (11-carboxyundecyl)(1-methyl-1H-pyrazol-4-yl) diphenylphosphonium bromide was isolated as a clear oil and used in the next step without any further purification.

LC-MS (Method C) 465 [M]$^+$; RT 1.54 min (11-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}undecyl)(1-methyl-1H-pyrazol-4-yl)diphenylphosphonium chloride

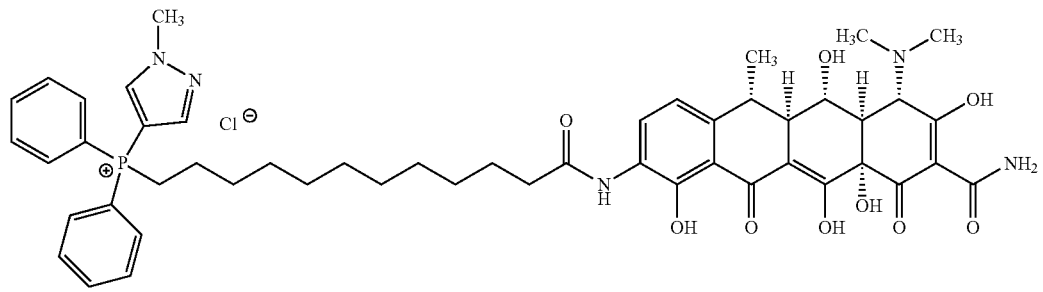 [SMILES: C[C@H]1c2ccc(NC(=O)CCCCCCCCCCC[P+](c3ccccc3)(c3ccccc3)c3cnn(C)c3)c(O)c2C(=O)C2=C(O)[C@]3(O)C(=O)C(C(N)=O)=C(O)[C@@H](N(C)C)[C@@H]3[C@@H](O)[C@@H]21 ; [Cl-]]

Prepared following the procedure in Example 9 step (b) using (11-carboxyundecyl)(1-methyl-1H-pyrazol-4-yl)diphenylphosphonium bromide (prepared as described in Example 10 step (a)). Title compound was isolated as a yellow solid as its HCl salt.

LC-MS (Method B) 907 [M]⁺; RT 4.15 min

Example 11—(9-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}nonyl)(1-methyl-1H-pyrazol-4-yl)diphenylphosphonium chloride (9-carboxynonyl)(1-methyl-1H-pyrazol-4-yl)diphenylphosphonium bromide

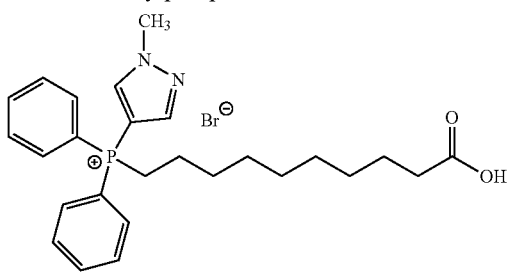

Prepared following the procedure in Example 1 step (a) but using 4-(diphenylphosphonyl)-1-methyl-1H-pyrazole (prepared as described in Example 8 step (a)) and 10-bromodecanoic acid. Purification was by silica column chromatography eluting with 0-10% MeOH in DCM. (9-carboxynonyl)(1-methyl-1H-pyrazol-4-yl) diphenylphosphonium bromide was isolated as a light brown oil and used in the next step without any further purification.

LC-MS (Method C) 437 [M]⁺; RT 0.98 min (9-{[(5R,5a R,6S,6a R,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}nonyl)(1-methyl-1H-pyrazol-4-yl)diphenylphosphonium chloride

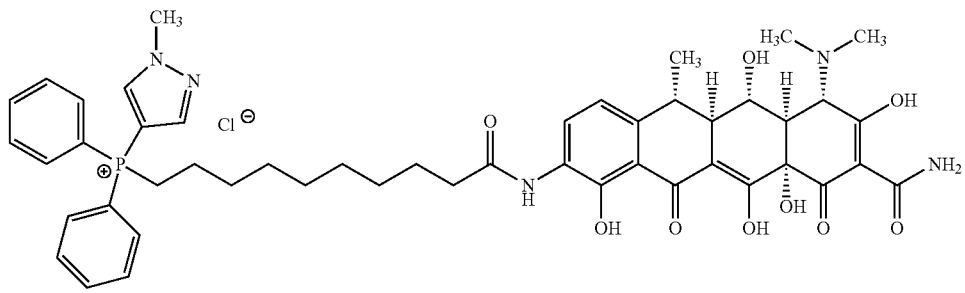 [SMILES: C[C@H]1c2ccc(NC(=O)CCCCCCCCC[P+](c3ccccc3)(c3ccccc3)c3cnn(C)c3)c(O)c2C(=O)C2=C(O)[C@]3(O)C(=O)C(C(N)=O)=C(O)[C@@H](N(C)C)[C@@H]3[C@@H](O)[C@@H]21 ; [Cl-]]

Prepared following the procedure in Example 9 step (b) using (9-carboxynonyl)(1-methyl-1H-pyrazol-4-yl)diphenylphosphonium bromide (prepared as described in Example 11 step (a)). Title compound was isolated as a yellow solid as its HCl salt.

LC-MS (Method B) 879 [M]⁺; RT 3.55 min

Example 12—(10-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}decyl)(1-methyl-1H-pyrazol-4-yl)diphenylphosphonium chloride

(10-carboxydecyl)(1-methyl-1H-pyrazol-4-yl)diphenylphosphonium bromide

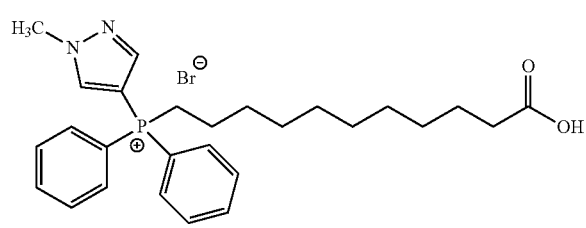 [SMILES: Cn1cc([P+](CCCCCCCCCCC(=O)O)(c2ccccc2)c2ccccc2)cn1 ; [Br-]]

Prepared following the procedure in Example 1 step (a) but using 4-(diphenylphosphonyl)-1-methyl-1H-pyrazole (prepared as described in Example 8 step (a)) and 11-bromoundecanoic acid. Purification was by silica column chromatography eluting with 0-10% MeOH in DCM. (10-carboxydecyl)(1-methyl-1H-pyrazol-4-yl) diphenylphosphonium bromide was isolated as a clear oil and used in the next step without any further purification.

LC-MS (Method C) 451 [M]$^+$; RT 1.05 min

(10-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}decyl)(1-methyl-1H-pyrazol-4-yl)diphenylphosphonium chloride Prepared following the procedure in Example 9 step (b) using (10-carboxydecyl)(1-methyl-1H-pyrazol-4-yl)diphenylphosphonium bromide (prepared as described in Example 12 step (a)). Title compound was isolated as a brown solid as its HCl salt.

LC-MS (Method B) 893 [M]$^+$; RT 3.85 min

Example 13—(11-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}undecyl)diphenyl(propan-2-yl)phosphonium chloride

(11-carboxyundecyl)diphenyl(propan-2-yl)phosphonium bromide

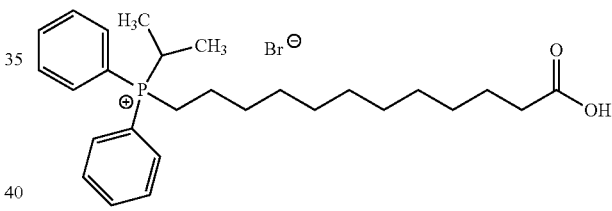

Prepared following the procedure in Example 2 step (a) but using isopropyldiphenylphosphine and 12-bromododecanoic acid. (11-carboxyundecyl)diphenyl(propan-2-yl) phosphonium bromide was isolated as a colourless gum and used in the next step without any further purification.

LC-MS (Method C) 427 [M]$^+$; RT 1.15 min

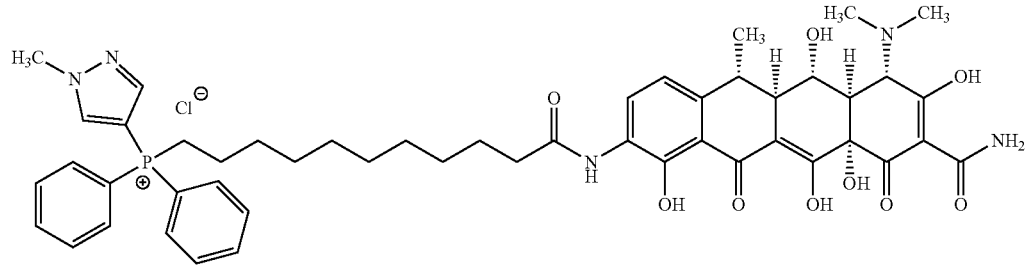 [SMILES: C[C@H]1c2ccc(NC(=O)CCCCCCCCCC[P+](c3ccccc3)(c3ccccc3)c3cnn(C)c3)c(O)c2C(=O)C2=C(O)[C@]3(O)C(=O)C(C(N)=O)=C(O)[C@@H](N(C)C)[C@@H]3[C@@H](O)[C@@H]21 ; [Cl-]]

(11-{[(5R,5aR,6S,6aR,7S,10aS)-9-carbamoyl-7-(dimethylamino)-1,6,8,10a,11-pentahydroxy-5-methyl-10,12-dioxo-5,5a,6,6a,7,10,10a,12-octahydrotetracen-2-yl]carbamoyl}undecyl)diphenyl(propan-2-yl)phosphonium chloride

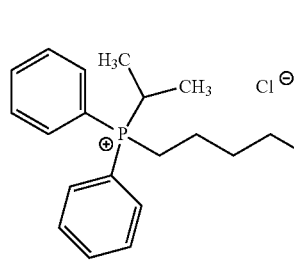
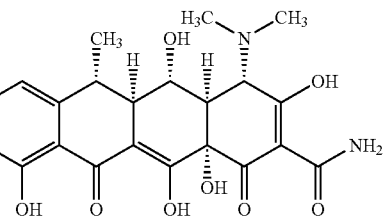

Prepared following the procedure in Example 9 step (b) using (11-carboxyundecyl)diphenyl(propan-2-yl)phosphonium bromide (prepared as described in Example 13 step (a)). Title compound was isolated as a yellow solid as its HCl salt.

LC-MS (Method B) 869 [M]$^+$; RT 4.21 min

Inhibition of Proliferation Assay

Cell Confluence

The confluence value is a surrogate for cell proliferation and growth. The value is expressed as a percent confluence, which represents the fraction of culture dish-surface that is occupied by cells. As the number of cells in the dish increases over time due to proliferation, so will their coverage of that surface increase. Expansion of the cell population on the cell culture-dish surface and confluence have mostly a linear relationship until the cells on the plate surface begin to reach saturation or maximum density.

Confluence is determined based on image analysis. Image based software can identify objects in the image field base on changes to pixel density in a grey scale image. The software can then assign a mask to those pixels within the object. Objects can be 'gated' out based on size and shape. To determine cell confluence, images of cells are first masked as objects. The surface area of the image that is masked is measured and compared to the total surface area of the culture dish surface to obtain a percent confluence.

MDA-231 cancer cells were obtained from ATCC. Cells were cultured in Dulbecco's Modified Eagle Medium (DMEM) supplemented with 10% Fetal Bovine Serum (FBS), 2 mM Glutamax, 1 mM Non Essential Amino Acid (NEAA) solution and 1 mM sodium pyruvate. Compounds were dissolved in DMSO at 10 mM and diluted in cellular medium and tested at 10 uM. Final DMSO concentrations were 50.1%. Images were acquired with an IncuCyte Live Cell Imaging microscopy (Essen Bioscience) at every 3 h under cell culture conditions with 10× objective over 4-5 d. Cell confluence was calculated from one field of view per well using the IncuCyte in-built algorithm. Relative confluence values were obtained by normalising each value to the time zero value in each sample.

| Example | Concentration µM (micromolar) | % Confluence |
|---|---|---|
| Doxycycline | 50 | 91 |
| Doxycycline | 10 | 98.7 |
| 1 | 10 | 17 |
| 2 | 10 | 91.7 |
| 3 | 10 | 62.5 |
| 4 | 10 | 111.8 |
| 5 | 10 | 24.9 |
| 6 | 10 | 57.7 |
| 7 | 10 | 29.4 |
| 8 | 10 | 45.6 |
| 9 | 10 | 55.5 |
| 10 | 10 | 12.4 |
| 11 | 10 | 70.1 |
| 12 | 10 | 45.4 |
| 13 | 10 | 35.1 |

It is anticipated that further compounds of the invention will demonstrate positive cell confluence data.

The invention claimed is:

1. A compound comprising an ion of formula (I) or a pharmaceutically acceptable salt thereof:

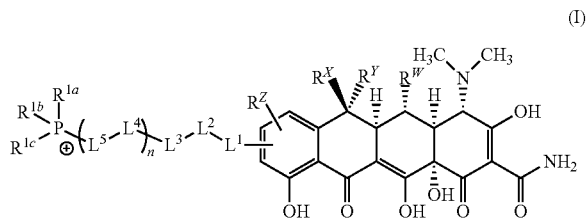

wherein
$R^W$ is H or OH;
$R^X$ is H;
$R^Y$ is H, $C_1$-$C_6$-alkyl or $C_1$-$C_6$-haloalkyl;
$R^Z$ is H, $NR^{Z1}R^{Z2}$, $C_1$-$C_6$-haloalkyl, or halo, wherein $R^{Z1}$ and $R^{Z2}$ are both independently selected from H or $C_1$-$C_6$-alkyl;
-$L^1$- is absent or is —$CR^{2a}R^{2b}$;
-$L^2$- is absent or is independently selected from —O—, —S—, —$NR^{3a}$—, —C(O)$NR^{3b}$—, —C(O)—, —OC(O)—, —$NR^{3b}$C(O)—, $NR^5$S(O)$_2$—, —OC(O)$NR^{3b}$—, —$NR^{3b}$C(O)O— and —$NR^{3b}$C(O)$NR^{3c}$;
-$L^3$- and $L^5$- are each independently at each occurrence selected from —$C_1$-$C_4$-alkylene-, each alkylene group being unsubstituted or substituted with from 1 to 10 independently selected $R^4$ groups; provided that any -$L^3$- or -$L^5$- group that is attached at each end to an atom selected from oxygen, nitrogen, sulphur or phosphorous is —$C_2$-$C_4$-alkylene-;
-$L^4$- is independently at each occurrence either absent or is selected from: —O—, —S—, —$NR^{3a}$—, —C(O)—, —OC(O)—, —C(O)O—, —$SO_2$—, —S(O)—, —NR$^{3b}$C(O)—, —C(O)NR$^{3b}$, NR$^{3b}$S(O)$_2$—, —S(O)$_2$NR$^{3b}$—, —OC(O)NR$^{3b}$—, —NR$^{3b}$C(O)O—, NR$^{3b}$C(O)NR$^{3c}$, —CR$^{5a}$=CR$^{5b}$— and —C≡C—;

n is an integer selected from 0, 1, 2, 3, 4 and 5;

wherein L$^1$, L$^2$, L$^3$ L$^4$ and L$^5$ together form a linker and L$^1$, L$^2$, L$^3$ L$^4$ and L$^5$ are selected such that length of the linker is from 3 to 16 atoms;

R$^{1a}$, R$^{1b}$ and R$^{1c}$ are each independently selected from phenyl, biphenyl, naphthyl, 5-, 6-, 9- or 10-membered heteroaryl, C$_3$ to C$_8$-cycloalkyl, C$_1$-C$_8$-alkyl and 4- to 8-membered heterocycloalkyl;

wherein said phenyl, biphenyl, naphthyl, 5-, 6-, 9- or 10-membered heteroaryl is optionally substituted with from 1 to 5 independently selected R$^{1d}$ groups; and wherein said C$_3$ to C$_8$-cycloalkyl, C$_1$-C$_8$-alkyl and 4- to 8-membered heterocycloalkyl is optionally substituted with from 1 to 5 independently selected R$^{1e}$ groups; provided that R$^{1a}$, R$^{1b}$ and R$^{1c}$ are not each unsubstituted phenyl; wherein R$^{1a}$ and R$^{1b}$ are optionally connected to each other via a bond or a group selected from —O—, NR$^{6a}$, and C$_1$-C$_3$-alkylene;

R$^{1d}$ is independently at each occurrence selected from: C$_1$-C$_6$-alkyl, C$_2$-C$_6$-alkynyl, C$_2$-C$_6$-alkenyl, C$_1$-C$_6$-haloalkyl, C$_3$-C$_6$-cycloalkyl, 5- to 8-membered heterocycloalkyl, 5-, 6-, 9- or 10-membered heteroaryl, phenyl, OR$^6$, SR$^7$, NR$^7$R$^8$, C(O)OR$^7$, C(O)NR$^7$R$^7$, halo, cyano, nitro, C(O)R$^7$, S(O)$_2$OR$^7$, S(O)R$^7$, S(O)$_2$R$^7$ and S(O)$_2$NR$^7$R$^7$;

R$^{1e}$ is independently at each occurrence selected from: oxo, C$_1$-C$_6$-alkyl, C$_2$-C$_6$-alkynyl, C$_2$-C$_6$-alkenyl, C$_1$-C$_6$-haloalkyl, C$_3$-C$_6$-cycloalkyl, 5- to 8-membered heterocycloalkyl, 5-, 6-, 9- or 10-membered heteroaryl, phenyl, OR$^6$, SR$^7$, NR$^7$R$^8$, C(O)OR$^7$, C(O)NR$^7$R$^7$, halo, cyano, nitro, C(O)R$^7$, S(O)$_2$OR$^7$, S(O)R$^7$, S(O)$_2$R$^7$, S(O)$_2$NR$^7$R$^7$, OC(O)NR$^7$R$^7$ and NR$^7$C(O)OR$^6$;

R$^{2a}$ and R$^{2b}$ are each independently selected from H and C$_1$-C$_4$-alkyl;

R$^{3a}$, is independently at each occurrence selected from H, C$_1$-C$_6$-alkyl, —C(O)H, —C(O)—C$_1$-C$_6$-alkyl and —S(O)$_2$—C$_1$-C$_6$-alkyl R$^{3b}$ and R$^{3c}$ are each independently at each occurrence selected from H and C$_1$-C$_6$-alkyl;

R$^4$ is independently at each occurrence selected from: C$_1$-C$_6$-alkyl, C$_2$-C$_6$-alkynyl, C$_2$-C$_6$-alkenyl, C$_1$-C$_6$-haloalkyl, OR$^6$, SR$^7$, NR$^7$R$^8$, C(O)OR$^7$, C(O)NR$^7$R$^7$, halo, cyano, nitro, C(O)R$^7$, S(O)$_2$OR$^7$, S(O)R$^7$, S(O)$_2$R$^7$ and S(O)$_2$NR$^7$R$^7$;

R$^{5a}$ and R$^{5b}$ are independently at each occurrence selected from H, C$_1$-C$_4$-alkyl and halo;

R$^6$ is independently at each occurrence selected from: H, C$_1$-C$_6$-alkyl and C$_1$-C$_6$-haloalkyl;

R$^7$ and R$^{6a}$ are independently at each occurrence selected from: H and C$_1$-C$_6$-alkyl;

R$^8$ is independently at each occurrence selected from: H, C$_1$-C$_6$-alkyl, C(O)C$_1$-C$_6$-alkyl and S(O)$_2$—C$_1$-C$_6$-alkyl;

and wherein any of the abovementioned alkyl, alkenyl, alkynyl, cycloalkyl, heterocycloalkyl, heteroaryl or phenyl groups is optionally substituted where chemically allowable by from 1 to 4 groups independently selected from oxo, C$_1$-C$_6$-alkyl, C$_2$-C$_6$-alkynyl, C$_2$-C$_6$-alkenyl, C$_1$-C$_6$-haloalkyl, OR$^a$, NR$^a$R$^b$, SR$^a$, C(O)OR$^a$, C(O)NR$^a$R$^a$, halo, cyano, nitro, C(O)R$^a$, S(O)$_2$OR$^a$, S(O)$_2$R$^a$ and S(O)$_2$NR$^a$R$^a$; wherein R$^a$ is independently at each occurrence selected from: H and C$_1$-C$_6$-alkyl; and R$^b$ is independently at each occurrence selected from: H, C$_1$-C$_6$-alkyl, C(O)C$_1$-C$_6$-alkyl and S(O)$_2$—C$_1$-C$_6$-alkyl.

2. The compound of claim 1, wherein R$^Z$ is H, R$^X$ is H, R$^Y$ is CH$_3$, and R$^W$ is OH.

3. The compound of claim 1, wherein R$^Z$ is NMe$_2$, R$^X$ is H, R$^Y$ is H, and R$^W$ is H.

4. The compound of claim 1, wherein L$^1$ is absent.

5. The compound of claim 1, wherein L$^1$ is CR$^{2a}$R$^{2b}$.

6. The compound of claim 1, wherein L$^2$ is —NR$^{3b}$C(O)—.

7. The compound of claim 1, wherein -(L$^5$-L$^4$-)$_n$-L$^3$ is —(CR$^{4a}$R$^{4b}$)$_o$-L$^4$-(CR$^{4c}$R$^{4d}$)$_p$—, wherein o is selected from 3 to 10; p is selected from 1 to 3; wherein R$^{4a}$ and R$^{4b}$ are each independently at each occurrence selected from: H, C$_1$-C$_6$-alkyl, C$_1$-C$_6$-haloalkyl, OR$^6$, and NR$^7$R$^8$; and R$^{4c}$ and R$^{4d}$ are each independently at each occurrence selected from: H and methyl.

8. The compound according to claim 7, wherein -L$^4$- is —NR$^{3b}$C(O)—.

9. The compound according to claim 7, wherein -L$^4$- is absent.

10. The compound of claim 1, wherein n, L$^1$, L$^2$, L$^3$, L$^4$ and L$^5$ are selected such that length of the linker is from 8 to 14 atoms.

11. The compound of claim 1, wherein R$^{1a}$, R$^{1b}$ and R$^{1c}$ are each substituted phenyl.

12. A compound of claim 1, wherein R$^{1a}$, R$^{1b}$ and R$^{1c}$ are each C$_3$ to C$_8$-cycloalkyl.

13. The compound of claim 1, wherein R$^{1a}$R$^{1b}$ and R$^{1c}$ are each benzyl.

14. The compound of claim 1, wherein R$^{1a}$ and R$^{1b}$ are each unsubstituted phenyl and R$^{1c}$ is independently selected from: substituted phenyl, biphenyl, naphthyl, 5-, 6-, 9- or 10-membered heteroaryl, C$_3$ to C$_8$-cycloalkyl, C$_1$-C$_8$-alkyl and 4- to 8-membered heterocycloalkyl.

15. The compound of claim 1, wherein R$^{1a}$ and R$^{1b}$ are each C$_3$ to C$_8$-cycloalkyl and R$^{1c}$ is independently selected from: phenyl, biphenyl, naphthyl, 5-, 6-, 9- or 10-membered heteroaryl, C$_1$-C$_8$-alkyl and 4- to 8-membered heterocycloalkyl.

16. The compound of claim 1, wherein at least one of R$^{1a}$, R$^{1b}$ and R$^{1c}$ is C$_1$-C$_6$-alkyl.

17. The compound of claim 16, wherein any of R$^{1a}$, R$^{1b}$ and R$^{1c}$ that are not C$_1$-C$_6$-alkyl are phenyl.

18. The compound according to claim 1, wherein the cation of formula (I) is a formula selected from:

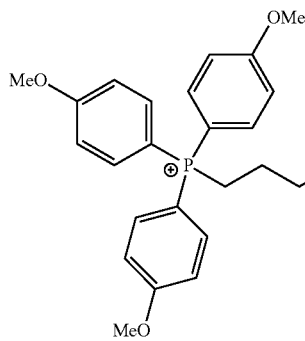 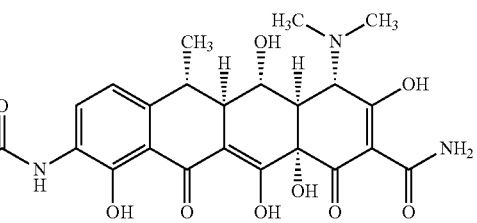

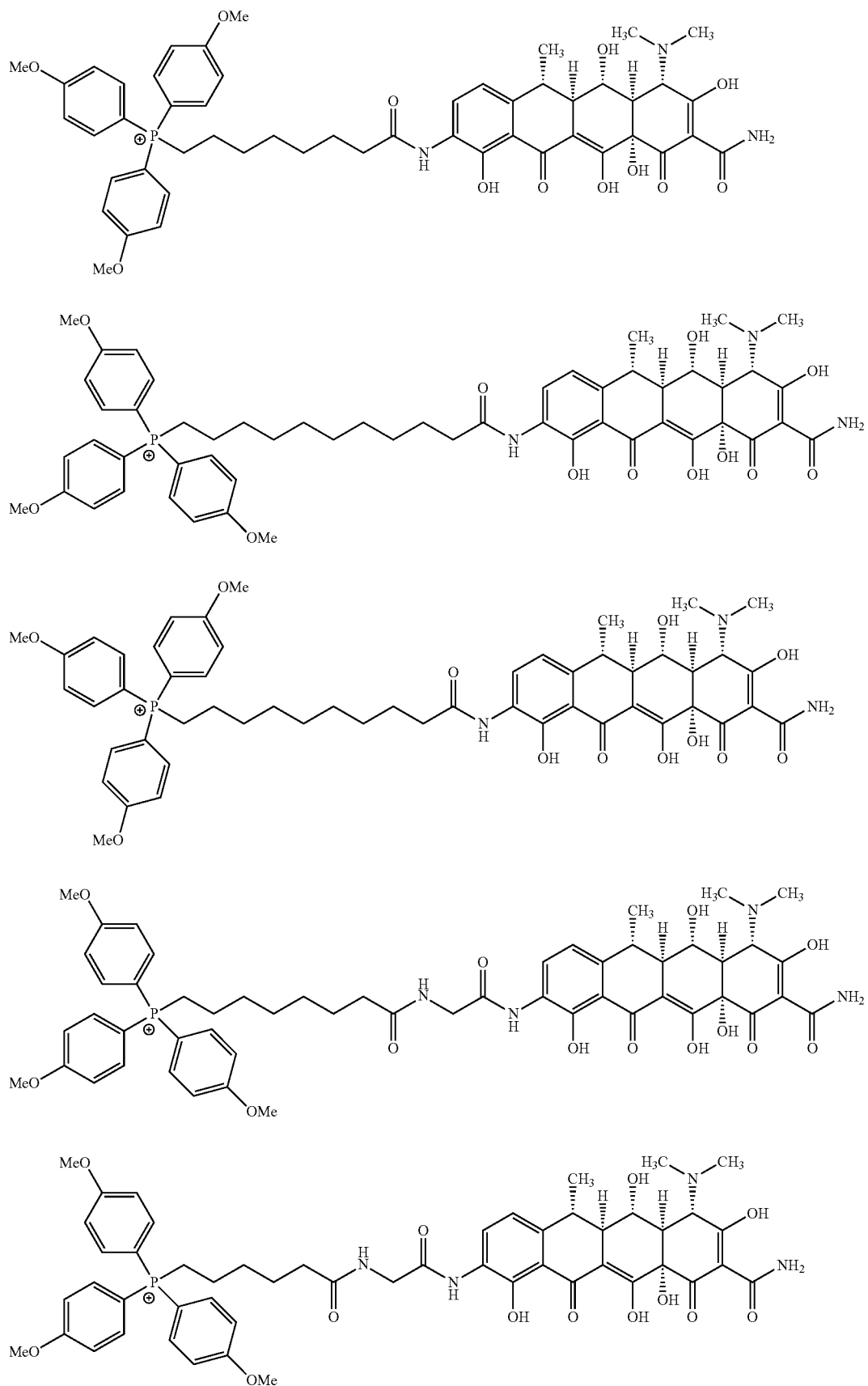

-continued
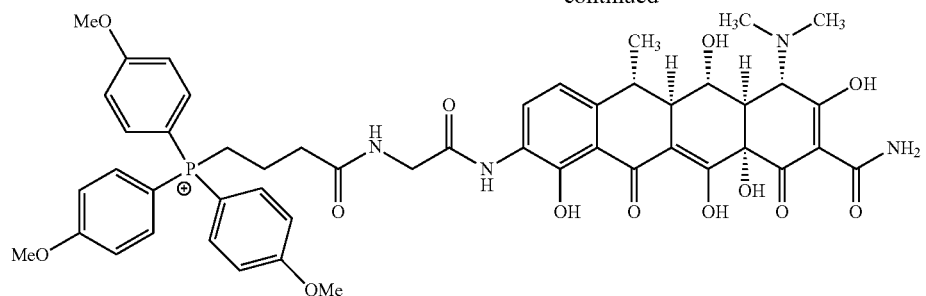
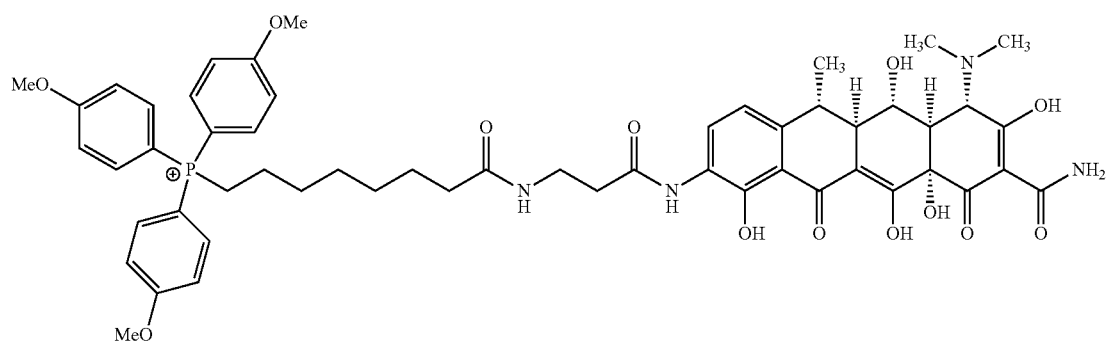
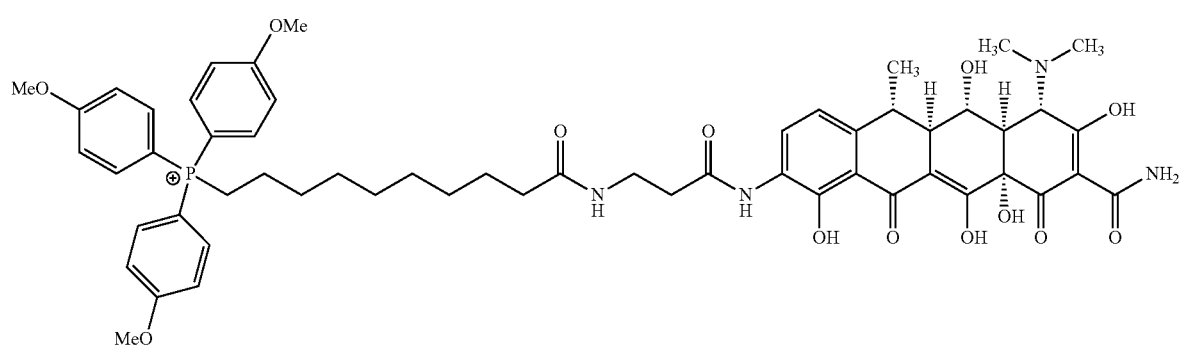
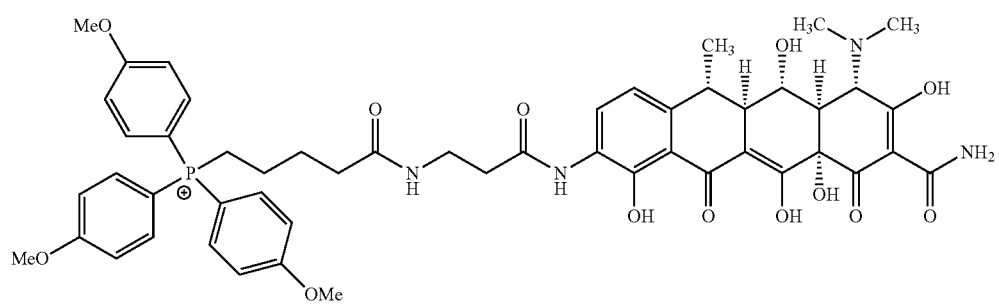
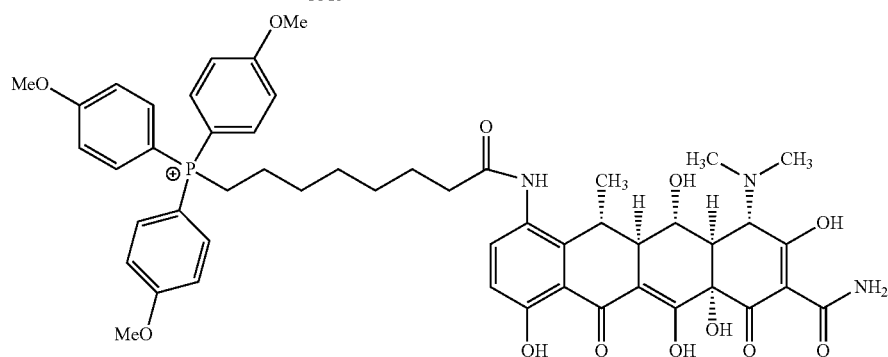

-continued
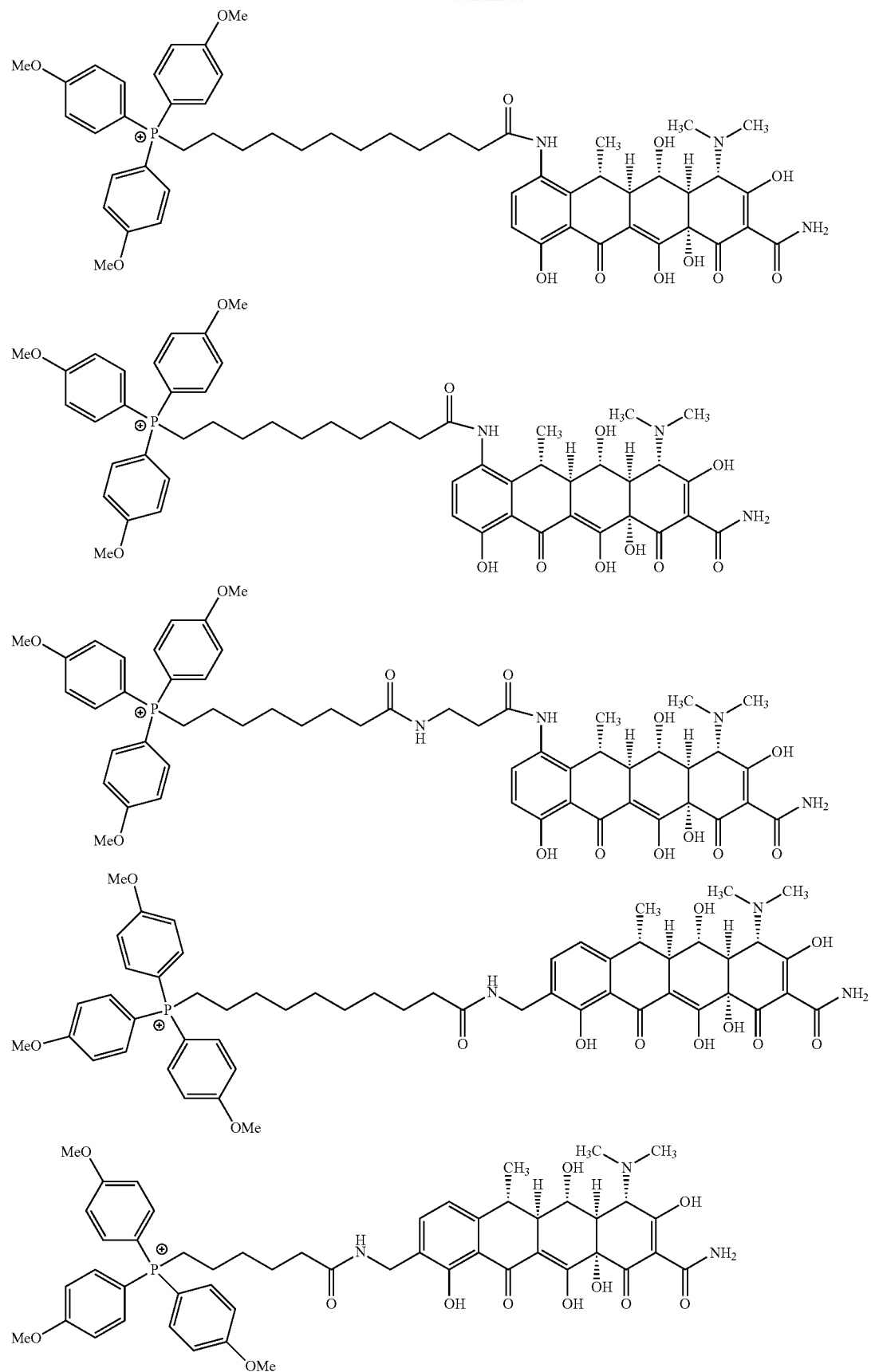

-continued
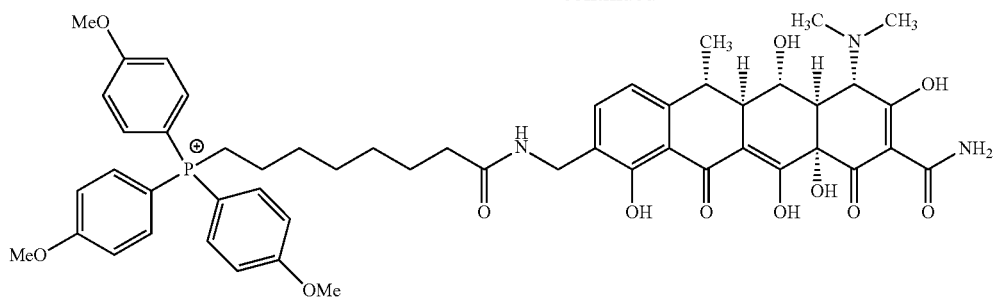
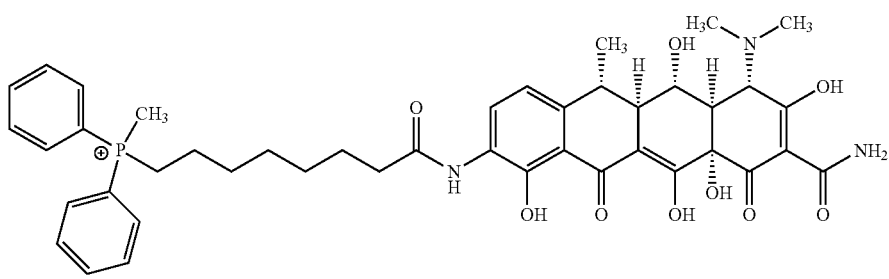
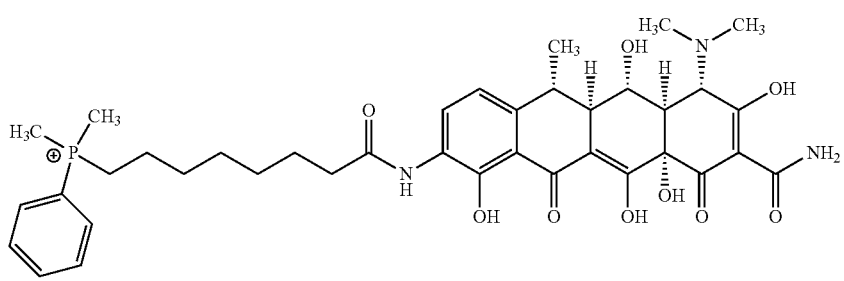
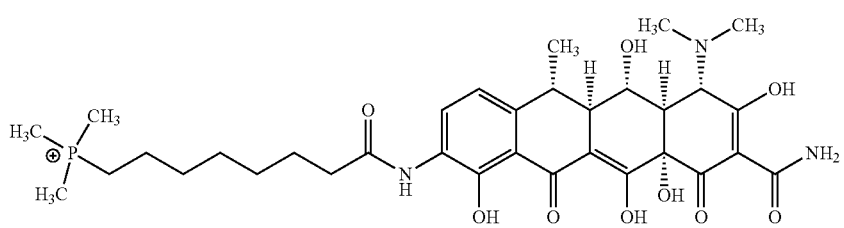
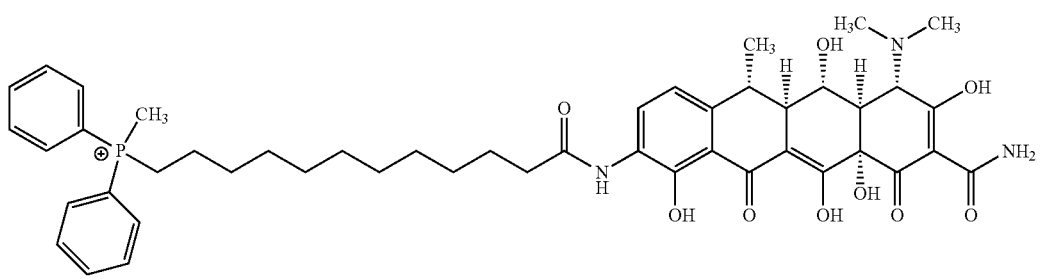
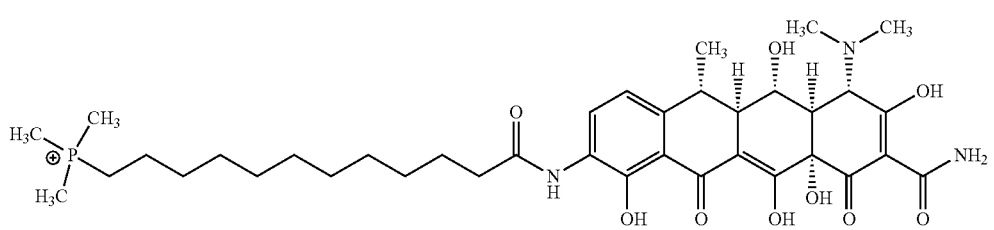

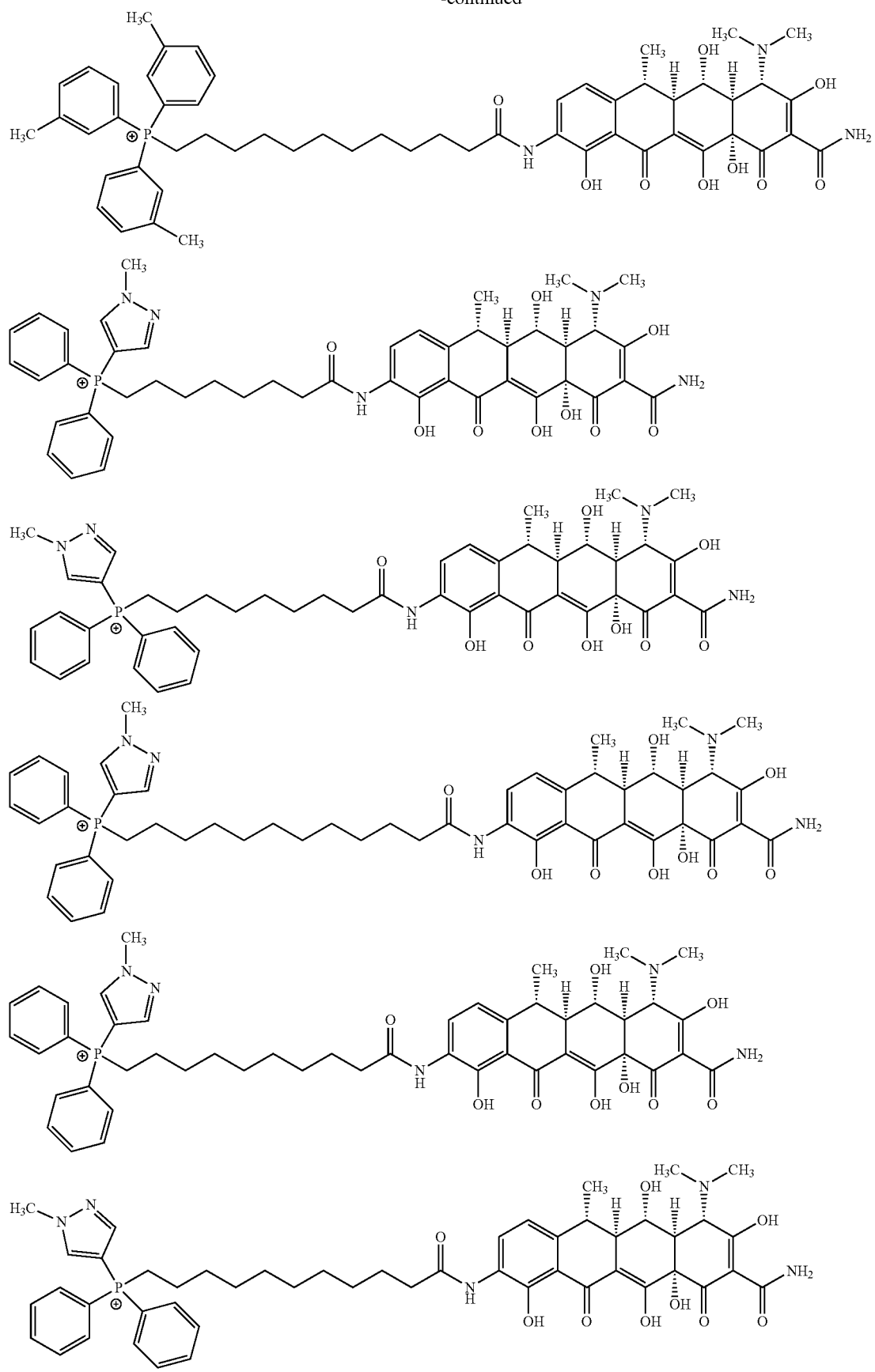

-continued
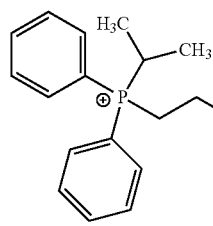 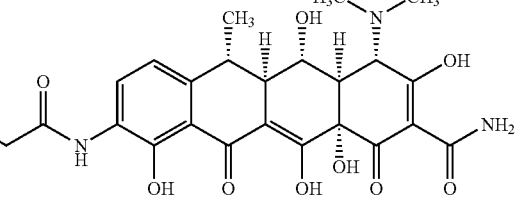
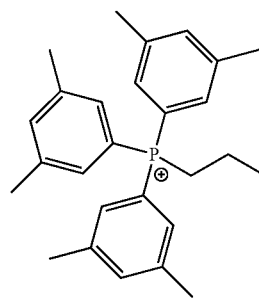 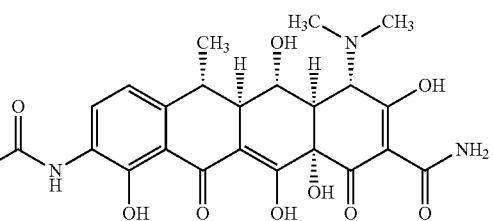
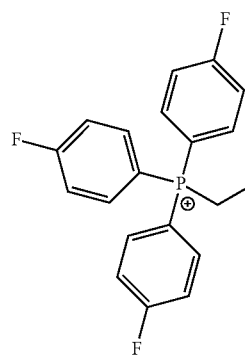 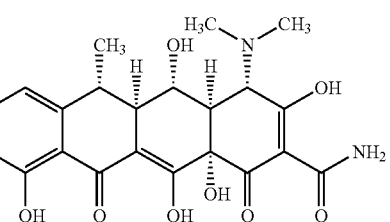
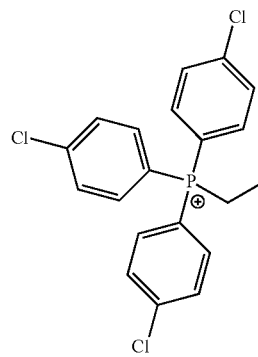 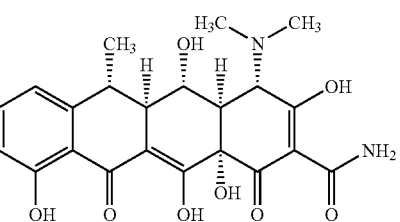
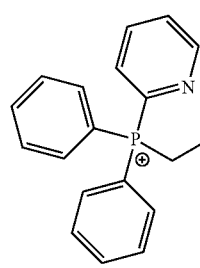 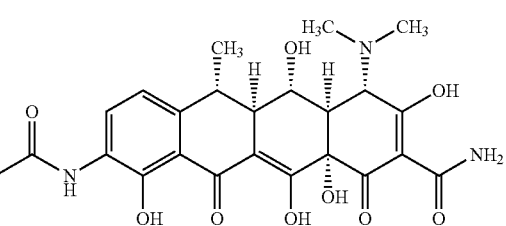

-continued
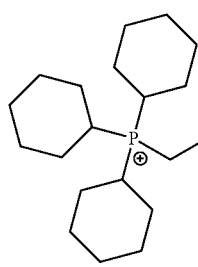 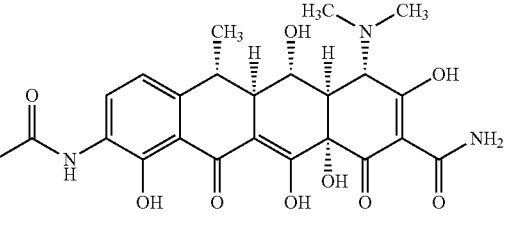
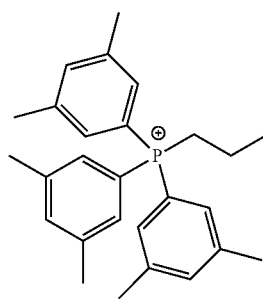 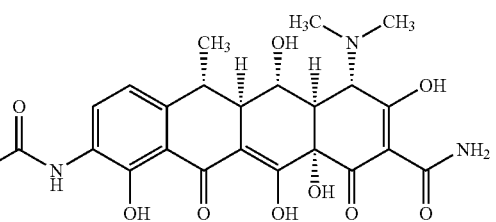
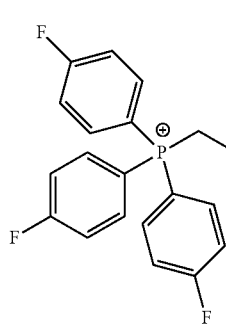 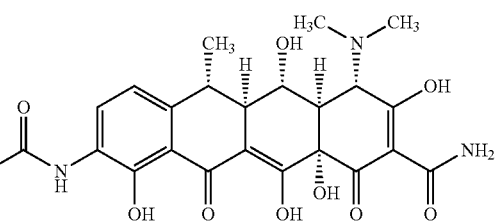
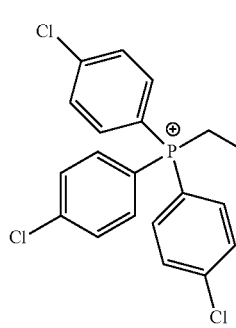 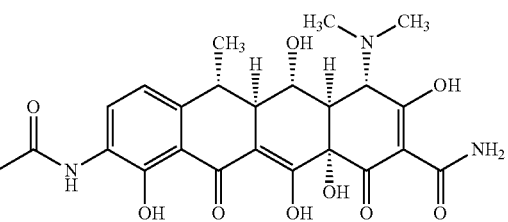
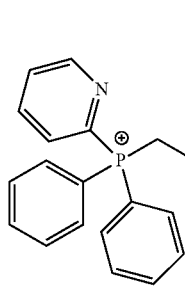 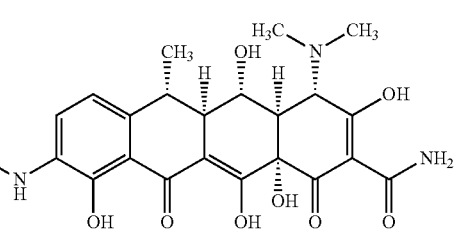

103 104
-continued
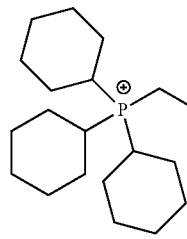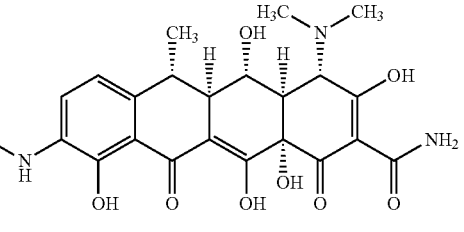
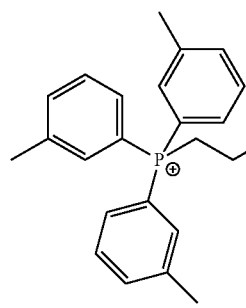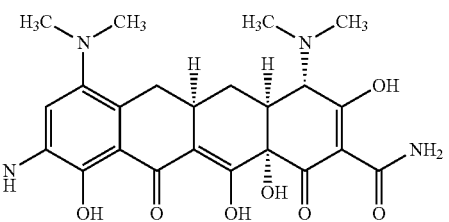
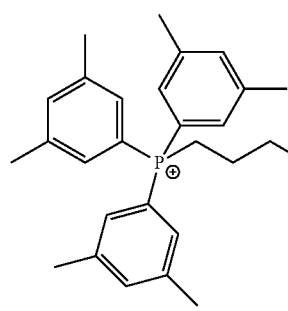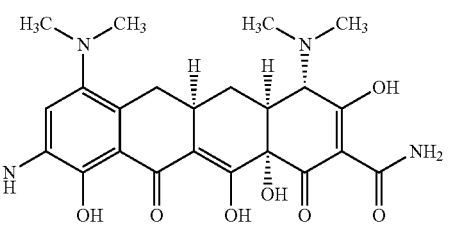
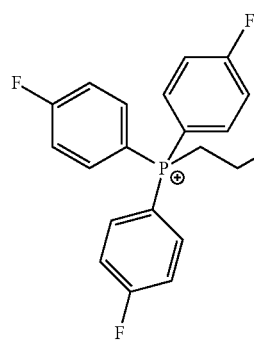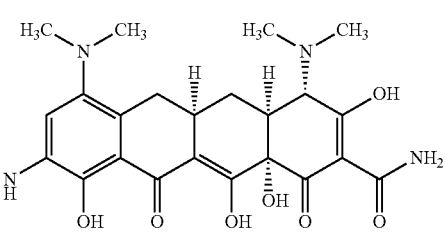
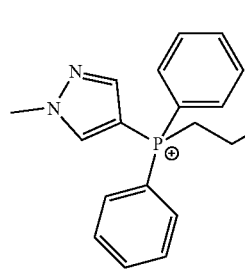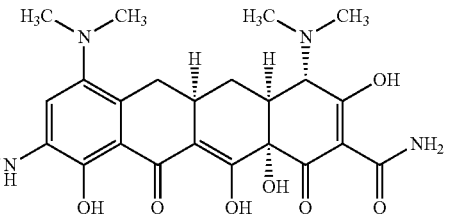

-continued
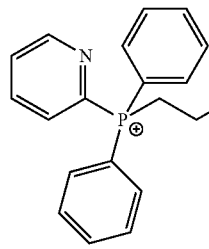 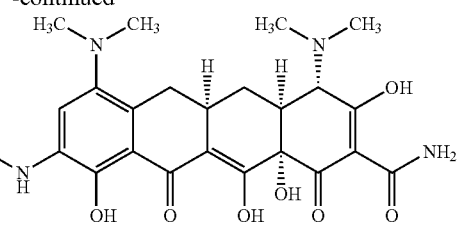
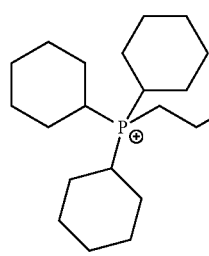 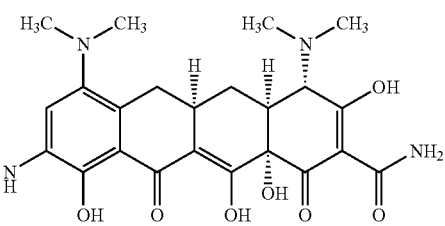
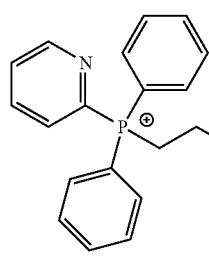 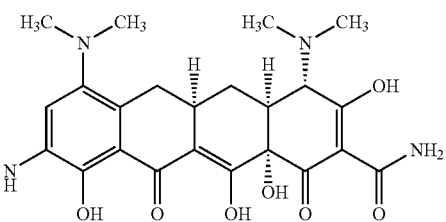
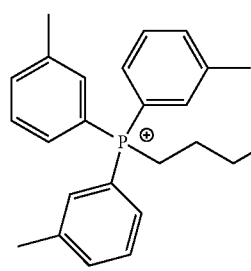 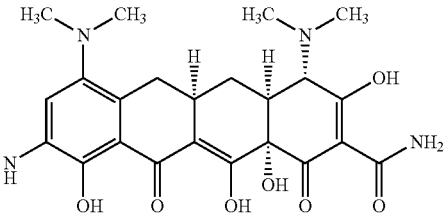
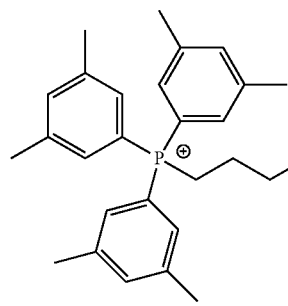 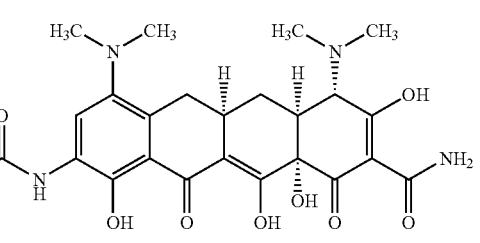

-continued
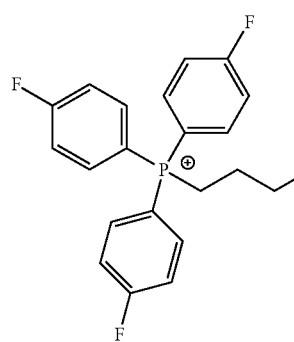
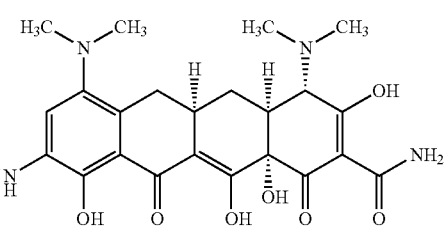
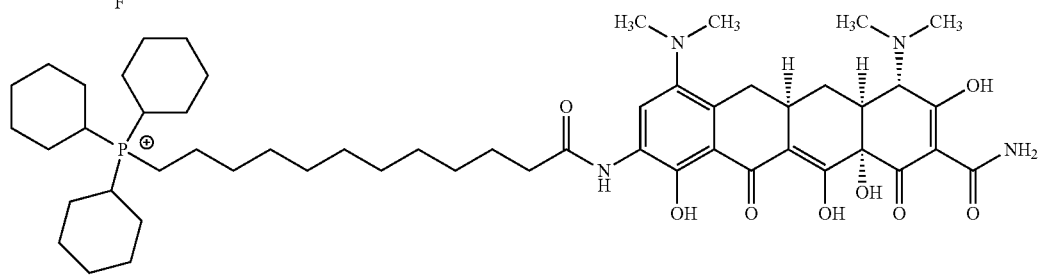
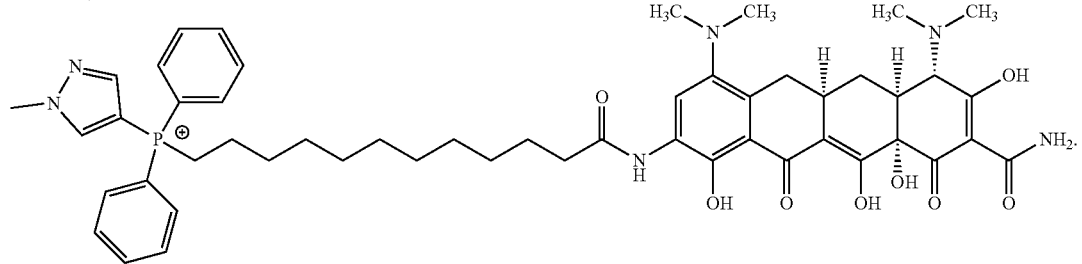
and
19. A method for the treatment of cancer, comprising administering to a subject in need thereof a therapeutically effective amount of a compound of claim 1.
20. A pharmaceutical composition comprising a compound of claim 1; and one or more pharmaceutically acceptable excipients.
* * * * *